(12) United States Patent
Tarleton

(10) Patent No.: US 7,780,969 B2
(45) Date of Patent: Aug. 24, 2010

(54) TRYPANOSOMA CRUZI PROTEOME COMPOSITIONS AND METHODS

(75) Inventor: Rick L. Tarleton, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/486,710

(22) Filed: Jul. 14, 2006

(65) Prior Publication Data

US 2007/0178100 A1    Aug. 2, 2007

Related U.S. Application Data

(60) Provisional application No. 60/699,736, filed on Jul. 15, 2005.

(51) Int. Cl.
*A61K 39/00* (2006.01)
(52) U.S. Cl. .............. 424/269.1; 424/184.1; 424/191.1; 424/265.1; 435/243; 435/258.1; 530/350; 536/23.1; 536/23.7
(58) Field of Classification Search .................. None
See application file for complete search history.

(56) References Cited

U.S. PATENT DOCUMENTS

| | | | |
|---|---|---|---|
| 4,341,761 | A | 7/1982 | Ganfield et al. |
| 4,399,121 | A | 8/1983 | Albarella et al. |
| 4,427,783 | A | 1/1984 | Newman et al. |
| 4,444,887 | A | 4/1984 | Hoffmann |
| 4,452,570 | A | 6/1984 | Fujisaki et al. |
| 4,466,917 | A | 8/1984 | Nussenzweig et al. |
| 4,472,500 | A | 9/1984 | Milstein et al. |
| 4,491,632 | A | 1/1985 | Wands et al. |
| 4,493,890 | A | 1/1985 | Morris |
| 4,816,567 | A | 3/1989 | Cabilly et al. |
| 6,368,827 | B1 | 4/2002 | Tarleton et al. |
| 6,419,933 | B1 | 7/2002 | Reed et al. |
| 6,833,262 | B1 | 12/2004 | Travis et al. |
| 6,875,584 | B1 | 4/2005 | Tarleton et al. |
| 2002/0182223 | A1* | 12/2002 | LaCount et al. .......... 424/191.1 |
| 2004/0241729 | A1 | 12/2004 | Liew |
| 2005/0158347 | A1 | 7/2005 | Tarleton et al. |
| 2005/0244505 | A1 | 11/2005 | Higbee et al. |
| 2006/0228300 | A1 | 10/2006 | Chang et al. |

FOREIGN PATENT DOCUMENTS

WO    2005/111622 A2    11/2005

OTHER PUBLICATIONS

Allaoui et al. Molecular Microbiology 1999 vol. 32 p. 1273-1286.*
Yang et al. Science 1996 vol. 272 p. 1353-1356.*
Zou et al. Journal of Biological Chemistry, 2002 vol. 277 p. 31062-31071.*
Caler et al. The EMBO journal. 1998 vol. 17 p. 4975-4986.*
Bork Peter. 2000 Genome Research p. 398-400.*
Ellis, R.W. (Chapter 29 of "Vaccines" [Plotkin, S.A. et al. (Eds) published by W. B. Saunders Company (Philadelphia) in 1988.*
Oplinger, Anne. NIH Record. vol. LVII No. 9 May 6, 2005.*
El- Sayed et al, Jul. 15, 2005 vol. 39 p. 409-415.*
Williams, Philip Lee. University of Georgia Press Release. Jul. 14, 2005.*
Kolker et al. Nucleic Acid Research, 2004, vol. 32. No. 8 2353-23610.*
Tarleton et al. PLOS medicine. Dec. 2007, vol. 4 issue 12 p. 1852-1857.*
Definition of Vaccine in: The Dictionary of Immunology, Herberts et al eds, Academic Press, 1995.*
Martin et al. PloS Pathog 2(8):e77, p. 731-740.*
Ouaissi et al (Experimental Parasitology 81, 453-461, 1995).*
Coughlin et al. Journal of Biological Chemistry Vo. 275, No. 16, p. 12051-12060 (2000).*
U.S. Appl. No. 11/587,283, filed Oct. 23, 2006, Tarleton et al.
Agüero et al., "TcruziDB: an integrated, post-genomics community resource for *Trypanosoma cruzi*," *Nucleic Acids Research*, 2006; 34(Database issue):D428- D431; doi:10.1093/nar/gkj108.
Akopyants et al., "A survey of the *Leishmania major* Friedlin strain V1 genome by shotgun sequencing: a resource for DNA microarrays and expression profiling," *Mol. Biochem Parasitol*, 2001; 113:337-340.
Almeida et al., "Expression profiling of the *Leishmania* life cycle: cDNA arrays indentify developmentally regulated genes present but not annotated in the genome," *Mol Biochem Parasitol*, 2004; 136:87-100.
Atwood III, et al., "The *Trypanosoma cruzi* Proteome," *Science*, Jul. 15, 2005; 309:473-476 (*available on-line* Jul. 14, 2005), with on-line supporting data (14 pgs).
Atwood et al., "The *Trypanosoma cruzi* Proteome," TriTryp Genomes Meeting. Sep. 13-16, 2004. Seattle, Washington. Abstracts Cover Page, with Abstract p. 6.4.
Berman et al., "Uptake, Distribution, and Oxidation of Fatty Acids by *Leishmania* mexicana Amastigotes," *J. Parasitol*, 1987; 73:555-560.
Berriman et al., "The Genome of the African Trypanosome *Trypanosoma Brucei*," *Science*, Jul. 15, 2005; 309(5733):416-422 (*available on-line* Jul. 14, 2005), with on-line supporting data (61 pgs).
Bringaud et al., "A New, Expressed Multigene Family Containing a Hot Spot for Insertion of Retroelements Is Associated with Polymorphic Subtelomeric Regions of *Trypanosoma brucei*," *Eukaryot Cell*, 2002; 1:137-151.
Clayton, "Life without transcriptional control? From fly to man and back again," *Embo J*, 2002; 21;1881-1888.
Cohen et al., "Modeling Household Transmission of American Trypanosomiasis," *Science*, 2001; 293(5530):694-698.
DGPI, Kronegg, 1999; http://129.194.185.165/dgpi/ 2 pages.
Diehl et al., "Analysis of stage-specific gene expression in the bloodstream and the procyclic form of *Trypanosoma brucei* using a genomic DNA-microarray," *Mol Biochem Parasitol*, 2002; 123:115-123.

(Continued)

*Primary Examiner*—Robert Mondesi
*Assistant Examiner*—Oluwatosin Ogunbiyi
(74) *Attorney, Agent, or Firm*—Mueting Raasch & Gebhardt, P.A.

(57) ABSTRACT

Molecular targets are identified in *T. cruzi* suitable for use in diagnosis of Chagas disease, drug development, and vaccines, including live vaccines.

Figure 1:
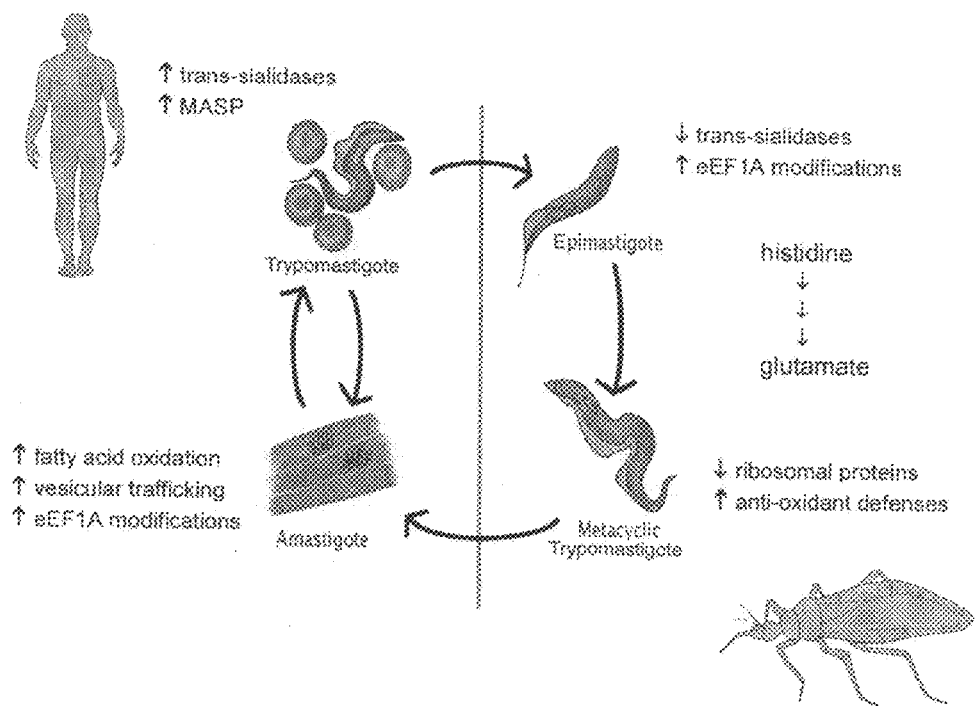

17 Claims, 32 Drawing Sheets
(2 of 32 Drawing Sheet(s) Filed in Color)

OTHER PUBLICATIONS

DiNoia et al., "The Protozoan *Trypanosoma cruzi* Has a Family of Genes Resembling the Mucin Genes of Mammalian Cells," *J Biol Chem*, 1995; 270:24146-24149.

Donnelly et al., "DNA Vaccines," *Rev. Immunol.*, 1997; 15:617-648.

Duncan, "DNA microarray analysis of protozoan parasite gene expression: outcomes correlate with mechanisms of regulation," *Trends Parasitol*, 2004; 20:211-215.

Ejiri, "Moonlighting Functions of Polypeptide Elongation Factor 1: From Actin Bundling to Zinc Finger Protein R1-Associated Nuclear Localization," *Biosci Biotechnol Biochem*, 2002; 66:1-21.

El-Sayed et al., "The Genome Sequence of *Trypanosoma cruzi*, Etiologic Agent of Chagas Disease," *Science*, Jul. 15, 2005; 309:409-415 (*available on-line* Jul. 14, 2005), with on-line supporting data (422 pages).

Evans et al., "The Utilization of Glucose and Proline by Culture Forms of *Trypanosoma brucei*," *J Protozool*, 1972; 19:686-690.

Florens et al., "A proteomic view of the *Plasmodium falciparum* life cycle," *Nature*, 2002, 419:520-526.

Fouts et al., "Nucleotide sequence and transcription of a trypomastigote surface antigen gene of *Trypanosoma cruzi*," *Mol. Biochem. Parasitol.* 1991; 46:189-200.

Frasch, "Functional Diversity in the Trans-sialidase and Mucin Families in *Trypanosoma cruzi*," *Parasitol Today*, 2000; 16:282-286.

Ghaemmaghami et al., "Global analysis of protein expression in yeast," *Nature*, 2003; 425:737-741.

Hammerling et al., "Monoclonal Antibodies and T-Cell Hybridomas," 1981. Title Page, Copyright Page and Table of Contents.

Harington, "Histamine and Histidine in Excreta of the Blood-sucking Bug *Rhodnius prolixus*," *Nature*, 1956, 178:268.

Harington, "Studies of the amino acids of *Rhodnius prolixus*," *Parasitology*, 1961, 51:309-318.

Hoffman et al., "Toward clinical trials of DNA vaccines against malaria," *Immunol. Cell Biol.*, 1997; 75:376-381.

Isola et al., "*Trypanosoma cruzi* Morphogenesis: Preliminary Purification of an Active Fraction from Hemolymph and Intestinal Homogenate of Triatoma infestans," *J Parasitol*, 1986; 72:467-469.

Jones et al., "Replacing the complementarity-determining regions in a human antibody with those from a mouse," *Nature*, 1986; 321:522-525.

Jurgens et al., "Purification and Characterization of Camp-Factor From *Streptococcus agalactiae* by Hydrophobic Interaction Chromatography and Chromatofocusing," *J. Chrom.*, 1985; 348:363-370.

Kennett et al., *Monoclonal Antibodies*, 1980. Title Page, Copyright Page and Table of Contents.

Kissinger et al., "TcruziDB: A Project Update," TriTryp Genomes Meeting. Sep. 13-16, 2004. Seattle, Washington. Abstracts Cover Page, with Abstract p. 3.5.

Kyoto Encyclopedia of Genes and Genomes (KEGG); available on the world wide web at genome.jp/kegg/. Pathways developed by Fairlamb (see http://tbdb.bioinformatics.dundee.ac.uk.kegg.. 1 page.

Low et al., "Molecular cloning of the gene encoding the 83 κDA amastigote surface protein and its identification as a member of the *Trypanosoma cruzi* sialidase superfamily," *Mol. Biochem. Parasitol.* 1997; 88:137-149.

Low et al., "Amastigote Surface Proteins of *Trypanosoma cruzi* Are Targets for CD8+ CTL," *Mol. Biochem. Parasitol*, 1997; 160:1817-1823.

Mann et al., "Proteomic analysis of post-translational modifications," *Nat Biotechnol*, 2003; 21:255-261.

Marszalek et al., "Acyl-CoA Synthetase 2 Overexpression Enhances Fatty Acid Internalization and Neurite Outgrowth," *J Biol Chem.*, 2004; 279(23):23882-23891. Additions and Corrections (1 page).

Martin et al., "Generation, specificity, and function of CD8+ T cells in *Trypanosoma cruzi* infection," *Immunol Rev.*, 2004; 201:304-317.

Martinez-Calvillo et al., "Transcription of *Leishmania major* Friedlin Chromosome 1 Initiates in Both Directions within a Single Region," *Mol Cell*, 2003; 11:1291-1299.

Minning et al., "Microarray profiling of gene expression during trypomastigote to anastigote transition in *Trypanosoma cruzi*," *Mol Biochem Parasitol*, 2003;131:55-64.

Mulder et al., "The InterPro Database, 2003 brings increased coverage and new features," *Nucleic Acids Res*, 2003; 31:315-318.

National Center for Biotechnology Information, National Library of Medicine, National Institutes of Health, GenBank Locus TRBTSA1, Accession No. M58466, "*Trypanosoma cruzi* trypomastigote surface glycoprotein (TSA-1) mRNA, complete cds." Bethesda, MD [retrieved on Sep. 15, 2006]. Retrieved from the Internet: <URL:http://www.ncbi.nlm.nih.gov/entrez/viewer.fcgi?db=nucleotide&val=162314>; 3 pgs.

National Center for Biotechnology Information, National Library of Medicine, National Institutes of Health, GenBank Locus TCU74494, Accession No. U74494, "*Trypanosoma cruzi* surface protein-1 mRNA, complete cds". Bethesda, MD [retrieved on Sep. 15, 2006]. Retrieved from the Internet<URL:http://www.ncbi.nlm.nih.gov/entrez/viewer.fcgi?db=nucleotide&val=1658194>; 2 pgs.

National Center for Biotechnology Information, National Library of Medicine, National Institutes of Health, GenBank Locus TCU77951, Accession No. U77951, "*Trypanosoma cruzi* amastigote surface protein-2 (ASP-2) mRNA, partial cds". Bethesda, MD [retrieved on Sep. 15, 2006]. Retrieved from the Internet:<URL:http://www.ncbi.nlm.nih.gov/entrez/viewer.fcgi?db=nucleotide&val=1684906>; 2 pgs.

Nesvizhskii et al., "A Statiitical Model for Identifying Proteins by Tandem Mass Spectrometry," *Anal Chem*, 2003; 75:4646-4658.

Nielsen et al., "A Neural Network method for identification of prokaryotic and eukaryotic signal peptides and prediction of their cleavage sites," *Int J Neural Syst*, 1997; 8:581-599.

Paba et al., "Proteomic analysis of the human pathogen *Trypanosoma cruzi*," *Proteomics*, 2004; 4:1052-1059.

Paba et al., "Proteomic Analysis of *Trypanosoma cruzi* Developmental Stages Using Isotope-Coded Affinity Tag Reagents," *J Proteome Res*, 2004; 3:517-524.

Parodi-Talice et al., "Proteome analysis of the causative agent of Chagas disease: *Trypanosoma cruzi*," *Int J Parasitol*, 2004; 34:881-886.

Piras et al., "Changes in Morphology and Infectivity of Cell Culture-Derived Trypomastigotes of *Trypanosoma cruzi*," *Mol Biochem Parasitol*, 1982; 6:67-81.

Presta, "Antibody engineering," *Curr. Op. Struct. Biol.*, 1992; 2:593-596.

Resing et al., "Improving Reproducibility and Sensitivity in Identifying Human Proteins by Shotgun Proteomics," *Anal Chem*, 2004; 76:3556-3568.

Riechmann et al., "Reshaping human antibodies for therapy," *Nature*, 1988; 332:323-327.

Rondinelli et al., "*Trypanosoma cruzi*: An in Vitro Cycle of Cell Differentiation in Axenic Culture," *Exp Parasitol*, 1988; 66:197-204.

Santos et al., "The identification and molecular characterization of *Trypanosoma cruzi* amastigote surface protein-1, a member of the *trans*-sialidase gene super-family," *Mol. Biochem. Parasitol.* 1997; 86:1-11.

Schreier et al., *Hybridoma Techniques*, Cold Spring Harbor Laboratory, 1980. Title Page, Copyright Page and Table of Contents.

Schutze-Redelmeier et al., "Introduction of Exogenous Antigens into the MHC Class I Processing and Presentation Pathway by *Drosophila* Antennapedia Homeodomain Primes Cytotoxic T Cells in Vivo," *Journ. Immunol.*, 1996; 157:650-655.

Schwarze et al., "In Vivo Protein Transduction: Delivery of a Biologically Active Protein into the Mouse," *Science*, 1999; 285:1569-1572.

Strittmatter et al., "High Mass Measurement Accuracy Determination for Proteomics Using Multivariate Regression Fitting: Application to Electrospray Ionization Time-of-Flight Mass Spectrometry," *Anal Chem*, 2003; 75:460-468.

Tarleton, Rick L., "Vaccine Discovery for Chagas Disease," Grant Abstract, Grant No. 5P01AI044979-08. National Institute of Allergy and Infectious Diseases, project datess Sep. 1, 1999 to Feb. 28, 2009 [retrieved on Sep. 14, 2006]. Retrieved from the Internet<URL:http://crisp.cit.nih.gov/crisp/crisp_lib.query>; 2 pgs.

Thornton et al., "Not just for housekeeping: protein initiation and elongation factors in cell growth and tumorigenesis," *J Mol Med*, 2003; 81:536-548.

Tomlinson et al., "The induction of *Trypanosoma cruzi* trypomastigote to amastigote transformation by low pH," *Parasitology*, 1995; 110 (Pt 5):547-554.

Torres et al., "Characterization of an ABCA-like transporter involved in vesicular trafficking in the protozoan parasite *Trypanosoma cruzi*," *Mol Microbiol.*, 2004; 54:632-646.

TriTryp Genomes Meeting. Sep. 13-16, 2004. Seattle, Washington. Title Page, Acknowledgment Pages, and Program. 17 pages.

Verhoeyen et al., "Reshaping Human Antibodies: Grafting an Antilysozyme Activity," *Science*, 1988; 239:1534-1536.

Vickery, "The Histidine Content of the Hemoglobin of Man and of the Horse and Sheep, Determined with the Aid of 3,4-Dichlorobenzenesulfonic Acid," *J. Biol. Chem.*, 1942; 144:719-730.

Wang et al., "Induction of Antigen-Specific Cytotoxic T Lymphocytes in Humans by a Malaria DNA Vaccine," *Science*, 1998; 282:476-480.

Weatherly et al., "A Heuristic Method for Assigning a False-discovery Rate for Protein Indentifications from Mascot Database Search Results," *Mol Cell Proteomics*, 2005; 4:762-772.

Weatherly et al., "Use of Functional Genomics in Vaccine Discovery for *Trypanosoma cruzi*," TriTryp Genomes Meeting. Sep. 13-16, 2004. Seattle, Washington. Abstracts Cover Page, with Abstract p. 12.4.

Wilkinson et al., "*Trypanosoma cruzi* expresses a plant-like ascorbate-dependent hemoperoxidase localized to the endoplasmic reticulum," *Proc Natl Acad Sci U S A*, 2002; 99:13453-13458.

Williams, Researchers at University of Georgia provide first look at protein expression in Chagas Disease -causing parasites, Jul. 14, 2005, News Release. 3 pages.

Worthey et al., "*Leishmania major* chromosome 3 contains two long convergent polycistronic gene clusters separated by a tRNA gene," *Nucleic Acids Res*, 2003; 31:4201-4210.

Trujillo et al., "*Trypanosoma brucei* and *Trypanosoma cruzi* Tryparedoxin Peroxidases Catalytically Detoxify Peroxynitrite via Oxidation of Fast Reacting Thiols," *Journ. Of Biological Chemistry*, 2004. 279(33)34175-34182.

Balana-Fouce et al., "RNA interference in *Trypanosoma brucei*: a high-throughput engine for functional genomics in trypanosomatids?", 2007. *TRENDS in Parasitology*, 23(8):348-351.

Ullu et al., "RNA interference in protozoan parasites", 2004. *Cellular Microbiology*. 6(6):509-519.

DaRocha et al., "Tests of cytoplasmic RNA interference (RNAi) and construction of a tetracycline-inducible T7 promoter system in *Trypanosoma cruzi*", 2004. *Molecular & Biochemical Parasitology*. 133:175-186.

\* cited by examiner

Figure 5
Table 3: MS/MS sampling by life-cycle stage

Spectra collected: Total number of *T. cruzi* spectra for each life-cycle stage
Spectra matched: Total number of spectra that matched to peptides for each life-cycle stage using PROVALT to identify proteins
Unique peptides: Number of non-redundant peptides identified in the proteome for each life-cycle stage
Unique proteins: Assigned name of the gene in the TSK-TSC annotated genome

|                   | Epimastigote | Trypomastigote | Metacyclic | Amastigote | Total   |
|-------------------|--------------|----------------|------------|------------|---------|
| Spectra collected | 54149        | 20565          | 38979      | 25434      | 139,147 |
| Spectra matched   | 5857         | 2143           | 5737       | 3488       | 17,225  |
| Unique peptides   | 3456         | 1463           | 3202       | 1911       | 5792    |
| Unique proteins   | 1573         | 1194           | 2064       | 1576       | 2784    |

Table 4: Trypanosoma cruzi expressed proteins identified from TSK-TSC annotated genome

| Gene ID | Gene Name | Top BLAST Hit | Score | | | | |
|---|---|---|---|---|---|---|---|
| | | | Total | Amastigote | Trypomastigote | Metacyclic | Epimastigote |
| 6869.t00022 | histidine ammonia-lyase | gb\|AAO73411.1\| histidine ammonia lyase [Gallus gallus] | 1269 | 40 | 0 | 566 | 948 |
| 4823.t00003 | hypothetical protein, conserved | | 27 | 0 | 0 | 27 | 18 |
| 6931.t00010 | hypothetical protein, conserved | | 27 | 0 | 0 | 27 | 18 |
| 4935.t00028 | hypothetical protein, conserved | | 1019 | 121 | 232 | 834 | 381 |
| 8414.t00002 | 3-ketoacyl-CoA thiolase, putative | emb\|CAB55378.1\| possible 3-ketoacyl-CoA thiolase [Leishmania major] | 814 | 184 | 27 | 575 | 452 |
| 8107.t00003 | 3-ketoacyl-CoA thiolase, putative | emb\|CAB55378.1\| possible 3-ketoacyl-CoA thiolase [Leishmania major] | 741 | 168 | 27 | 511 | 379 |
| 4881.t00011 | urocanate hydratase | gb\|AAO50896.1\| similar to Mus musculus (Mouse). Probable urocanate hydratas | 789 | 0 | 0 | 266 | 720 |
| 5442.t00003 | hypothetical protein | | 677 | 84 | 217 | 642 | 0 |
| 7472.t00005 | hypothetical protein | | 677 | 84 | 217 | 642 | 0 |
| 7963.t00004 | calreticulin, putative | gb\|AAD22175.1\| calreticulin [Trypanosoma cruzi] | 445 | 167 | 294 | 58 | 126 |
| 5825.t00009 | carnitine/choline acetyltransferase, putative | ref\|NP_647756.1\| CG2107-PA [Drosophila melanogaster] gb\|AAF47698.1\| CG2107- | 400 | 196 | 18 | 200 | 106 |
| 4701.t00003 | carnitine/choline acetyltransferase, putative | ref\|NP_009420.1\| Outer carnitine acetyltransferase, mitochondrial; Yat1p | 75 | 0 | 0 | 75 | 0 |

Fig. 6a

| | | | | | | |
|---|---|---|---|---|---|---|
| 8180.t00009 | short chain 3-hydroxyacyl-coa dehydrogenase, putative | gb\|AAH56108.1\| Hadhsc-prov protein [Xenopus laevis] | 380 | 205 | 33 | 302 | 170 |
| 8307.t00024 | short chain 3-hydroxyacyl-coa dehydrogenase, putative | gb\|AAH56108.1\| Hadhsc-prov protein [Xenopus laevis] | 363 | 205 | 33 | 285 | 170 |
| 5802.t00004 | fumarate hydratase, putative | ref\|NP_824394.1\| putative fumarate hydratase class I [Streptomyces avermiti] | 361 | 199 | 0 | 262 | 0 |
| 7426.t00001 | fumarate hydratase, putative | ref\|NP_824394.1\| putative fumarate hydratase class I [Streptomyces avermiti] | 361 | 199 | 0 | 262 | 0 |
| 7164.t00019 | lipophosphoglycan biosynthetic protein, putative | gb\|AAM00390.1\| lipophosphoglycan biosynthetic protein [Leishmania donovani] | 345 | 140 | 218 | 74 | 132 |
| 4764.t00001 | lipophosphoglycan biosynthetic protein, putative | gb\|AAF67727.1\| glucose-regulated protein 94 [Leishmania infantum] | 91 | 22 | 69 | 0 | 0 |
| 8196.t00011 | hypothetical protein, conserved | gb\|AAN87460.1\| sulfate transporter [Heliobacillus mobilis] | 22 | 22 | 0 | 0 | 0 |
| 8148.t00011 | hypothetical protein, conserved | gb\|AAN87460.1\| sulfate transporter [Heliobacillus mobilis] | 22 | 22 | 0 | 0 | 0 |
| 6911.t00010 | hexose transporter, putative | gi\|453380\|gb\|AAA21207.1\| hexose transporter | 336 | 0 | 0 | 74 | 276 |
| 6911.t00001 | hexose transporter, putative | gi\|453380\|gb\|AAA21207.1\| hexose transporter | 336 | 0 | 0 | 74 | 276 |
| 7775.t00004 | hypothetical protein, to be annotated (newly added gene) | gi\|453380\|gb\|AAA21207.1\| hexose transporter | 336 | 0 | 0 | 74 | 276 |
| 8577.t00004 | hexose transporter, putative | gb\|AAA21207.1\| hexose transporter | 60 | 0 | 0 | 60 | 0 |
| 7775.t00003 | hexose transporter, putative | gb\|AAA21207.1\| hexose transporter | 28 | 0 | 0 | 28 | 0 |
| 7648.t00028 | hypothetical protein, to be annotated (newly added gene) | | 28 | 0 | 0 | 28 | 0 |
| 6963.t00002 | hypothetical protein, conserved | | 319 | 155 | 0 | 136 | 125 |
| 8649.t00005 | hypothetical protein, conserved | | 319 | 155 | 0 | 136 | 125 |
| 8197.t00006 | hypothetical protein, conserved | gb\|EAA48509.1\| hypothetical protein MG00167.4 [Magnaporthe grisea 70-15] | 275 | 147 | 0 | 224 | 0 |

Fig. 66

| | | | | | | |
|---|---|---|---|---|---|---|
| 4698.t00001 | aspartate aminotransferase, putative | gb\|AAK73815.1\| aspartate aminotransferase [Trypanosoma brucei] | 263 | 263 | 27 | 0 | 0 |
| 4779.t00007 | aspartate aminotransferase, putative | gb\|AAK73815.1\| aspartate aminotransferase [Trypanosoma brucei] | 150 | 150 | 27 | 0 | 0 |
| 8680.t00015 | thiolase protein-like protein, putative | ref\|NP_406263.1\| putative 3-ketoacyl-CoA thiolase [Yersinia pestis] ref\|NP | 261 | 132 | 0 | 226 | 14 |
| 10960.t00001 | thiolase protein-like protein, putative | ref\|XP_320688.1\| ENSANGP00000020177 [Anopheles gambiae] gb\|EAA00331.1\| ENSA | 146 | 17 | 0 | 146 | 0 |
| 8174.t00001 | trifunctional enzyme alpha subunit, mitochondrial precursor-like protein, putative | ref\|NP_760849.1\| Fatty oxidation complex, alpha subunit [Vibrio vulnificus | 256 | 0 | 0 | 232 | 68 |
| 7949.t00004 | hypothetical protein, to be annotated (newly added gene) | gi\|42523232\|ref\|NP_968701.1\| fatty oxidation complex, alpha subunit [Bdello] | 232 | 0 | 0 | 232 | 44 |
| 6996.t00047 | ribosomal protein L35A, putative | ref\|NP_649539.1\| CG2099-PA [Drosophila melanogaster] gb\|AAF52027.1\| CG2099- | 255 | 16 | 87 | 0 | 194 |
| 6870.t00001 | hypothetical protein, conserved | | 16 | 0 | 0 | 0 | 16 |
| 7649.t00001 | hypothetical protein, conserved | | 16 | 0 | 0 | 0 | 16 |
| 8565.t00006 | hypothetical protein | ref\|NP_295683.1\| acetyl-CoA acetyltransferase [Deinococcus radiodurans] pir | 247 | 68 | 0 | 247 | 62 |
| 8016.t00012 | acyl-coenzyme a dehydrogenase, putative | gb\|AAH45911.1\| Similar to acyl-Coenzyme A dehydrogenase, C-4 to C-12 straig | 171 | 105 | 0 | 167 | 0 |
| 8359.t00029 | acyl-coenzyme a dehydrogenase, putative | gb\|AAH45911.1\| Similar to acyl-Coenzyme A dehydrogenase, C-4 to C-12 straig | 171 | 105 | 0 | 167 | 0 |
| 7547.t00002 | arginase, putative | ref\|ZP_00019275.1\| hypothetical protein [Chloroflexus aurantiacus] | 167 | 0 | 0 | 144 | 50 |
| 5428.t00009 | arginase, putative | ref\|ZP_00019275.1\| hypothetical protein [Chloroflexus aurantiacus] | 167 | 0 | 0 | 144 | 50 |
| 5150.t00008 | oligosaccharyl transferase subunit, putative | emb\|CAB61569.1\| hypothetical STT3 ortholog [Leishmania major] | 155 | 107 | 0 | 74 | 40 |

Fig. 6c

| | | | | | | |
|---|---|---|---|---|---|---|
| 4592.t00003 | oligosaccharyl transferase subunit, putative | emb|CAB61569.1| hypothetical STT3 ortholog [Leishmania major] | 135 | 77 | 0 | 58 | 40 |
| 5758.t00003 | proteasome regulatory non-ATP-ase subunit 8, putative | gb|AAL72631.1| proteasome regulatory non-ATP-ase subunit 8 [Trypanosoma bru] | 159 | 41 | 0 | 79 | 39 |
| 6089.t00009 | proteasome regulatory non-ATP-ase subunit 8, putative | gb|AAL72631.1| proteasome regulatory non-ATP-ase subunit 8 [Trypanosoma bru] | 159 | 41 | 0 | 79 | 39 |
| 6290.t00010 | guanine deaminase, putative | ref|NP_816079.1| chlorohydrolase family protein [Enterococcus faecalis V583] | 158 | 111 | 70 | 0 | 0 |
| 7541.t00015 | guanine deaminase, putative | ref|NP_816079.1| chlorohydrolase family protein [Enterococcus faecalis V583] | 126 | 111 | 38 | 0 | 0 |
| 4947.t00002 | fatty acyl CoA synthetase 2, putative | gb|AAF19439.1| fatty acyl CoA synthetase 3 [Trypanosoma brucei] | 139 | 139 | 0 | 15 | 0 |
| 4947.t00001 | fatty acyl CoA synthetase 2, putative | gb|AAF19438.1| fatty acyl CoA synthetase 2 [Trypanosoma brucei] | 71 | 71 | 0 | 0 | 0 |
| 6156.t00001 | fatty acyl CoA synthetase 2, putative | gb|AAF19438.1| fatty acyl CoA synthetase 2 [Trypanosoma brucei] | 71 | 71 | 0 | 0 | 0 |
| 7108.t00011 | fatty acyl CoA synthetase 2 | gb|AAF19438.1| fatty acyl CoA synthetase 2 [Trypanosoma brucei] | 22 | 22 | 0 | 0 | 0 |
| 4492.t00001 | fatty acyl CoA synthetase 2-related | gb|AAF19438.1| fatty acyl CoA synthetase 2 [Trypanosoma brucei] | 22 | 22 | 0 | 0 | 0 |
| 7070.t00010 | enoyl-CoA hydratase/isomerase family protein, putative | ref|NP_650453.3| CG5044-PA [Drosophila melanogaster] gb|AAK93433.1| LD47223 | 120 | 120 | 31 | 0 | 0 |
| 6142.t00016 | enoyl-CoA hydratase/isomerase family protein, putative | ref|NP_650453.3| CG5044-PA [Drosophila melanogaster] gb|AAK93433.1| LD47223 | 71 | 71 | 31 | 0 | 0 |
| 6142.t00017 | LD47223p | gi|28571729|ref|NP_650453.3| CG5044-PA [Drosophila melanogaster] gi|1529232 | 49 | 49 | 0 | 0 | 0 |
| 7070.t00009 | hypothetical protein | ref|NP_650453.3| CG5044-PA [Drosophila melanogaster] gb|AAK93433.1| LD47223 | 49 | 49 | 0 | 0 | 0 |
| 7979.t00003 | dTDP-glucose 4,6-dehydratase | ref|NP_681454.1| dTDP-glucose 4,6-dehydratase [Thermosynechococcus elongatu | 110 | 70 | 107 | 0 | 0 |

Fig. 6d

| | | | | | | |
|---|---|---|---|---|---|---|
| 8257.t00038 | dTDP-glucose 4,6-dehydratase | ref|NP_926719.1| dTDP-glucose 4-6-dehydratase [Gloeobacter violaceus] dbjB | 110 | 70 | 107 | 0 |
| 6875.t00001 | fatty acyl CoA synthetase 2, putative | gb|AAF19438.1| fatty acyl CoA synthetase 2 [Trypanosoma brucei] | 106 | 71 | 0 | 35 |
| 4646.t00005 | fatty acyl CoA synthetase, putative | ref|NP_859450.1| long chain fatty acyl CoA synthetase 6 [Leishmania major] | 103 | 22 | 0 | 81 |
| 8550.t00024 | hypothetical protein, to be annotated (newly added gene) | gi|47600918|emb|CAG29795.1| Acyl-CoA synthetase 5 [Trypanosoma brucei] | 103 | 22 | 0 | 81 |
| 8251.t00016 | hypothetical protein, conserved | emb|CAB94022.2| possible protein kinase inhibitor [Leishmania major] | 92 | 15 | 77 | 0 |
| 5914.t00008 | hypothetical protein, conserved | emb|CAB94022.2| possible protein kinase inhibitor [Leishmania major] | 92 | 15 | 77 | 0 | 24 |
| 8364.t00027 | fumarate hydratase, putative | ref|NP_458599.1| fumarate hydratase class I [Salmonella enterica subsp. Ent | 87 | 50 | 0 | 37 |
| 7271.t00006 | fumarate hydratase, putative | ref|NP_458599.1| fumarate hydratase class I [Salmonella enterica subsp. Ent | 87 | 50 | 0 | 37 |
| 7377.t00003 | casein kinase, putative | gb|AAF80492.1| casein kinase 1 homolog 1 [Trypanosoma cruzi] gb|AAK58697.1| | 76 | 59 | 49 | 76 |
| 7770.t00022 | casein kinase, putative | gb|AAF80492.1| casein kinase 1 homolog 1 [Trypanosoma cruzi] gb|AAK58697.1| | 76 | 59 | 49 | 76 |
| 7292.t00003 | casein kinase, putative | gb|AAF00025.1| casein kinase 1 homolog 2 [Trypanosoma cruzi] gb|AAK58696.1| | 76 | 59 | 49 | 76 |
| 7770.t00024 | casein kinase, putative | gb|AAF00025.1| casein kinase 1 homolog 2 [Trypanosoma cruzi] gb|AAK58696.1| | 76 | 59 | 49 | 76 |
| 6443.t00001 | casein kinase, delta isoform, putative | gb|AAF00025.1| casein kinase 1 homolog 2 [Trypanosoma cruzi] gb|AAK58696.1| | 76 | 59 | 49 | 76 |
| 7377.t00004 | casein kinase, putative | gb|AAF00025.1| casein kinase 1 homolog 2 [Trypanosoma cruzi] gb|AAK58696.1| | 76 | 59 | 49 | 76 |

*Fig. 6e*

| | | | | | |
|---|---|---|---|---|---|
| 7292.t00002 | casein kinase, putative | gb\|AAF00025.1\| casein kinase 1 homolog 2 [Trypanosoma cruzi] gb\|AAK58696.1\| | 76 | 59 | 49 | 76 | 0 |
| 7770.t00023 | casein kinase, putative | gb\|AAF00025.1\| casein kinase 1 homolog 2 [Trypanosoma cruzi] gb\|AAK58696.1\| | 76 | 59 | 49 | 76 | 0 |
| 8792.t00035 | hypothetical protein, to be annotated (newly added gene) | gi\|6978705\|ref\|NP_037062.1\| carnitine palmitoyltransferase 2 [Rattus norveg] | 64 | 0 | 0 | 64 | 0 |
| 6191.t00005 | hypothetical protein, conserved | gb\|AAH43884.1\| 2e999-prov protein [Xenopus laevis] | 63 | 63 | 0 | 0 | 0 |
| 8726.t00010 | protein transport protein Sec23, putative | ref\|XP_321324.1\| ENSANGP00000012825 [Anopheles gambiae] gb\|EAA01238.1\| ENSA | 60 | 60 | 0 | 20 | 0 |
| 6853.t00015 | polyprenyl synthase, putative | emb\|CAB75644.1\| possible geranylgeranyl diphosphate synthase [Leishmania ma] | 56 | 56 | 0 | 0 | 0 |
| 8647.t00008 | polyprenyl synthase, putative | emb\|CAB75644.1\| possible geranylgeranyl diphosphate synthase [Leishmania ma] | 56 | 56 | 0 | 0 | 0 |
| 7204.t00017 | hypothetical protein, conserved | | 55 | 55 | 0 | 41 | 0 |
| 7069.t00002 | hypothetical protein, conserved | | 55 | 55 | 0 | 41 | 0 |
| 4653.t00001 | mannose-1-phosphate guanyltransferase, putative | emb\|CAB58292.1\| mannose-1-phosphate guanyltransferase [Leishmania major] | 51 | 51 | 0 | 0 | 0 |
| 8551.t00001 | mannose-1-phosphate guanyltransferase, putative | emb\|CAB58292.1\| mannose-1-phosphate guanyltransferase [Leishmania major] | 51 | 51 | 0 | 0 | 0 |
| 8196.t00010 | hypothetical protein, conserved | pir\|\|T46723 hypothetical protein L4326.12 [imported] - Leishmania major emb | 49 | 49 | 0 | 0 | 0 |
| 8148.t00010 | hypothetical protein, conserved | pir\|\|T46723 hypothetical protein L4326.12 [imported] - Leishmania major emb | 49 | 49 | 0 | 0 | 0 |
| 8644.t00006 | hypothetical protein, conserved | gb\|AAB18921.1\| ModA [Dictyostelium discoideum] | 46 | 0 | 0 | 0 | 46 |

*Fig. 6f*

| 7561.t00026 | hypothetical protein, conserved | gb\|AAB18921.1\| ModA [Dictyostelium discoideum] | 46 | | | 46 |
|---|---|---|---|---|---|---|
| 6494.t00003 | possible carnitine o-palmitoyltransferase | emb\|CAB94115.2\| possible carnitine o-palmitoyltransferase [Leishmania major] | 44 | 44 | 0 | 0 |
| 8669.t00009 | hypothetical protein, to be annotated (newly added gene) | gi\|11877279\|emb\|CAB94115.2\| possible carnitine o-palmitoyltransferase [Leis] | 44 | 44 | 0 | 0 |
| 7804.t00004 | possible carnitine o-palmitoyltransferase | emb\|CAB94115.2\| possible carnitine o-palmitoyltransferase [Leishmania major] | 44 | 44 | 0 | 0 |
| 8652.t00008 | choline/Carnitine o-acyltransferase-like, putative | emb\|CAB94115.2\| possible carnitine o-palmitoyltransferase [Leishmania major] | 44 | 44 | 0 | 0 |
| 7293.t00002 | hypothetical protein | emb\|CAB94115.2\| possible carnitine o-palmitoyltransferase [Leishmania major] | 44 | 44 | 0 | 0 |

Fig. 6g

| Fig. 7a |
|---|
| Fig. 7b |
| Fig. 7c |
| Fig. 7d |
| Fig. 7e |
| Fig. 7f |
| Fig. 7g |

*Fig. 7*

Figure 7
Table 5: Selected stage-regulated *Trypanosoma cruzi* proteins

Protein Group: ID of proteins which share a set (or subset) of peptides
Source: TOP indicates the protein is top-scoring in protein group, OTHER indicates the protein was identified by a subset (or all) of the
Gene ID: Assigned ID of the gene in the TSK-TSC annotated genome
Gene Name: Assigned name of the gene in the TSK-TSC annotated genome
Top BLAST Hit: Summary of top NR BLAST hit
Total Score: Sum of ion scores of non-redundant peptides identified in all life-cycle stages
Amastigote Score: Sum of ion scores of non-redundant peptides identified from Amastigote life-cycle stage
Trypomastigote Score: Sum of ion scores of non-redundant peptides identified from Trypomastigote life-cycle stage
Metacyclic Score: Sum of ion scores of non-redundant peptides identified from Metacyclic life-cycle stage
Epimastigote Score: Sum of ion scores of non-redundant peptides identified from Epimastigote life-cycle stage

| Protein Group | Source | Gene ID | Gene Name | Top BLAST Hit | Total Score | Amastigote Score | Trypomastigote Score | Metacyclic Score | Epimastigote Score |
|---|---|---|---|---|---|---|---|---|---|
| lipid metabolism | | | | | | | | | |
| 685 | TOP | 4947.t00002 | fatty acyl CoA synthetase 2, putative | gb|AAP19433.1| fatty acyl CoA synthetase 2 [Trypanosoma brucei] (SCORE:2333, EVAL:0.0, % IDS:61.7, % SEQ COV:99.9) | 88 | 88 | 0 | 0 | 0 |
| 759 | TOP | 7070.t00010 | enoyl-CoA hydratase/isomerase family protein, putative | ref|NP_564453.3| CG5844-PA [Drosophila melanogaster] gb|AAK93433.1| LD47223 (SCORE:540, EVAL:7e-54, % IDS:38.9, % SEQ COV:96) | 120 | 120 | 0 | 0 | 0 |
| 600 | TOP | 7005.t00012 | sterol C-24 reductase, putative | ref|NP_820251.1| C-24(28) sterol reductase, putative [Coxiella burnetii RSA] (SCORE:357, EVAL:1e-102, % IDS:<1.5, % SEQ COV:91.8) | 168 | 104 | 0 | 0 | 168 |
| 1016 | TOP | 8647.t00008 | polyprenyl synthase, putative | emb|CAB75444.1| possible geranylgeranyl diphosphate synthase [Leishmania ma] (SCORE:450, EVAL:1e-159, % IDS:41.6, % SEQ COV:95.9) | 56 | 56 | 0 | 0 | 0 |
| 586 | TOP | 8359.t00029 | acyl-coenzyme a dehydrogenase, putative | gb|AAH58911.1| similar to acyl Coenzyme A dehydrogenase, C-4 to C-12 straig (SCORE:1314, EVAL:1e-143, % IDS:63.2, % SEQ COV:96.5) | 141 | 105 | 0 | 137 | 0 |
| 829 | TOP | 1688.t00001 | hypothetical protein, to be annotated (newly added gene) | gb|EAN82815.1| delta-9 fatty acid desaturase [Cyanidioschyzon m (SCORE:144, EVAL:1e-08, % IDS:30.4, % SEQ COV:82.1) | 97 | 0 | 0 | 0 | 97 |
| 1142 | TOP | 8652.t00008 | choline/Carnitine o-acyltransferase-like, putative | emb|CAB97115.2| possible carnitine o-palmitoyltransferase [Leishmania major] (SCORE:567, EVAL:1e-91, % IDS:36, % SEQ COV:95.9) | 44 | 44 | 0 | 0 | 0 |
| carbohydrate | | | | | | | | | |
| 109 | TOP | 8310.t00002 | hexokinase | emb|CAC85631.1| hexokinase 1 [Trypanosoma cruzi] gb|AAL33565.1| hexokinase I (SCORE:2465, EVAL:0.0, % IDS:99.3, % SEQ COV:100) | 649 | 166 | 0 | 367 | 514 |
| 116 | TOP | 7939.t00002 | hexokinase | emb|CAC85631.1| hexokinase 1 [Trypanosoma cruzi] gb|AAL33565.1| hexokinase I (SCORE:2375, EVAL:0.0, % IDS:99.3, % SEQ COV:100) | 670 | 166 | 0 | 441 | 461 |
| 240 | TOP | 5956.t00007 | 6-phosphogluconate dehydrogenase, decarboxylating, putative | gb|AAB82499.1| 6-phosphogluconate dehydrogenase (decarboxylating) [EC 1.1.1.44] (SCORE:1897, EVAL:0.0, % IDS:73.9, % SEQ COV:100) | 355 | 98 | 36 | 356 | 0 |
| 669 | TOP | 7143.t00048 | ribokinase, putative | ref|NP_934619.1| ribokinase [Vibrio vulnificus] gb|AAO07121.1| ribokinase [Vibrio vulnifi (SCORE:177, EVAL:1e-46, % IDS:38.9, % SEQ COV:93.3) | 112 | 0 | 0 | 0 | 112 |
| amino acid | | | | | | | | | |
| 49 | TOP | 6869.t00022 | histidine ammonia-lyase | gb|AAO73411.1| histidine ammonia lyase [Gallus gallus] (SCORE:1465, EVAL:1e-161, % IDS:57.5, % SEQ COV:96.4) | 1032 | 40 | 0 | 456 | 693 |
| 102 | TOP | 4881.t00011 | urocanate hydratase | gb|AAC59035.1| similar to Mus musculus (Mouse). Probable urocanate hydratase (SCORE:1956, EVAL:0.0, % IDS:57.6, % SEQ COV:99.1) | 634 | 0 | 0 | 211 | 592 |
| 274 | TOP | 8774.t00012 | L-threonine 3-dehydrogenase, putative | gb|AAC09225.1| L-threonine 3-dehydrogenase [Trypanosoma brucei] (SCORE:1272, EVAL:1e-139, % IDS:71.6, % SEQ COV:100) | 244 | 205 | 123 | 0 | 91 |
| 511 | TOP | 7625.t00037 | glutamine synthetase, putative | gb|AAR31763.1| glutamine synthetase [Phytophthora infestans] (SCORE:835, EVAL:5e-88, % IDS:48.5, % SEQ COV:79.5) | 115 | 35 | 0 | 0 | 80 |
| 277 | TOP | 7985.t00007 | pyrroline-5-carboxylate synthetase-like protein, putative | ref|NP_181202.2| delta 1 pyrroline 5-carboxylate synthase B (P5CS B) [F=C] (SCORE:922, EVAL:5e-93, % IDS:46.9, % SEQ COV:90.5) | 308 | 0 | 116 | 242 | 0 |
| 30 | TOP | 5907.t00001 | cystathionine beta-synthase, putative | gb|AAK36197.1| cystathionine beta-synthase 1 [Trypanosoma cruzi] gb|AAK16039 (SCORE:1971, EVAL:0.0, % IDS:97.9, % SEQ COV:89.9) | 1398 | 618 | 129 | 416 | 1096 |
| 402 | TOP | 4698.t00001 | aspartate aminotransferase, putative | gb|AAR23615.1| aspartate aminotransferase [Trypanosoma brucei] (SCORE:1331, EVAL:1e-145, % IDS:61.5, % SEQ COV:89) | 201 | 201 | 0 | 0 | 0 |
| 183 | TOP | 7944.t00004 | acetylornithine deacetylase-like, putative | (SCORE:759, EVAL:4e-73, % IDS:40.6, % SEQ COV:97.2) | 434 | 36 | 0 | 317 | 235 |

*Fig. 7a*

Fig. 76

| | | | | | | | |
|---|---|---|---|---|---|---|---|
| 933 TOP | 5883.t00003 | MP18 RNA editing complex protein | gb|AAH10635.1| MP18 [Trypanosoma cruzi] (SCORE:846, EVAL:5e-90, %IDS:99.3, %SEQ COV:100) | 59 | 0 | 0 | 0 | 69 |
| 186 TOP | 7093.t00008 | seryl-tRNA synthetase, putative | sp|P26330|SYS_MOUSE Seryl-tRNA synthetase (Serine–tRNA ligase) (SerRS) (gb) (SCORE:1201, EVAL:1e-130, %IDS:50, %SEQ COV:100) | 350 | 0 | 42 | 308 | 0 |
| 252 TOP | 6054.t00001 | seryl-tRNA synthetase, putative | gb|O819B9|SYS_HELAN SERYL-TRNA SYNTHETASE (SERINE–TRNA LIGASE) (SERRS) pir (SCORE:644, EVAL:3e-66, %IDS:60.1, %SEQ COV:95.3) | 299 | 0 | 42 | 257 | 0 |
| 280 TOP | 5658.t00005 | methionyl-tRNA synthetase, putative | emb|CAB82611.1| methionyl-tRNA synthetase [Leishmania major] (SCORE:2369, EVAL:0.0, %IDS:59.4, %SEQ COV:99) | 309 | 0 | 0 | 309 | 0 |
| 998 TOP | 8312.t00001 | pumilio protein, putative | gb|AAG34134.1| pumilio protein 1 [Trypanosoma cruzi] (SCORE:3891, EVAL:0.0, %IDS:90.5, %SEQ COV:100) | 58 | 0 | 58 | 0 | 0 |
| 1118 TOP | 16099.t00002 | NLI-interacting factor, putative | ref|NF_393212.1| similarity to HYPOTHETICAL PROTEIN YA22_SCHPO [Encephalito... (SCORE:164, EVAL:1e-12, %IDS:27.8, %SEQ COV:52.3) | 46 | 0 | 46 | 0 | 0 |
| 261 TOP | 6039.t00012 | ATP-dependent RNA helicase, putative | dbj|BAC83034.1| putative DEADbox RNA helicase DEAD3 [Oryza sativa (japonica cult... (SCORE:1139, EVAL:1e-123, %IDS:56.2, %SEQ COV:54.3) | 217 | 56 | 97 | 0 | 217 |
| 901 TOP | 7413.t00001 | poly-zinc finger protein 2 | gb|AAL29186.1| poly-zinc finger protein 2 [Trypanosoma cruzi] (SCORE:1097, EVAL:1e-119, %IDS:89.4, %SEQ COV:100) | 77 | 0 | 0 | 0 | 77 |
| 980 TOP | 7057.t00003 | RNA-binding protein TcRBP6 | gb|AAL74214.1| RNA-binding protein [Trypanosoma cruzi] (SCORE:473, EVAL:4e-91, %IDS:97.7, %SEQ COV:52) | 61 | 61 | 0 | 0 | 0 | vesicular/protein trafficking

| | | | | | | | |
|---|---|---|---|---|---|---|---|
| 1155 TOP | 6673.t00017 | vacuolar protein sorting-associated protein 35, putative | emb|CAG14530.1| possible vacuolar sorting protein [Leishmania major] (SCORE:1569, EVAL:0.0, %IDS:39.2, %SEQ COV:100) | 43 | 0 | 43 | 0 | 0 |
| 563 TOP | 6172.t00013 | vesicle-associated membrane protein, putative | gb|AAP61257.1| synaptobrevin-like protein [Entamoeba histolytica] (SCORE:357, EVAL:5e-91, %IDS:89.3, %SEQ COV:87) | 177 | 78 | 83 | 0 | 105 |
| 185 TOP | 8142.t00001 | dynein heavy chain, putative | emb|CAD04266.1| possible dynein heavy chain alpha [Leishmania major] (SCORE:1042, EVAL:0.0, %IDS:79.2, %SEQ COV:73.9) | 327 | 43 | 90 | 273 | 0 |
| 576 TOP | 4703.t00005 | hypothetical protein, to be annotated (newly added gene) | gi|18774070|emb|CAC68211.1| rab1 [Trypanosoma brucei] (SCORE:318, EVAL:1e-37, %IDS:79.4, %SEQ COV:65.8) | 89 | 89 | 0 | 0 | 0 |
| 1038 TOP | 8208.t00006 | ras-related protein rab-5, putative | gb|AAC46991.1| ras-related protein RAB-5 [Trypanosoma cruzi] (SCORE:721, EVAL:1e-75, %IDS:63.9, %SEQ COV:100) | 54 | 0 | 54 | 0 | 0 |
| 906 TOP | 8725.t00010 | protein transport protein Sec23, putative | ref|XP_321324.1| ENSANGP00000012825 [Anopheles gambiae] gb|EAA01238.1| ENSA... (SCORE:1149, EVAL:1e-124, %IDS:33.9, %SEQ COV:92.2) | 60 | 60 | 0 | 0 | 0 |
| 823 TOP | 6930.t00029 | protein transport protein sec31, putative | dbj|BAD47154.1| Sec31p [Oryza sativa] dbj|BAC83946.1| Sec31p [Oryza sativa (SCORE:680, EVAL:3e-60, %IDS:26.7, %SEQ COV:45.6) | 39 | 39 | 0 | 0 | 77 |
| 487 TOP | 6855.t00003 | lectin, putative | gb|AAC46061.1| galactin-3 [Trypanosoma cruzi] (SCORE:1510, EVAL:1e-177, %IDS:94.9, %SEQ COV:57.3) | 221 | 35 | 221 | 0 | 0 | signal transduction

| | | | | | | | |
|---|---|---|---|---|---|---|---|
| 670 TOP | 7739.t00038 | calmodulin-like protein | prf|1835203A calmodulin 1 (SCORE:259, EVAL:6e-21, %IDS:41.1, %SEQ COV:81.9) | 116 | 0 | 0 | 0 | 116 |
| 89 TOP | 6860.t00015 | protein kinase A regulatory subunit, putative | gb|AAC03766.1| protein kinase A regulatory subunit [Trypanosoma cruzi] (SCORE:2377, EVAL:0.0, %IDS:92.4, %SEQ COV:100) | 791 | 168 | 263 | 715 | 0 |
| 351 TOP | 8443.t00008 | protein tyrosine phosphatase-like protein, putative | ref|NP_033012.2| protein tyrosine phosphatase 4a3 [Mus musculus] ref|XP_343... (SCORE:318, EVAL:1e-28, %IDS:46, %SEQ COV:83.3) | 205 | 0 | 0 | 205 | 0 |
| 841 TOP | 7518.t00003 | serine/threonine-protein kinase A, putative | sp|Q06942|KKIA_TRYBB Putative serine/threonine-protein kinase A pir||T48411... (SCORE:850, EVAL:3e-90, %IDS:40, %SEQ COV:31.9) | 94 | 58 | 36 | 0 | 0 | protein folding/chaperons

| | | | | | | | |
|---|---|---|---|---|---|---|---|
| 532 TOP | 7919.t00011 | FKBP-type peptidyl-prolyl cis-trans isomerase, conserved | sp|Q9N734|MIP_TRYCR Macrophage infectivity potentiator precursor (Peptidyl-... (SCORE:1024, EVAL:1e-110, %IDS:99.4, %SEQ COV:100) | 166 | 45 | 121 | 0 | 0 |
| 413 TOP | 8652.t00007 | peptidylprolyl isomerase-like | emb|CAB94114.1| peptidylprolyl isomerase/nima cyclophilin [Leishmania major] (SCORE:690, EVAL:1e-106, %IDS:90.3, %SEQ COV:87.9) | 229 | 140 | 84 | 56 | 56 |
| 379 TOP | 8668.t00001 | peptidylprolyl isomerase-like | emb|CAB94114.1| peptidylprolyl isomerase/nima cyclophilin [Leishmania major] (SCORE:595, EVAL:1e-106, %IDS:49.8, %SEQ COV:91) | 249 | 160 | 84 | 56 | 0 |
| 384 TOP | 5730.t00001 | protein disulfide isomerase, putative | ref|NP_910169.1| putative disulfide-isomerase precursor [Oryza sativa] gb|A (SCORE:377, EVAL:2e-35, %IDS:37.5, %SEQ COV:98.1) | 235 | 100 | 195 | 0 | 59 |
| 475 TOP | 7639.t00014 | protein disulfide isomerase, putative | ref|NP_182263.1| protein disulfide isomerase family [Arabidopsis thaliana] (SCORE:678, EVAL:2e-35, %IDS:37.5, %SEQ COV:98.1) | 121 | 0 | 121 | 0 | 0 |
| 231 TOP | 8141.t00001 | chaperonin TCP20, putative | gb|AAG35862.1| chaperonin TCP20 [Leishmania donovani] (SCORE:1933, EVAL:0.0, %IDS:72, %SEQ COV:97.4) | 339 | 0 | 172 | 0 | 167 |
| 1039 TOP | 8320.t00007 | HSP70-like protein | gb|AAD47086.1| ORF H60hrp1 L3f93.5 [Leishmania major] prf|1028948 hsp70-rel (SCORE:647, EVAL:9e-66, %IDS:30.9, %SEQ COV:67.3) | 53 | 0 | 53 | 0 | 0 |
| 244 TOP | 7951.t00010 | ATP-dependent Clp protease subunit, heat shock protein 78 (HSP78), putative | ref|XP_340401.1| mitochondrial heat shock protein 78, putative [Trypanosoma cruzi] (SCORE:3119, EVAL:0.0, %IDS:81.2, %SEQ COV:95.5) | 342 | 248 | 0 | 143 | 66 |

*Fig. 7c*

| ID | Accession | Description | Annotation | V1 | V2 | V3 | V4 |
|---|---|---|---|---|---|---|---|
| 541 TOP | 8007.t00002 | ATP-dependent Clp protease subunit, heat shock protein 78 (HSP78), putative | ref|XP_364401.1| mitochondrial heat shock protein 78, putative [Trypanosoma] (SCORE:1287, EVAL:1e-140, % IDS:78.8, % SEQ COV:99.1) | 133 | 138 | 0 | 49 | 65 |
| 207 TOP | 7105.t00002 | ATP-dependent Clp protease subunit, heat shock protein 100 (HSP100), putative | ref|XP_340596.1| heat shock protein 100 [Trypanosoma brucei] gb|AAC16055.1| (SCORE2089, EVAL:0.0, % IDS:70.5, % SEQ COV:100) | 410 | 113 | 0 | 349 | 48 |
| 325 TOP | 6535.t00001 | dnaK protein | pir|(S7150B chank-type molecular chaperone hsp70,4 - Leishmania major amt|CAC16035.25, EVAL:3e-79, % IDS:74.3, % SEQ COV:82.3) | 209 | 150 | 0 | 39 | 55 |
| 167 TOP | 4935.t00031 | heat shock protein, putative | gb|AAX69515.1| similar to 0 trypanosome cDOccidium [saline moq... TNF recept (SCORE:1395, EVAL:1e-153, % IDS:43.7, % SEQ COV:55.1) | 470 | 152 | 0 | 53 | 300 | antioxidant/detoxification

| ID | Accession | Description | Annotation | V1 | V2 | V3 | V4 | V5 |
|---|---|---|---|---|---|---|---|---|
| 22 TOP | 8031.t00007 | thiol-dependent reductase 1, putative | gb|AAZ1419.1| c4c2_prf|0193s3A glutathione S transferase (SCORE:2187, EVAL:0.0, % IDS:92.8, % SEQ COV:100) | 1508 | 0 | 0 | 1414 | 227 |
| 47 TOP | 4568.t00003 | thiol-dependent reductase 1, putative | gb|AAZ1419.1| c4c2_prf|0193s3A glutathione S transferase (SCORE:2269, EVAL:0.0, % IDS:99.4, % SEQ COV:100) | 1052 | 0 | 0 | 916 | 179 |
| 152 TOP | 6946.t00006 | ascorbate-dependent peroxidase | emb|CAJ30023.1| ascorbate-dependent peroxidase [Trypanosoma cruzi] (SCORE:1655, EVAL:0.0, % IDS:93.5, % SEQ COV:100) | 477 | 46 | 0 | 477 | 0 |
| 59 TOP | 7272.t00001 | tryparedoxin peroxidase | emb|CAJ08522.1| tryparedoxin peroxidase homologue [Trypanosoma cruzi] gb|AA (SCORE:1068, EVAL:1e-115, % IDS:99.4, % SEQ COV:100) | 895 | 609 | 97 | 545 | 528 |
| 67 TOP | 4403.t00001 | tryparedoxin peroxidase | emb|CAJ08522.1| tryparedoxin peroxidase homologue [Trypanosoma cruzi] gb|AA (SCORE:1072, EVAL:1e-116, % IDS:100, % SEQ COV:100) | 850 | 446 | 97 | 567 | 371 |
| 159 TOP | 8115.t00003 | hypothetical protein, to be annotated (newly added gene) | gi|4396829|emb|AAD8923.1| peroxiredoxin [Trypanosoma cruzi] (SCORE:1170, EVAL:1e-127, % IDS:93.5, % SEQ COV:100) | 565 | 369 | 266 | 289 | 0 |
| 762 TOP | 8070.t00009 | tryparedoxin synthetase, putative | gb|AAG15408.1| tryparedoxin synthetase [Trypanosoma cruzi] (SCORE:3416, EVAL:0.0, % IDS:81, % SEQ COV:100) | 119 | 0 | 0 | 119 | 0 |
| 563 TOP | 7898.t00005 | tryparedoxin synthetase, putative | gb|AAG15408.1| tryparedoxin synthetase [Trypanosoma cruzi] (SCORE:3488, EVAL:0.0, % IDS:100, % SEQ COV:100) | 173 | 0 | 0 | 173 | 0 |
| 796 TOP | 5824.t00003 | tryparedoxin | emb|CAC35918.1| tryparedoxin [Trypanosoma cruzi] (SCORE:754, EVAL:1e-79, % IDS:99.3, % SEQ COV:100) | 108 | 0 | 37 | 108 | 0 |
| 268 TOP | 4636.t00003 | trypanothione reductase, putative | sp|P28593|TYTR_TRYCR trypanothione reductase (TR) (N)(N)(6)-bis(glutathion (SCORE:2529, EVAL:0.0, % IDS:99.1, % SEQ COV:100) | 215 | 0 | 0 | 70 | 190 |
| 156 TOP | 5781.t00004 | iron superoxide dismutase, putative | gb|AAG15412.1| iron superoxide dismutase A [Trypanosoma cruzi] (SCORE:967, EVAL:1e-106, % IDS:98.4, % SEQ COV:81.1) | 513 | 47 | 0 | 513 | 0 |
| 246 TOP | 7897.t00001 | membrane-bound acid phosphatase, putative | | 379 | 49 | 0 | 370 | 0 | proteolysis and peptidolysis

| ID | Accession | Description | Annotation | V1 | V2 | V3 | V4 | V5 |
|---|---|---|---|---|---|---|---|---|
| 65 TOP | 6616.t00005 | mitochondrial processing peptidase, beta subunit, putative | ref|XP_321316.1| ENSANGP00000012647 [Anopheles gambiae] gb|EAA01226.1| ENSA (SCORE:577, EVAL:6e-53, % IDS:31, % SEQ COV:94.1) | 1035 | 189 | 41 | 867 | 175 |
| 1042 TOP | 6939.t00001 | serine carboxypeptidase S28, putative | ref|NP_497399.1| expressed protein [Arabidopsis thaliana] gb|AAK59665.1| un (SCORE:452, EVAL:2e-43, % IDS:30.1, % SEQ COV:69.9) | 53 | 0 | 53 | 0 | 0 |
| 51 TOP | 8038.t00012 | peptidase M20/M25/M40, putative | ref|XP_019155.1| peptidase, M20/M25/M40 family [Coxiella burnetii RSA 493] (SCORE:1180, EVAL:1e-128, % IDS:49.5, % SEQ COV:96.8) | 1038 | 0 | 0 | 548 | 719 |
| 78 TOP | 6347.t00006 | peptidase M20/M25/M40, putative | ref|XP_019155.1| peptidase, M20/M25/M40 family [Coxiella burnetii RSA 493] (SCORE:1184, EVAL:1e-129, % IDS:55.2, % SEQ COV:96.8) | 820 | 0 | 0 | 489 | 520 |
| 547 TOP | 4893.t00017 | hypothetical protein, to be annotated (newly added gene) | gi|16152431|emb|CAC28618.1| proteasome subunit alpha5 [Trypanosoma cruzi] (SCORE:1176, EVAL:1e-127, % IDS:95.1, % SEQ COV:91.7) | 192 | 0 | 140 | 52 | 0 |
| 645 TOP | 7008.t00003 | ubiquitin-like protein, putative | ref|NP_922572.1| putative ubiquitin protein [Oryza sativa (japonica cultiva (SCORE:169, EVAL:3e-11, % IDS:35.4, % SEQ COV:26.4) | 72 | 0 | 60 | 0 | 72 |
| 366 TOP | 7358.t00019 | calpain-like cysteine peptidase, putative | emb|CAB59341.1| calpain-like protein, probable [Trypanosoma brucei] (SCORE:2593, EVAL:0.0, % IDS:52, % SEQ COV:55.1) | 221 | 0 | 0 | 221 | 0 |
| 949 TOP | 8320.t00008 | mitochondrial processing peptide beta subunit, putative | ref|NP_047087.1| MPP1.1439.1 [Leishmania major] pir|l1028:49 mitochondrial (SCORE:1620, EVAL:1e-179, % IDS:65.5, % SEQ COV:55.2) | 66 | 66 | 0 | 0 | 0 |
| 1103 TOP | 422.t00001 | D-alanyl-glycyl endopeptidase-like protein | ref|XP_360402.1| hypothetical protein 1092/2.3440 [Trypanosoma brucei] gb| (SCORE:519, EVAL:1e-179, % IDS:43.9, % SEQ COV:84.5) | 47 | 47 | 0 | 0 | 0 |
| 1060 TOP | 7359.t00005 | proteasome beta 6 subunit, putative | gb|AAF05505.1| 20S proteasome beta 6 subunit [Trypanosoma brucei] emb|CAE (SCORE:1052, EVAL:1e-113, % IDS:70.6, % SEQ COV:100) | 52 | 52 | 0 | 0 | 0 |
| 39 TOP | 7435.t00003 | glutamyl carboxypeptidase, putative | ref|NP_882101.1| putative peptidase [Bordetella pertussis Tohama I] emb|CAE (SCORE:973, EVAL:1e-104, % IDS:51.4, % SEQ COV:97.2) | 1275 | 105 | 0 | 794 | 937 |
| 43 TOP | 8516.t00001 | glutamyl carboxypeptidase, putative | ref|NP_882101.1| putative peptidase [Bordetella pertussis Tohama I] emb|CAE (SCORE:984, EVAL:1e-104, % IDS:51.9, % SEQ COV:97.2) | 1203 | 105 | 0 | 733 | 1006 |
| 33 TOP | 7420.t00002 | glutamyl carboxypeptidase, putative | ref|NP_882101.1| putative peptidase [Bordetella pertussis Tohama I] emb|CAE (SCORE:974, EVAL:1e-104, % IDS:51.1, % SEQ COV:97.4) | 1437 | 105 | 0 | 733 | 1160 |
| 98 TOP | 7435.t00005 | glutamyl carboxypeptidase, putative | ref|NP_882101.1| putative peptidase [Bordetella pertussis Tohama I] emb|CAE (SCORE:913, EVAL:1e-94, % IDS:46.6, % SEQ COV:94.4) | 647 | 69 | 0 | 304 | 449 |
| 99 TOP | 8681.t00012 | glutamyl carboxypeptidase, putative | ref|XP_824317.1| putative peptidase [Bordetella pertussis Tohama I] emb|CAE (SCORE:1058, EVAL:1e-113, % IDS:53, % SEQ COV:95.7) | 718 | 0 | 0 | 522 | 407 |

*Fig. 7d*

Fig. 7e

| | | | | | | | |
|---|---|---|---|---|---|---|---|
| 501 TOP | 4805.100010 | hypothetical protein, conserved | emb|CAJ940(22.2| possible protein kinase inhibitor [Leishmania major] (SCORE:359, EVAL:1e-102, % IDS:45.4, % SEQ COV:79.2) | 213 | | 60 | 133 | 0 |
| 842 TOP | 5914.100008 | hypothetical protein, conserved | ref|NP_889345.2| chromosome 6 open reading frame 205; chromosome 6 open rea (SCORE:169, EVAL:5e-10, % IDS:39.1, % SEQ COV:23.3) | 77 | 0 | 77 | 0 | 0 |
| 765 TOP | 8526.100003 | hypothetical protein, conserved | ref|XP_233353.2| similar to hypothetical protein [Rattus norvegicus] (SCORE:184, EVAL:1e-12, % IDS:29.9, % SEQ COV:68.2) | 118 | 0 | 72 | 46 | 0 |
| 733 TOP | 5823.100002 | hypothetical protein, conserved | emb|CAJ03257.2| hypothetical protein L5649J03 [Leishmania major] emb|CAC14515 (SCORE:455, EVAL:1e-43, % IDS:46.2, % SEQ COV:26.2) | 70 | 0 | 70 | 0 | 0 |
| 937 TOP | 7073.100014 | hypothetical protein, conserved | gb|AAR61869.1| unknown [Leishmania infantum] (SCORE:272, EVAL:1e-23, % IDS:57.1, % SEQ COV:91.8) | 69 | 0 | 69 | 0 | 0 |
| 249 TOP | 4859.100001 | hypothetical protein, conserved | ref|NP_082239.1| RIKEN cDNA 1700019P03 [Mus musculus] dbj|BAB24415.1| unnam (SCORE:1346, EVAL:1e-147, % IDS:41.9, % SEQ COV:97) | 260 | 0 | 66 | 194 | 0 |
| 590 TOP | 8755.100007 | hypothetical protein, conserved | | 106 | 0 | 66 | 40 | 0 |
| 968 TOP | 7678.100015 | hypothetical protein | | 64 | 0 | 64 | 0 | 0 |
| 537 TOP | 6996.100055 | hypothetical protein | ref|NP_703392.1| hypothetical protein [Plasmodium falciparum 3D7] emb|CAD51 (SCORE:259, EVAL:9e-21, % IDS:29.4, % SEQ COV:97.7) | 95 | 0 | 54 | 41 | 0 |
| 571 TOP | 22860.100003 | hypothetical protein, conserved | emb|CAC37209.1| C2 domain protein [Leishmania major] (SCORE:443, EVAL:2e-47, % IDS:45, % SEQ COV:79.1) | 176 | 0 | 54 | 122 | 0 |
| 1015 TOP | 8369.100013 | hypothetical protein, conserved | | 56 | 0 | 56 | 0 | 0 |
| 1015 TOP | 8369.100013 | hypothetical protein, conserved | | 56 | 0 | 56 | 0 | 0 |
| 1045 TOP | 7898.100005 | hypothetical protein, conserved | | 53 | 0 | 53 | 0 | 0 |
| 1058 TOP | 4896.100003 | hypothetical protein, to be annotated (newly added gene) | | 52 | 0 | 52 | 0 | 0 |
| 1069 TOP | 8793.100009 | hypothetical protein, conserved | gb|AAM08669.1| TC3_70K14.3 [Trypanosoma cruzi] (SCORE:4030, EVAL:0.0, % IDS:78.4, % SEQ COV:97.6) | 51 | 0 | 51 | 0 | 0 |
| 526 TOP | 8743.100001 | hypothetical protein, conserved | | 162 | 0 | 49 | 113 | 0 |
| 1083 TOP | 4835.100014 | hypothetical protein, conserved | | 49 | 0 | 49 | 0 | 0 |
| 1092 TOP | 8727.100012 | hypothetical protein, conserved | | 48 | 0 | 48 | 0 | 0 |
| 1094 TOP | 4718.100004 | hypothetical protein, to be annotated (newly added gene) | | 48 | 0 | 48 | 0 | 0 |
| 1137 TOP | 7482.100004 | hypothetical protein | ref|XP_308201.1| ENSANGP00000021656 [Anopheles gambiae] gb|EAA04113.2| ENSA (SCORE:141, EVAL:9e-08, % IDS:25, % SEQ COV:60.3) | 45 | 0 | 45 | 0 | 0 |
| 1139 TOP | 8133.100014 | hypothetical protein, to be annotated (newly added gene) | | 45 | 0 | 45 | 0 | 0 |
| 1155 TOP | 8656.100007 | hypothetical protein, conserved | | 43 | 0 | 43 | 0 | 0 |
| 321 TOP | 5563.100004 | hypothetical protein, conserved | | 201 | 0 | 39 | 201 | 0 |
| 41 OTHER | 6207.100018 | hypothetical protein, to be annotated (newly added gene) | | 1256 | 0 | 74 | 994 | 370 |
| 41 TOP | 7120.100018 | hypothetical protein | | 1320 | 0 | 74 | 994 | 434 |
| 1139 TOP | 7120.100017 | hypothetical protein, conserved | | 1095 | 0 | 74 | 833 | 370 |
| 57 TOP | 6207.100017 | hypothetical protein, conserved | | 950 | 0 | 74 | 608 | 370 |
| 43 OTHER | 8516.100004 | hypothetical protein, to be annotated (newly added gene) | gb|3356445/ref|NP_882101.1| putative peptidase [Bordetella pertussis] ref|am (SCORE:862, EVAL:5e-90, % IDS:53.8, % SEQ COV:39.4) | 1133 | 105 | 0 | 685 | 909 |
| 123 TOP | 5442.100003 | hypothetical protein | | 645 | 58 | 188 | 589 | 0 |
| 123 OTHER | 7120.100018 | hypothetical protein | | 645 | 58 | 198 | 589 | 0 |
| 123 TOP | 7472.100004 | hypothetical protein | | 645 | 58 | 198 | 589 | 0 |
| 77 TOP | 7368.100001 | hypothetical protein, conserved | | 777 | 271 | 149 | 559 | 0 |
| 83 TOP | 6297.100003 | hypothetical protein, conserved | | 701 | 190 | 94 | 501 | 0 |
| 291 TOP | 7691.100008 | hypothetical protein, conserved | sp|Q5JE5|PLELF_CRIGR Placlin 1 [PLN] [PCN] (30c<4>a intermediate filament- (SCORE:210, EVAL:2e-14, % IDS:20.4, % SEQ COV:24.9) | 271 | 0 | 38 | 270 | 0 |
| 419 TOP | 6889.100010 | hypothetical protein, conserved | | 224 | 85 | 0 | 220 | 0 |

Fig. 7f

| | | | | | | | |
|---|---|---|---|---|---|---|---|
| 213 TOP | 8501.t00003 | hypothetical protein, conserved | dbj\|BAC26479.1\| unnamed protein product [Mus musculus] (SCORE:674, EVAL:5e-69, % IDS:30.9, % SEQ COV:65.3) | 414 | 0 | 266 | 0 |
| 321 TOP | 5563.t00004 | hypothetical protein, conserved | | 201 | 0 | 39 | 201 |
| 232 TOP | 3113.t00001 | hypothetical protein, to be annotated (newly added gene) | gi\|37521860\|ref\|NP_922337.1\| hypothetical protein gl/2391 [Gloeobacter violaceus] (SCORE:435, EVAL:1e-41, % IDS:32, % SEQ COV:93.5) | 390 | 0 | 44 | 390 |
| 224 TOP | 8754.t00004 | hypothetical protein, to be annotated (newly added gene) | gi\|3512677\|sp\|Q89417\|MYT_HUMAN C-Myc-binding protein (Associate of Myc 1) (SCORE:183, EVAL:1e-13, % IDS:48.6, % SEQ COV:88.1) | 362 | 0 | 0 | 362 |
| 314 TOP | 5921.t00006 | hypothetical protein, to be annotated (newly added gene) | gi\|38202202\|gb\|AAR14054.1\| tc300 [Trypanosoma cruzi] (SCORE:3875, EVAL:0.0, % IDS:96.4, % SEQ COV:99.9) | 296 | 0 | 0 | 296 |
| 301 TOP | 8736.t00002 | hypothetical protein, to be annotated (newly added gene) | gi\|16531419\|gb\|AAF15410.1\| antigen [Leishmania major] (SCORE:893, EVAL:6e-95, % IDS:75.7, % SEQ COV:83.9) | 237 | 85 | 0 | 237 |
| 163 TOP | 8564.t00026 | hypothetical protein, to be annotated (newly added gene) | | 449 | 74 | 95 | 0 | 426 |
| 936 TOP | 4830.t00003 | hypothetical protein, to be annotated (newly added gene) | | 69 | 0 | 0 | 0 | 69 |
| 516 TOP | 7052.t00029 | hypothetical protein, to be annotated (newly added gene) | gi\|39583443\|emb\|CAE73931.1\| Hypothetical protein CBG21357 [Caenorhabditis b] (SCORE:442, EVAL:1e-43, % IDS:55.5, % SEQ COV:100) | 172 | 0 | 107 | 0 | 167 |
| 376 TOP | 6089.t00003 | hypothetical protein, conserved | | 163 | 0 | 0 | 0 | 163 |
| 684 TOP | 4844.t00001 | hypothetical protein, conserved | ref\|NP_932114.2\| hypothetical protein C130059A02 [Mus musculus] (SCORE:232, EVAL:8e-18, % IDS:31.1, % SEQ COV:36.1) | 139 | 0 | 37 | 0 | 139 |
| 798 TOP | 8073.t00022 | hypothetical protein, to be annotated (newly added gene) | | 107 | 0 | 0 | 0 | 107 |
| 624 TOP | 8476.t00008 | hypothetical protein, conserved | | 101 | 0 | 0 | 0 | 101 |
| 686 TOP | 7595.t00003 | hypothetical protein, conserved | emb\|CAB95231.1\| MNUDC-like protein [Leishmania major] (SCORE:918, EVAL:9e-36, % IDS:56.6, % SEQ COV:99.3) | 139 | 52 | 51 | 0 | 87 |
| 869 TOP | 3300.t00001 | hypothetical protein, conserved | | 84 | 0 | 0 | 0 | 84 |
| 872 TOP | 7056.t00010 | hypothetical protein, to be annotated (newly added gene) | | 84 | 0 | 0 | 0 | 84 |
| 763 TOP | 7164.t00032 | hypothetical protein, to be annotated (newly added gene) | | 112 | 0 | 37 | 0 | 75 |
| 513 TOP | 5759.t00001 | hypothetical protein, conserved | | 69 | 0 | 0 | 0 | 69 |
| 385 TOP | 8197.t00006 | hypothetical protein, conserved | gb\|EAA40509.1\| hypothetical protein MG00167.4 [Magnaporthe grisea 70-15] (SCORE:273, EVAL:5e-23, % IDS:42.4, % SEQ COV:46.8) | 242 | 147 | 0 | 191 | 0 |
| 802 TOP | 6853.t00027 | hypothetical protein, to be annotated (newly added gene) | gi\|11245490\|gb\|AAG33541.1\| C-terminal kinesin KifC1 [Trypanosoma brucei] (SCORE:2493, EVAL:0.0, % IDS:67.2, % SEQ COV:98.8) | 106 | 106 | 0 | 0 | 0 |
| 320 TOP | 8691.t00020 | hypothetical protein, conserved | emb\|CAB95542.1\| hypothetical protein [Trypanosoma brucei] (SCORE:1476, EVAL:1e-162, % IDS:33.7, % SEQ COV:96.2) | 231 | 157 | 0 | 74 | 0 |
| 682 TOP | 6140.t00001 | hypothetical protein, to be annotated (newly added gene) | gi\|28865254\|gb\|AAH48082.1\| small glutamine-rich tetratricopeptide repeat (1 (SCORE:359, EVAL:1e-32, % IDS:34.3, % SEQ COV:57.4) | 139 | 139 | 0 | 0 | 42 |
| 929 TOP | 8576.t00003 | hypothetical protein, to be annotated (newly added gene) | gi\|34620553\|gb\|AAH50519.1\| TMUB_1 protein [Caenorhabditis elegans] (SCORE:1036, EVAL:1e-111, % IDS:26.6, % SEQ COV:93.6) | 70 | 70 | 0 | 0 | 0 |
| not classified | | | | | | | | |
| 497 TOP | 6865.t00006 | lectin, putative | gb\|AAG46367.1\| antigen 36 [Trypanosoma cruzi] (SCORE:1610, EVAL:1e-177, % IDS:94.9, % SEQ COV:57.3) | 221 | 35 | 221 | 0 | 0 |
| 329 TOP | 6142.t00008 | kinetoplast DNA-associated protein, putative | gi\|50631716\|gb\|EAL16931.1\| unnamed protein: putative Ornithine lipase precursor - Ornithine base [SCORE:194, EVAL:1e-13, % IDS:39.6, % SEQ COV:51.8) | 230 | 58 | 0 | 212 | 0 |
| replication | | | | | | | | |
| 974 TOP | 5429.t00012 | variant-surface-glycoprotein phospholipase c (ec 4.6.1.14) (vsg\|pase) (glycosyl\|phosphatidyl\|inositol-specific phospholipase c) (gpi-plc) | sp\|O15866\|PHLC_TRYCR Variant-surface-glycoprotein phospholipase C (VSG lipa (SCORE:1364, EVAL:1e-149, % IDS:71.2, % SEQ COV:99.7) | 62 | 62 | 0 | 0 | 0 |

*Fig. 7g*

Figure 8
Table 6: Correlation of microarray and proteomic data for selected proteins Accession: Accession numbers of the GSS clones used in the microarrays.
Gene ID: Gene ID in the TSK-TSC annotated genome to which the GSS sequences were mapped.
Gene Name: Assigned name of the gene in the TSK-TSC annotated genome
Array Ratio: Mean linear ratios (ama/tryp) from six microarray hybridizations.
Proteome Ratio: Ratios (ama/tryp) of cumulative scores from high quality peptides (< 5% false discovery rate). Where the protein score is zero, no ratio is computed

| Category | Accession | Gene ID | Gene Name | Array Ratio (s.d.) | Proteome Ratio |
|---|---|---|---|---|---|
| Metabolism | AQ445365 | 7626.t00011 | cystathionine beta-synthase, putative | 2.1 (0.70) | 522/0 |
| Metabolism | AZ050742 | 8754.t00002 | cystathionine beta-synthase, putative | 2.3 (1.04) | 4.76 |
| Metabolism | AQ910499 | 8754.t00001 | cystathionine beta-synthase, putative | 2.8 (0.75) | 452/0 |
| Metabolism | AQ904424 | 7603.t00003 | glutamate dehydrogenase, putative | 2.5 (0.77) | 3.69 |
| Metabolism | AQ904565 | 7767.t00005 | aminotransferase, putative | 2.0 (0.90) | 1.44 |
| Metabolism | AZ050734 | 8304.t00012 | d-isomer specific 2-hydroxyacid dehydrogenase-protein, putative | 2.8 (1.30) | 2.13 |
| Metabolism | AQ445056 | 8327.t00001 | sterol 24-c-methyltransferase, putative | 1.7 (0.87) | 1.12 |
| Protein Synthesis | AZ050802 | 8674.t00001 | elongation factor 1-alpha | 2.4 (0.40) | 1.64 |
| Protein Synthesis | AZ050696 | 8171.t00017 | 60S ribosomal protein L9, putative | 2.2 (0.46) | 1.51 |
| Protein Synthesis | AZ050078 | 5341.t00005 | 60s ribosomal protein 118, putative | 2.2 (1.61) | 1.51 |
| Protein Synthesis | AI005689 | 7052.t00010 | 40S ribosomal protein S18, putative | 3.3 (0.49) | 0/107 |
| Protein Destination | AQ904697 | 8158.t00013 | heat shock protein 85 | 2.6 (0.53) | 2.56 |
| Protein Destination | AQ911144 | 8158.t00013 | heat shock protein 85 | 1.9 (0.37) | 2.56 |
| Protein Destination | AZ049920 | 8158.t00013 | heat shock protein 85 | 2.9 (1.20) | 2.56 |
| Protein Destination | AQ444434 | 8621.t00016 | heat-shock protein hsp70, putative | 3.4 (1.32) | 2.80 |
| Protein Destination | AZ050577 | 7127.t00040 | peptidyl-prolyl cis-trans isomerase (cyclophilin-40), putative | 1.9 (0.34) | 1.25 |
| Protein Destination | AQ907901 | 7435.t00003 | glutamamyl carboxypeptidase, putative | 1.8 (0.35) | 105/0 |
| Protein Destination | AZ050783 | 7106.t00002 | ATP-dependent Clp protease subunit, heat shock protein 100 (HSP100), putative | 2.1 (0.86) | 113/0 |
| Transport | AQ443513 | 8319.t00008 | ABC transporter, putative | 2.6 (1.32) | 164/0 |

Microarrays of PCR amplified sequences from Trypanosoma cruzi GSS clones were

*Fig. 8*

| Fig. 9a |
| Fig. 9b |
| Fig. 9c |
| Fig. 9d |
| Fig. 9e |
| Fig. 9f |
| Fig. 9g |

Fig. 9

Table 7: Trypanosoma cruzi expressed proteins with selected modifications identified from TSK-TSC annotated genome

| Gene ID / Peptide | Top BLAST Hit | Score | | | | | |
|---|---|---|---|---|---|---|---|
| | | Total | Amastigote | Trypomastigote | Metacyclic | Epimastigote |
| 6998.t00004 [FPGQLNSDLR+Deamidation (NQ)]; [FPGQLNSDLRK +Deamidation (NQ)]; [LAVNLVPFPR +Deamidation (NQ)]; [NSSYFIEWIPNNIK +Deamidation (NQ)]; [TLKLTTPTFGDLNHLVSAVVSGVTCCLR +Acetyl (K); 2 Carbamidomethyl (C); Carbamyl (N-term)] | gb|AAL75956.1| beta tubulin 1.9 [Trypanosoma cruzi] gb|AAL75957.1| beta tub | 325 | 145 | 131 | 170 | 112 |
| 5635.t00007 | gb|AAL75956.1| beta tubulin 1.9 [Trypanosoma cruzi] gb|AAL75957.1| beta tub | 325 | 145 | 131 | 170 | 112 |
| 8621.t00017 [ATNGDTHLGGEDFDNR +Deamidation (NQ)]; [NTITSAVEEALQWLNNNQEASKEEYEHR +Deamidation (NQ)]; [NTITSAVEEALQWLNNNQEASKEEYEHR +Deamidation (NQ); Methylation (K); tri-methylation (R)]; [SINPDEAVAYGAAVQAFILTGGK +Deamidation (NQ)] | gb|AAA30205.1| heat shock protein HSP70 | 289 | 94 | 0 | 226 | 78 |
| 8621.t00016 | gb|AAA30205.1| heat shock protein HSP70 | 289 | 94 | 0 | 226 | 78 |
| 7355.t00010 [DGNGFISAAELR+Deamidation (NQ)]; [MQDSDSEEEIKEAFR +Phospho (ST)]; [VFDKDGNGFISAAELR +Deamidation (NQ)] | gi|115531|sp|P18061|CALM_TRYCR Calmodulin (CaM) gi|71680|pir||MCUTC calmodu | 212 | 0 | 95 | 131 | 72 |
| 7355.t00005 | sp|P18061|CALM_TRYCR Calmodulin pir||MCUTC calmodulin - Trypanosoma cruzi | 212 | 0 | 95 | 131 | 72 |

Fig. 9a

| | | | | | | |
|---|---|---|---|---|---|---|
| 6925.t00001 | sp\|P18061\|CALM_TRYCR Calmodulin pir\|\|MCUTC calmodulin - Trypanosoma cruzi | 212 | 0 | 95 | 131 | 72 |
| 7355.t00003 | sp\|P18061\|CALM_TRYCR Calmodulin pir\|\|MCUTC calmodulin - Trypanosoma cruzi | 212 | 0 | 95 | 131 | 72 |
| 6925.t00002 | sp\|P18061\|CALM_TRYCR Calmodulin pir\|\|MCUTC calmodulin - Trypanosoma cruzi | 212 | 0 | 95 | 131 | 72 |
| 8110.t00010 [EVSGAQKEGLR +Acetyl (K)]; [EVSGAQKEGLR +Acetyl (K); Carbamyl (N-term)]; [EVSGAQKEGLR +Methylation (K)]; [FQSSAILAAQEATESYVVSLLADTNR +Deamidation (NQ)] | gi\|25992799\|emb\|CAD53117.2\| histone H3, probable [Trypanosoma brucei] gi\|25 | 202 | 70 | 46 | 115 | 137 |
| 6741.t00005 | emb\|CAD53117.2\| histone H3, probable [Trypanosoma brucei] emb\|CAD53119.1\| h | 202 | 70 | 46 | 115 | 137 |
| 8110.t00006 | gi\|25992799\|emb\|CAD53117.2\| histone H3, probable [Trypanosoma brucei] gi\|25 | 202 | 70 | 46 | 115 | 137 |
| 7482.t00009 | gi\|25992799\|emb\|CAD53117.2\| histone H3, probable [Trypanosoma brucei] gi\|25 | 202 | 70 | 46 | 115 | 137 |
| 8110.t00007 | gi\|25992799\|emb\|CAD53117.2\| histone H3, probable [Trypanosoma brucei] gi\|25 | 202 | 70 | 46 | 115 | 137 |
| 6741.t00004 | emb\|CAD53117.2\| histone H3, probable [Trypanosoma brucei] emb\|CAD53119.1\| h | 202 | 70 | 46 | 115 | 137 |
| 8110.t00009 | gi\|25992799\|emb\|CAD53117.2\| histone H3, probable [Trypanosoma brucei] gi\|25 | 202 | 70 | 46 | 115 | 137 |
| 7482.t00010 | gi\|25992799\|emb\|CAD53117.2\| histone H3, probable [Trypanosoma brucei] gi\|25 | 202 | 70 | 46 | 115 | 137 |
| 7603.t00003 [AANAGGVAISGLEMSQNAAR +Deamidation (NQ); tri-methylation (R)]; [TNYVNGAMIAGFVK +Deamidation (NQ)]; [VQFNSSIGPYK +Deamidation (NQ)] | gb\|AAC06213.1\| putative glutamate dehydrogenase [Trypanosoma cruzi] | 179 | 0 | 0 | 42 | 179 |
| 6998.t00023 [GFDEGNGLLFR+Deamidation (NQ)]; [NGKPSFK +Deamidation (NQ)]; [NGKPSFKGDEIVK +Deamidation (NQ); di-methylation (K)] | gi\|9366722\|emb\|CAB95484.1\| calpain-like protein fragment, possible [Trypano | 162 | 42 | 0 | 162 | 27 |

*Fig. 9G*

| | | | | | |
|---|---|---|---|---|---|
| 7180.t00003 [SMENPNVTKDELSAATDK+Phospho (ST)]; [SSNGDAWVQDANGK +Deamidation (NQ)] | sp\|P20583\|HS71_TRYCR HEAT SHOCK 70 KD PROTEIN, MITOCHONDRIAL PRECURSOR pir\| | 143 | | 91 | 0 |
| 7147.t00028 [SMENPNVTKDELSAATDK+Phospho (ST)] | sp\|P20583\|HS71_TRYCR HEAT SHOCK 70 KD PROTEIN, MITOCHONDRIAL PRECURSOR pir\| | 52 | | 0 | 0 | 81 | 0 |
| 8771.t00001 | dbj\|BAC24979.1\| mitochondrial HSP70 [Trypanosoma congolense] | 52 | | 0 | 0 | 52 | 0 |
| 1989.t00001 | sp\|P20583\|HS71_TRYCR HEAT SHOCK 70 KD PROTEIN, MITOCHONDRIAL PRECURSOR pir\| | 52 | | 0 | 0 | 52 | 0 |
| 6138.t00004 | sp\|P20583\|HS71_TRYCR HEAT SHOCK 70 KD PROTEIN, MITOCHONDRIAL PRECURSOR pir\| | 52 | | 0 | 0 | 52 | 0 |
| 7685.t00010 [HVSVLAPNGLFTR +Deamidation (NQ)]; [KEEPTSPPPPPPQQK +Phospho (ST)] | sp\|Q26768\|AGI6_TRYBB I/6 AUTOANTIGEN emb\|CAA65390.1\| I/6 protein [Trypanoso | 133 | | 0 | 0 | 133 | 0 |
| 7639.t00014 [FGVNGYPTILFFPADSQTK +Deamidation (NQ)]; [LNADDASNGAVR +Methylation (R)] | ref\|NP_182269.1\| protein disulfide isomerase family [Arabidopsis thaliana] | 133 | | 80 | 115 | 26 | 76 |
| 5730.t00001 [KAAADLTGVEAVQYPR +Acetyl (K)]; [LNADDASNGAVR +Methylation (R)] | ref\|NP_910169.1\| putative disulfide-isomerase precursor [Oryza sativa] gb\|A | 122 | | 80 | 62 | 42 | 76 |
| 8673.t00037 [FESPKSVFTIIDAPGHR+Acetyl (K)]; [FESPKSVFTIIDAPGHR +Acetyl (K); Carbamyl (N-term)] | pir\|\|JC5117 translation elongation factor eEF-1 alpha - Trypanosoma cruzi | 114 | | 56 | 0 | 0 | 114 |
| 8309.t00008 | gi\|2133383\|pir\|\|JC5117 translation elongation factor eEF-1 alpha - Trypanos | 114 | | 56 | 0 | 0 | 114 |
| 8674.t00002 | pir\|\|JC5117 translation elongation factor eEF-1 alpha - Trypanosoma cruzi | 114 | | 56 | 0 | 0 | 114 |
| 8309.t00002 | pir\|\|JC5117 translation elongation factor eEF-1 alpha - Trypanosoma cruzi | 114 | | 56 | 0 | 0 | 114 |
| 8673.t00036 | pir\|\|JC5117 translation elongation factor eEF-1 alpha - Trypanosoma cruzi | 114 | | 56 | 0 | 0 | 114 |
| 5629.t00006 | gi\|2133383\|pir\|\|JC5117 translation elongation factor eEF-1 alpha - Trypanos | 114 | | 56 | 0 | 0 | 114 |
| 8674.t00001 | pir\|\|JC5117 translation elongation factor eEF-1 alpha - Trypanosoma cruzi | 114 | | 56 | 0 | 0 | 114 |

Fig. 9c

| Peptide ID | Protein | | | | | |
|---|---|---|---|---|---|---|
| 5423.t00007 [DNGNGLLFR+Deamidation (NQ)]; [TEIKYENGQPTFEGPTVVK +Acetyl (K)] | gi|12329969|emb|CAC24686.1| conserved hypothetical protein [Leishmania majo | 98 | 0 | 0 | 98 | 48 |
| 5423.t00008 | gi|12329969|emb|CAC24686.1| conserved hypothetical protein [Leishmania majo | 98 | 0 | 0 | 98 | 48 |
| 6836.t00005 [SRTHYVDSTGEYNFVR +di-methylation (R)] | ref|NP_925337.1| hypothetical protein glr2391 [Gloeobacter violaceus] dbj|B | 97 | 0 | 0 | 54 | 97 |
| 7885.t00004 | ref|NP_925337.1| hypothetical protein glr2391 [Gloeobacter violaceus] dbj|B | 97 | 0 | 0 | 54 | 97 |
| 5947.t00007 [VEEVPTTAETPETPVPAEKTDDADAEDGGELDE R +Methylation (K)]; [VEEVPTTAETPETPVPAEKTDDADAEDGGELDE R +Methylation (R)] | gb|AAM54029.1| NAC alpha [Trypanosoma cruzi] | 92 | 0 | 0 | 0 | 92 |
| 8342.t00006 | gb|AAM54029.1| NAC alpha [Trypanosoma cruzi] | 92 | 0 | 0 | 0 | 92 |
| 6287.t00003 [LELDHQLQQAVEEEDK +di-methylation (K)] | | 90 | 90 | 0 | 0 | 0 |
| 7388.t00001 | | 90 | 90 | 0 | 0 | 0 |
| 5633.t00003 [ANQDSGVVWTEEVLDVYLENPKK +Acetyl (K); Carbamyl (N-term)]; [GGANGVGPNLYGIYGR +Deamidation (NQ)] | gi|117974|sp|P00077|CYC_CRION Cytochrome c gi|65522|pir||CCCRCO cytochrome | 86 | 46 | 57 | 40 | 0 |
| 7402.t00001 [SGRPEEGHYGNEESQSPTVPR +tri-methylation (R)] | gb|AAM08904.1| TC3_4711 2.4 [Trypanosoma cruzi] | 79 | 0 | 0 | 79 | 0 |
| 4919.t00004 [TARPSVSVYSASEDK +tri-methylation (R)] | gi|1350685|sp|P49669|RL4_TRYBB 60S ribosomal protein L4 (L1) gi|1015931|emb | 77 | 77 | 0 | 0 | 55 |
| 4690.t00006 | gi|1350685|sp|P49669|RL4_TRYBB 60S ribosomal protein L4 (L1) gi|1015931|emb | 77 | 77 | 0 | 0 | 55 |
| 4919.t00003 | sp|P49669|RL4_TRYBB 60S RIBOSOMAL PROTEIN L4 (L1) emb|CAA91141.1| ribosomal | 77 | 77 | 0 | 0 | 55 |
| 5825.t00009 [LDTFLAGSAVTLQNMALVEANK +Methylation (K)] | ref|NP_647756.1| CG21107-PA [Drosophila melanogaster] gb|AAF47698.1| CG2107 | 69 | 0 | 69 | 0 | 0 |

Fig. 9d

| ID [Peptide] | Accession [Description] | | | | | | |
|---|---|---|---|---|---|---|---|
| 7612.t00024 [NSFISPSLVSAGGVIAAFAEGQVYTVNGAR +Methylation (R)] | gb\|AAM47176.1\| surface glycoprotein GP90 [Trypanosoma cruzi] | 67 | 0 | 67 | 0 | 0 | 0 |
| 7612.t00025 | gb\|AAM47176.1\| surface glycoprotein GP90 [Trypanosoma cruzi] | 67 | 0 | 67 | 0 | 0 | 0 |
| 5319.t00008 [DPNDVTAPQDK +Methylation (K)] | | 61 | 0 | 0 | 0 | 0 | 61 |
| 6912.t00005 [ANGGTTYDYEGLDK +di-methylation (K)] | gb\|AAL96371.1\| Tcc44h21-2.8 [Trypanosoma cruzi] | 53 | 0 | 0 | 0 | 0 | 53 |
| 8643.t00006 | gb\|AAL96371.1\| Tcc44h21-2.8 [Trypanosoma cruzi] | 53 | 0 | 0 | 0 | 0 | 53 |
| 7402.t00011 [NSLDAALEEVR+Methylation (R)] | gb\|AAM89904.1\| TC3_47I12.4 [Trypanosoma cruzi] | 53 | 53 | 0 | 0 | 0 | 0 |
| 7143.t00012 [VIDLSVSKTGK+Acetyl (K)] | emb\|CAB95733.1\| eukaryotic initiation factor 5a [Leishmania infantum] | 52 | 0 | 0 | 52 | 0 | 0 |
| 7143.t00013 | emb\|CAB95733.1\| eukaryotic initiation factor 5a [Leishmania infantum] | 52 | 0 | 0 | 52 | 0 | 0 |
| 8485.t00015 [NIKHSGNIPFSEILK+Acetyl (K); Carbamyl (N-term)] | gi\|17541134\|ref\|NP_502542.1\| ribosomal Protein, Large subunit (17.8 kD) (rp | 51 | 0 | 51 | 0 | 0 | 0 |
| 7719.t00007 | gi\|17541134\|ref\|NP_502542.1\| ribosomal Protein, Large subunit (17.8 kD) (rp | 51 | 0 | 51 | 0 | 0 | 0 |
| 4877.t00003 | ref\|NP_502542.1\| ribosomal Protein, Large subunit (17.8 kD) (rpl-12) [Caeno | 50 | 0 | 0 | 50 | 0 | 0 |
| 7853.t00045 [TVEVGVATAVAPHCQVGGGALCTLDGKK +di-methylation (K); O-GlcNac (T)] | gi\|33944403\|ref\|XP_340349.1\| hypothetical protein Tb927.2.2510 [Trypanosoma | 48 | 48 | 0 | 0 | 0 | 0 |
| 8185.t00017 [LDQLIYIPLPDK+di-methylation (K)] | gb\|AAC02215.1\| valosin-containing protein homolog [Trypanosoma brucei] | 48 | 0 | 0 | 0 | 48 | 0 |
| 5945.t00001 [KSEYDEAGPSIVHNK+Acetyl (K)] | sp\|P53477\|ACT_TRYCR ACTIN gb\|AAA62141.1\| actin 1 [Trypanosoma cruzi] gb\|AAA | 48 | 0 | 0 | 0 | 48 | 0 |
| 8434.t00003 | gb\|AAP97326.1\| actin 1 [Trypanosoma cruzi] gb\|AAP97327.1\| actin 2 [Trypanos | 47 | 47 | 0 | 0 | 31 | 0 |
| 6869.t00005 [YAEASPGLDQYAVR+Methylation (R)] | gb\|AAL35374.1\| CCT chaperonin theta subunit [Physarum polycephalum] | 47 | 47 | 0 | 0 | 0 | 0 |
| 6124.t00002 [VGMLVCGPCTVVQAALGEALLNTPQEHLDQIVAK +Phospho (ST)] | sp\|P33447\|ATTY_TRYCR Tyrosine aminotransferase (L-tyrosine:2-oxoglutarate a | 47 | 47 | 0 | 0 | 0 | 0 |

Fig. 9e

| | | | | | |
|---|---|---|---|---|---|
| 8328.t00003 | sp\|P33447\|ATTY_TRYCR Tyrosine aminotransferase (L-tyrosine:2-oxoglutarate a | 47 | 0 | 0 | 0 |
| 8328.t00004 | sp\|P33447\|ATTY_TRYCR Tyrosine aminotransferase (L-tyrosine:2-oxoglutarate a | 47 | 47 | 0 | 0 |
| 8328.t00005 | sp\|P33447\|ATTY_TRYCR Tyrosine aminotransferase (L-tyrosine:2-oxoglutarate a | 47 | 47 | 0 | 0 |
| 6876.t00003 [SASTKEVDEYGVR+di-methylation (K)] | ref\|NP_691765.1\| dehydrogenase [Oceanobacillus iheyensis HTE831] dbj\|BAC128 | 46 | 0 | 0 | 46 |
| 6876.t00001 | emb\|CAA72787.1\| hypothetical protein [Trypanosoma cruzi] | 46 | 0 | 0 | 46 |
| 8304.t00012 | emb\|CAA72787.1\| hypothetical protein [Trypanosoma cruzi] | 46 | 0 | 0 | 46 |
| 6876.t00002 | emb\|CAA72787.1\| hypothetical protein [Trypanosoma cruzi] | 46 | 0 | 0 | 46 |
| 8494.t00002 [SDPDKSNTAASQEDASGNVASK +Acetyl (K)] | gb\|AAH64273.1\| Unknown (protein for MGC:76305) [Silurana tropicalis] | 45 | 0 | 0 | 45 |
| 4935.t00028 [DASQKADLDQR+Phospho (ST)] | | 45 | 0 | 0 | 45 |
| 7435.t00004 [IAGAPTVICGPNGGAIHCANEYVTPAQLDK +Carbamidomethyl (C); Phospho (Y)] | ref\|NP_882101.1\| putative peptidase [Bordetella pertussis Tohama I] emb\|CAE | 44 | 0 | 44 | 0 |
| 7435.t00003 | ref\|NP_882101.1\| putative peptidase [Bordetella pertussis Tohama I] emb\|CAE | 44 | 0 | 44 | 0 |
| 7435.t00005 | ref\|NP_882101.1\| putative peptidase [Bordetella pertussis Tohama I] emb\|CAE | 44 | 0 | 0 | 0 |
| 7814.t00020 [ASKPQPIAAANWK+Acetyl (K)] | gi\|1730005\|sp\|P52270\|TPIS_TRYCR Triosephosphate isomerase, glycosomal (TIM) | 44 | 0 | 0 | 44 |
| 7143.t00030 [SYKPHHATVPTNPK+Acetyl (K); Carbamyl (N-term)] | gb\|AAF05985.1\| cyclophilin A [Trypanosoma cruzi] | 37 | 32 | 37 | 0 |
| 7898.t00018 [AEGIKWHNAAIQDELVPK +Acetyl (K)] | pir\|\|F86391 T1K7.15 protein - Arabidopsis thaliana gb\|AAF98570.1\| Strong si | 36 | 0 | 0 | 36 |

Fig. 9f

| 8730.t00013 | pir||F86391 T1K7.15 protein - Arabidopsis thaliana gb|AAF98570.1| Strong si | 36 | 0 | 0 | 0 | 36 |

Modified proteins which were not identified in the proteome

| Gene ID / Peptide | Top BLAST Hit | Score | | | | |
|---|---|---|---|---|---|---|
| | | Total | Amastigote | Trypomastigote | Metacyclic | Epimastigote |
| 7924.t00021 [LSPNGFSEVVQYLR +Deamidation (NQ)] | | 49 | 0 | 0 | 49 | 0 |
| 7027.t00012 [ASTHQGNGVFR +Deamidation (NQ)] | emb|CAB95242.2| hypothetical protein L2802.08 [Leishmania major] emb|CAC371 | 46 | 0 | 46 | 36 | 0 |
| 6860.t00014 [RQDEAQALER +2 Deamidation (NQ); 2 Methylation (R)] | pir||T30521 surface protein - Trypanosoma cruzi dbj|BAA31361.1| surface pro | 66 | 66 | 0 | 0 | 0 |
| 8413.t00005 [EVLKDAIR +Acetyl (K); Carbamyl (N-term)] | ref|NP_776877.1| Rho-associated, coiled-coil containing protein kinase 1 [B | 53 | 0 | 0 | 53 | 0 |
| 8328.t00052 [QQLEEAQR +Methylation (R)] | emb|CAD38824.1| NIMA-related kinase [Crithidia fasciculata] | 49 | 0 | 0 | 49 | 0 |
| 6898.t00008 [GSTQRSDIQK +Deamidation (NQ); di-methylation (K)] | gb|AAO24601.1| histone H3 variant [Trypanosoma brucei] gb|AAO24602.1 | 48 | 31 | 0 | 48 | 0 |
| 6974.t00015 [EIVSNLKDSFR +Acetyl (K)] | gb|AAO24601.1| histone H3 variant [Trypanosoma brucei] gb|AAO24602.1 | 37 | 0 | 37 | 0 | 0 |
| 7181.t00002 | | 37 | 0 | 37 | 0 | 0 |

Fig. 9g

Table 8: Trypanosoma cruzi expressed proteins identified from ORF database (ORFans)

| ORF ID | Assigned Gene name | T cruzi BLASTP | NR BLASTP | T brucei BLASTP | L major BLASTP | Score | |
|---|---|---|---|---|---|---|---|
| | | | | | | Peptides Identified only on ORFans | All Peptides Identified in the Proteome and on ORFans |
| Tc_TIGR_TCPOV11TF_consensus.5 | carnitine/choline acetyltransferase | 5825.t00009\|carnitine/choline acetyltransferase, putative | gi\|24656312\|ref\|NP_647756.1\| CG2107-PA [Drosophila melanogaster] gi\|7292290 | Tb_Sanger_Tb11.18.0006\|choline/carnitine O-acetyltransferase, putative | Lm_Sanger_LmjF29.1310\|choline/carnitine acetyl transferase, putative | 204 | 505 |
| Tc_TIGR_TCONA40TR_consensus.10 | urocanate hydratase | 4881.t00011\|urocanate hydratase | gi\|28828219\|gb\|AAO50896.1\| similar to Mus musculus (Mouse). Probable urocan | | | 50 | 484 |
| TRG_Sequence146.1 | hexose transporter | 6911.t00001\|hexose transporter, putative | gi\|453380\|gb\|AAA21207.1\| hexose transporter | Tb_Sanger_Tb10.6k15.2020\|glucose transporter | Lm_Sanger_LmjF36.6300\|glucose transporter, putative | 69 | 129 |

Fig. 10

SEQUENCE LISTING

<160> NUMBER OF SEQ ID NOS: 14

<210> SEQ ID NO 1
<211> LENGTH: 17
<212> TYPE: PRT
<213> ORGANISM: Trypanosoma cruzi

<400> SEQUENCE: 1

Ala Ala Ala Glu Ala Ala Ala Thr Ala Thr Glu Ala Ala Glu Ala Ala
1               5                   10                  15

Lys

<210> SEQ ID NO 2
<211> LENGTH: 11
<212> TYPE: PRT
<213> ORGANISM: artificial
<220> FEATURE:
<223> OTHER INFORMATION: fatty acid transporter motif
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Ile Tyr Thr Ser Gly Thr Thr Gly Xaa Pro Lys
1               5                   10

<210> SEQ ID NO 3
<211> LENGTH: 1416
<212> TYPE: DNA
<213> ORGANISM: Trypanosoma Cruzi

<400> SEQUENCE: 3
atgtttagaa cttacaatgg tatccgcttc ttccgtgtct ttttgacgct gtggatcact      60
tacgccgcct acaccatggt tcgtcgacct ctgactgtgg cacgtgccga tattcaacgg     120
gagacggggt ttacttcggc agaaacatcg cttgtagata cgatgtttgt ttttcatat      180 gcacttgggc agttttttta tggacgccta aagggtcgtt gtgggaataa agaaatgtta     240
ttgcgtggca ttctcttgtc tagcgcggcg ttagcaattc tgggactatc atccaggctt     300
ccggcctttt gtgtggcgtg ggccataaac ggtattgcac aggcagctgg atgggccaca     360
tgtctttcaa taatgaatgt ctgggttttt cccaaagagc gtggccgagt gatgggctgg     420
tggtcaacaa acatggcggc aggaggcgtg attggaaatg tctttgcggc ctttctgatt     480 ggaagggat tctcgtggcg tactgctgtt gaggctgaag tggggcttct tttggcagtc     540
ggtggcgtgg tgttgttggc acttgttgag cacccaaatg cggctggttt cccctcggtg     600

-continued

```
cagcaggttg aaggaggtgt ggaatttgcc aagttgtcgt gtgattgcaa ttcggcccct    660
ctgagcaaag acggcgaaat gtatatgaat tcaccaagat caacgagctc ttcgcttgag    720
caaggcatga atcctcggca caaagactat gatgaccatg aggaactctt ctccctcaca    780
tttttgaata ttattcagct ccctggtttg tgtggtatct gtgcatcgta ctttctgtat    840
caacttgtgc gttacggatt tatgttttgg ctcccatatt ttgccgtaca tgaattaaat    900
tataccaccg agtttgcggg gtatgtgacg tgtgcctttg atgttggtgg ggttgtaggc    960
attgtggcat ctgggtactt ttctgactgg atgttccatg gttttggccg aacgcgtgtc   1020
attttgctcc tcactgtagg tatggtgctt gggagctgtt gtcttgctgt cttttctcga   1080
catttttgtgg aaaacgctct tttttttcatg gtggcggtca cctttgttgg ttttttttgcc   1140
tttgctattg attctttggt gtcgggttct ttttttgttgg accacctgga gcacattaag   1200
atggtaaagc aggcaggggc aattagtggt gtggtgggcg gtttcggatc ggcggggtct   1260
acctttcagg gagtcttcac cgccgtgctg atctcaagat catggccaac actgttttac   1320
ggctttggcg tggcaggtgc attggcaggc gtctctctta ttcatccgct ccgcagtgag   1380
ctgctacgag cgcggaaaag gtccgtagtg ttttga                             1416
```

<210> SEQ ID NO 4
<211> LENGTH: 471
<212> TYPE: PRT
<213> ORGANISM: Trypanosoma Cruzi

<400> SEQUENCE: 4

```
Met Phe Arg Thr Tyr Asn Gly Ile Arg Phe Phe Arg Val Phe Leu Thr
1               5                   10                  15

Leu Trp Ile Thr Tyr Ala Ala Tyr Thr Met Val Arg Arg Pro Leu Thr
            20                  25                  30

Val Ala Arg Ala Asp Ile Gln Arg Glu Thr Gly Phe Thr Ser Ala Glu
        35                  40                  45

Thr Ser Leu Val Asp Thr Met Phe Val Phe Ser Tyr Ala Leu Gly Gln
    50                  55                  60

Phe Phe Tyr Gly Arg Leu Lys Gly Arg Cys Gly Asn Lys Glu Met Leu
65                  70                  75                  80

Leu Arg Gly Ile Leu Leu Ser Ser Ala Ala Leu Ala Ile Leu Gly Leu
                85                  90                  95

Ser Ser Arg Leu Pro Ala Phe Cys Val Ala Trp Ala Ile Asn Gly Ile
            100                 105                 110

Ala Gln Ala Ala Gly Trp Ala Thr Cys Leu Ser Ile Met Asn Val Trp
        115                 120                 125

Val Phe Pro Lys Glu Arg Gly Arg Val Met Gly Trp Trp Ser Thr Asn
    130                 135                 140

Met Ala Ala Gly Gly Val Ile Gly Asn Val Phe Ala Ala Phe Leu Ile
145                 150                 155                 160

Gly Arg Gly Phe Ser Trp Arg Thr Ala Val Glu Ala Glu Val Gly Leu
                165                 170                 175

Leu Leu Ala Val Gly Gly Val Val Leu Ala Leu Val Glu His Pro
            180                 185                 190

Asn Ala Ala Gly Phe Pro Ser Val Gln Gln Val Glu Gly Gly Val Glu
        195                 200                 205

Phe Ala Lys Leu Ser Cys Asp Cys Asn Ser Ala Pro Leu Ser Lys Asp
    210                 215                 220

Gly Glu Met Tyr Met Asn Ser Pro Arg Ser Thr Ser Ser Ser Leu Glu
```

```
                225                 230                 235                 240
Gln Gly Met Asn Pro Arg His Lys Asp Tyr Asp Asp His Glu Glu Leu
                245                 250                 255
Phe Ser Leu Thr Phe Leu Asn Ile Ile Gln Leu Pro Gly Leu Cys Gly
                260                 265                 270
Ile Cys Ala Ser Tyr Phe Leu Tyr Gln Leu Val Arg Tyr Gly Phe Met
                275                 280                 285
Phe Trp Leu Pro Tyr Phe Ala Val His Glu Leu Asn Tyr Thr Thr Glu
                290                 295                 300
Phe Ala Gly Tyr Val Thr Cys Ala Phe Asp Val Gly Gly Val Val Gly
305                 310                 315                 320
Ile Val Ala Ser Gly Tyr Phe Ser Asp Trp Met Phe His Gly Phe Gly
                325                 330                 335
Arg Thr Arg Val Ile Leu Leu Leu Thr Val Gly Met Val Leu Gly Ser
                340                 345                 350
Cys Cys Leu Ala Val Phe Ser Arg His Phe Val Glu Asn Ala Leu Phe
                355                 360                 365
Phe Met Val Ala Val Thr Phe Val Gly Phe Phe Ala Phe Ala Ile Asp
                370                 375                 380
Ser Leu Val Ser Gly Ser Phe Leu Leu Asp His Leu Glu His Ile Lys
385                 390                 395                 400
Met Val Lys Gln Ala Gly Ala Ile Ser Gly Val Val Gly Gly Phe Gly
                405                 410                 415
Ser Ala Gly Ser Thr Phe Gln Gly Val Phe Thr Ala Val Leu Ile Ser
                420                 425                 430
Arg Ser Trp Pro Thr Leu Phe Tyr Gly Phe Gly Val Ala Gly Ala Leu
                435                 440                 445
Ala Gly Val Ser Leu Ile His Pro Leu Arg Ser Glu Leu Leu Arg Ala
                450                 455                 460
Arg Lys Arg Ser Val Val Phe
465                 470

<210> SEQ ID NO 5
<211> LENGTH: 1872
<212> TYPE: DNA
<213> ORGANISM: Trypanosoma Cruzi

<400> SEQUENCE: 5
atgctgcttg gctttccctc cgaggtgtgg attacaatga ccgtggagtt tgcggaacgg      60
cttggattct acggaactac ttttatgctc atgacgtact gcacaattat gctgcgttgg     120
agcacgagcg ccgggaatgc tcttatcaac gctttatacg ccctcacacc gttgtctgca     180
tgcgtttctt ctagtgtatc agatgggcgg tggggtcgac cgtactccct tgttgttttc     240
ttgacaacgt atgcggttgg tttatcgatg gtggctcttt cttcgtttcc ccttatgtac     300
ggtgaatttc cactggatcc atctgttctt ggcgttgctt tgtttgctac gggtattttg     360
cttttttgcgt taggttacgg tgggatgaag gtgtgcacga atccgcttat ggccgattgc     420
gtctcggatg cctacaaaga taacgagaca caatgccaag tggtgctttc gcaactttt      480
cgttggattt acgccataac aaatagtgga tctcttattg cattattgt gcccccgcta     540
ctgcggtcct ggatgggcg aagtgttgtg atgggatccg tgacgcacac aacgggttat     600
tactttggat tttcattgtc ggcggtatca tctatattgg ggctatcgct atttgtcatg     660
atgtatcatc gttttcgtcg taacgagcct tcgccctcaa ctgtgctgct acgcactttt     720
```

```
tttcgtgcca ttttcatacg gtggtgcttt gctgtggggc gtattcatga tgaggcattc    780
ctctctgcac atcgctggga tctgattgac tttgccggct actctgtcac ggctaaaaaa    840
agtaccgata cggtggcatc gcatgatgcc ttgtcgggcg cacctgaact ctcggtgaaa    900
ttacggaatt gtacggaaag cggtagtggc agggagctca accaaggcag ggaagccgtt    960
gcaacggagt ggaatgtcaa cgaggcgaag caagacgaca tgccaagtca aagtgcttca   1020
agtgacgccg atgggttgga ccagacctgg atagctaacg caaagatgat tgcctccgtg   1080
tgtcgtgccc tggtcgcaat gccgatctat tggctaatca caaatcagtt tagtaccaac   1140
atgattctac aagcagcaac gacgggtctc ccatcgtata ttccgccaga agtattcaac   1200
aacgtcaatg tcatttccct ccttatctct ttgttgcttt ttgatcgcgt tgtatttcca   1260
tttgttttg ttaacaaaac tccccctgta cgaggacgtg tggtatgtgg ctttgccaca   1320
atgataattt ctatgttttg gtgtggcgtt gtgcagataa atatagatca ccgtggaaaa   1380
tatgacgaga aggatattta tcatttgctt cctggtatga caatggtatc acctctgtgg   1440
ctggttccgc cctacatcat gcagggtgtc gcgagtgcct tggtagatac aaccatcatg   1500
gaggtggtgt acgttgcagc accgacatca atgaagggca cgatgatggc gttctatctc   1560
atggcctcta gcctaagcgg atttcttggt cttgcacttt cacctgcgat gcggccgaaa   1620
aacgcccaaa tagtcatctt ctctctgaca ggggcgcttg tattggtgac agttttgttt   1680
tatcttctta attctcccac ggcagaagct gtgacagaag ctagcgacgg tcaggggacg   1740
gatgtggcgg ctgatcccta cactgtttcc aaggaagaga aggagtgctt gttgttgaag   1800
ggcttttctc gaagtgagaa tgcggcgtac tatggtggtg ttctccatca cagagaggtt   1860
tcacacctgt ga                                                       1872
```

<210> SEQ ID NO 6
<211> LENGTH: 623
<212> TYPE: PRT
<213> ORGANISM: Trypanosoma Cruzi

<400> SEQUENCE: 6

Met Leu Leu Gly Phe Pro Ser Glu Val Trp Ile Thr Met Thr Val Glu
1               5                   10                  15

Phe Ala Glu Arg Leu Gly Phe Tyr Gly Thr Thr Phe Met Leu Met Thr
            20                  25                  30

Tyr Cys Thr Ile Met Leu Arg Trp Ser Thr Ala Gly Asn Ala Leu
        35                  40                  45

Ile Asn Ala Leu Tyr Ala Leu Thr Pro Leu Ser Ala Cys Val Ser Ser
    50                  55                  60

Ser Val Ser Asp Gly Arg Trp Gly Arg Pro Tyr Ser Leu Val Val Phe
65                  70                  75                  80

Leu Thr Thr Tyr Ala Val Gly Leu Ser Met Val Ala Leu Ser Ser Phe
                85                  90                  95

Pro Leu Met Tyr Gly Glu Phe Pro Leu Asp Pro Ser Val Leu Gly Val
            100                 105                 110

Ala Leu Phe Ala Thr Gly Ile Leu Leu Phe Ala Leu Gly Tyr Gly Gly
        115                 120                 125

Met Lys Val Cys Thr Asn Pro Leu Met Ala Asp Cys Val Ser Asp Ala
    130                 135                 140

Tyr Lys Asp Asn Glu Thr Gln Cys Gln Val Val Leu Ser Gln Leu Phe
145                 150                 155                 160

Arg Trp Ile Tyr Ala Ile Thr Asn Ser Gly Ser Leu Ile Gly Ile Ile

```
                165                 170                 175
Val Pro Pro Leu Leu Arg Ser Leu Asp Gly Arg Ser Val Met Gly
            180                 185                 190
Ser Val Thr His Thr Thr Gly Tyr Tyr Phe Gly Phe Ser Leu Ser Ala
            195                 200                 205
Val Ser Ser Ile Leu Gly Leu Ser Leu Phe Val Met Met Tyr His Arg
            210                 215                 220
Phe Arg Arg Asn Glu Pro Ser Pro Ser Thr Val Leu Leu Arg Thr Phe
225                 230                 235                 240
Phe Arg Ala Ile Phe Ile Arg Trp Cys Phe Ala Val Gly Arg Ile His
                245                 250                 255
Asp Glu Ala Phe Leu Ser Ala His Arg Trp Asp Leu Ile Asp Phe Ala
                260                 265                 270
Gly Tyr Ser Val Thr Ala Lys Lys Ser Thr Asp Thr Val Ala Ser His
                275                 280                 285
Asp Ala Leu Ser Gly Ala Pro Glu Leu Ser Val Lys Leu Arg Asn Cys
                290                 295                 300
Thr Glu Ser Gly Ser Gly Arg Glu Leu Asn Gln Gly Arg Glu Ala Val
305                 310                 315                 320
Ala Thr Glu Trp Asn Val Asn Glu Ala Lys Gln Asp Met Pro Ser
                325                 330                 335
Gln Ser Ala Ser Ser Asp Ala Asp Gly Leu Asp Gln Thr Trp Ile Ala
                340                 345                 350
Asn Ala Lys Met Ile Ala Ser Val Cys Arg Ala Leu Val Ala Met Pro
                355                 360                 365
Ile Tyr Trp Leu Ile Thr Asn Gln Phe Ser Thr Asn Met Ile Leu Gln
370                 375                 380
Ala Ala Thr Thr Gly Leu Pro Ser Tyr Ile Pro Pro Glu Val Phe Asn
385                 390                 395                 400
Asn Val Asn Val Ile Ser Leu Leu Ile Ser Leu Leu Leu Phe Asp Arg
                405                 410                 415
Val Val Phe Pro Phe Val Phe Val Asn Lys Thr Pro Pro Val Arg Gly
                420                 425                 430
Arg Val Val Cys Gly Phe Ala Thr Met Ile Ile Ser Met Phe Trp Cys
                435                 440                 445
Gly Val Val Gln Ile Asn Ile Asp His Arg Gly Lys Tyr Asp Glu Lys
                450                 455                 460
Asp Ile Tyr His Leu Leu Pro Gly Met Thr Met Val Ser Pro Leu Trp
465                 470                 475                 480
Leu Val Pro Pro Tyr Ile Met Gln Gly Val Ala Ser Ala Leu Val Asp
                485                 490                 495
Thr Thr Ile Met Glu Val Val Tyr Val Ala Ala Pro Thr Ser Met Lys
                500                 505                 510
Gly Thr Met Met Ala Phe Tyr Leu Met Ala Ser Ser Leu Ser Gly Phe
                515                 520                 525
Leu Gly Leu Ala Leu Ser Pro Ala Met Arg Pro Lys Asn Ala Gln Ile
                530                 535                 540
Val Ile Phe Ser Leu Thr Gly Ala Leu Val Leu Thr Val Leu Phe
545                 550                 555                 560
Tyr Leu Leu Asn Ser Pro Thr Ala Glu Ala Val Thr Glu Ala Ser Asp
                565                 570                 575
Gly Gln Gly Thr Asp Val Ala Ala Asp Pro Tyr Thr Val Ser Lys Glu
                580                 585                 590
```

Glu Lys Glu Cys Leu Leu Leu Lys Gly Phe Ser Arg Ser Glu Asn Ala
            595                 600                 605

Ala Tyr Tyr Gly Gly Val Leu His His Arg Glu Val Ser His Leu
            610                 615                 620

<210> SEQ ID NO 7
<211> LENGTH: 1872
<212> TYPE: DNA
<213> ORGANISM: Trypanosoma Cruzi

<400> SEQUENCE: 7

| | |
|---|---|
| atgctgcttg gctttcccta cgaggtgtgg attacaatga ctgtggagtt tgcggaacgg | 60 |
| cttggattct acggaactac ttttatgctc atgacgtact gcacaattat gctgcgttgg | 120 |
| agcacgagcg ccggaaatgc tcttatcaac gctctatacg ccctcacacc gttgtctgca | 180 |
| tgcgtttctt ctagtgtatc agatgggcgg tggggtcgac cgtactccct tgttgttttc | 240 |
| ttgacaacgt atgcggttgg tttatcgatg gtggctcttt cttcgtttcc ccttatgtac | 300 |
| ggtgaatttc cattggaccc atctgttctt ggcgttgctt tgtttgctac ggtattttg | 360 |
| cttttttgcgg taggttacgg tgggatgaag gtgtgtacga atccacttat ggccgattgc | 420 |
| gtctcggatg cctacaaaga taacgagaca caatgccaag tggtgctttc gcaactttt | 480 |
| cgttggattt acgccataac aaatagtgga tctcttattg cattattgt gccccctcta | 540 |
| ttgcggtctt tggatgggcg aagtgttgtg atgggatccg tgacgcacac aacaggttat | 600 |
| tactttggat tttcattgtc ggcggtatca tctctcttgg ggctatcgct atttgtcatg | 660 |
| atgtatcatc gttttcgtcg taacgagcct tcgccctcaa ttgtgctgcc acgcatttt | 720 |
| tttcgtgcca ttttcatacg gtggtgcttt gctgtggggc gtattcgtga tgaggcattt | 780 |
| ctctctgcac atcgctggga tctgattgac tttgccggct accctgtcac ggctaacaaa | 840 |
| agtaccgatg cggtggcatc acatgatgtc ttgtcgggcg cacctgacct tcggtgaaa | 900 |
| ttacggaatt gtacggaaag cggtagcggc agggagctca accatggcag gaagccgtc | 960 |
| gcgatggagt ggaacgtcaa cgaggcgaag caagacgaaa tgccaagtca agtgcttca | 1020 |
| attgacgccg atgggttgga ccagacctgg gtagctaacg caaagatgat tgcctccgtg | 1080 |
| tgtcgtgccc tggtcgcaat gccgatctat tggctaatca caatcagtt tagtaccaac | 1140 |
| atgattctac aagcagcaac gacgggtctc ccatcgtata ttccgccaga agtcttcaac | 1200 |
| aacgtcaatg tcatttccct ccttatctct ttgttgcttt ttgatcgcgt tgtatttcca | 1260 |
| tttgtttttg ttaacaaaac tcccctgta cgaggacgtg tggtatgtgg ctttgccaca | 1320 |
| atgataattt ctatgttttg gtgtggcgtt gtgcagataa atatagatca ccgcggaaaa | 1380 |
| tatgacgaga aggatattta tcatttgcat cctggtatga caatggtatc acctctgtgg | 1440 |
| ctggttccgc cctacatcat gcagggtgtc gcgagtgcct tagtagatac aaccatcatg | 1500 |
| gaggtggtgt acgttgcagc accgacatca atgaagggca cgatgatggc gttctatctc | 1560 |
| atgacctcta gcctaagcgg atttcttggt cttgcacttt cacctgcgat gcggccgaaa | 1620 |
| aacgcccaaa tcgtcatctt ctctctgaca ggggcgcttg tattggtgac ggttttgttt | 1680 |
| tatcttctca attctcccac agcagaagct gtgacagaag ctagcgacgg tcaggggacg | 1740 |
| gatgtgtcgg ctggcccctg cactgttcc aaggaagaga agaagtgctt gttgttgaag | 1800 |
| gacttttctc gaagtgagaa tgcggcgtac tatggtggtg ttctccatca caaagaggtt | 1860 |
| tcacacctgt ga | 1872 |

<210> SEQ ID NO 8
<211> LENGTH: 623
<212> TYPE: PRT
<213> ORGANISM: Trypanosoma Cruzi

<400> SEQUENCE: 8

```
Met Leu Leu Gly Phe Pro Tyr Glu Val Trp Ile Thr Met Thr Val Glu
1               5                   10                  15

Phe Ala Glu Arg Leu Gly Phe Tyr Gly Thr Thr Phe Met Leu Met Thr
            20                  25                  30

Tyr Cys Thr Ile Met Leu Arg Trp Ser Thr Ser Ala Gly Asn Ala Leu
        35                  40                  45

Ile Asn Ala Leu Tyr Ala Leu Thr Pro Leu Ser Ala Cys Val Ser Ser
    50                  55                  60

Ser Val Ser Asp Gly Arg Trp Gly Arg Pro Tyr Ser Leu Val Val Phe
65                  70                  75                  80

Leu Thr Thr Tyr Ala Val Gly Leu Ser Met Val Ala Leu Ser Ser Phe
                85                  90                  95

Pro Leu Met Tyr Gly Glu Phe Pro Leu Asp Pro Ser Val Leu Gly Val
            100                 105                 110

Ala Leu Phe Ala Thr Gly Ile Leu Leu Phe Ala Val Gly Tyr Gly Gly
        115                 120                 125

Met Lys Val Cys Thr Asn Pro Leu Met Ala Asp Cys Val Ser Asp Ala
130                 135                 140

Tyr Lys Asp Asn Glu Thr Gln Cys Gln Val Val Leu Ser Gln Leu Phe
145                 150                 155                 160

Arg Trp Ile Tyr Ala Ile Thr Asn Ser Gly Ser Leu Ile Gly Ile Ile
                165                 170                 175

Val Pro Pro Leu Leu Arg Ser Leu Asp Gly Arg Ser Val Val Met Gly
            180                 185                 190

Ser Val Thr His Thr Thr Gly Tyr Tyr Phe Gly Phe Ser Leu Ser Ala
        195                 200                 205

Val Ser Ser Leu Leu Gly Leu Ser Leu Phe Val Met Met Tyr His Arg
    210                 215                 220

Phe Arg Arg Asn Glu Pro Ser Pro Ser Ile Val Leu Pro Arg Ile Phe
225                 230                 235                 240

Phe Arg Ala Ile Phe Ile Arg Trp Cys Phe Ala Val Gly Arg Ile Arg
                245                 250                 255

Asp Glu Ala Phe Leu Ser Ala His Arg Trp Asp Leu Ile Asp Phe Ala
            260                 265                 270

Gly Tyr Pro Val Thr Ala Asn Lys Ser Thr Asp Ala Val Ala Ser His
        275                 280                 285

Asp Val Leu Ser Gly Ala Pro Asp Leu Ser Val Lys Leu Arg Asn Cys
    290                 295                 300

Thr Glu Ser Gly Ser Gly Arg Glu Leu Asn His Gly Arg Glu Ala Val
305                 310                 315                 320

Ala Met Glu Trp Asn Val Asn Glu Ala Lys Gln Asp Glu Met Pro Ser
                325                 330                 335

Gln Ser Ala Ser Ile Asp Ala Asp Gly Leu Asp Gln Thr Trp Val Ala
            340                 345                 350

Asn Ala Lys Met Ile Ala Ser Val Cys Arg Ala Leu Val Ala Met Pro
        355                 360                 365

Ile Tyr Trp Leu Ile Thr Asn Gln Phe Ser Thr Asn Met Ile Leu Gln
    370                 375                 380
```

```
Ala Ala Thr Thr Gly Leu Pro Ser Tyr Ile Pro Pro Glu Val Phe Asn
385                 390                 395                 400

Asn Val Asn Val Ile Ser Leu Leu Ile Ser Leu Leu Leu Phe Asp Arg
            405                 410                 415

Val Val Phe Pro Phe Val Phe Val Asn Lys Thr Pro Val Arg Gly
        420                 425                 430

Arg Val Val Cys Gly Phe Ala Thr Met Ile Ile Ser Met Phe Trp Cys
            435                 440                 445

Gly Val Val Gln Ile Asn Ile Asp His Arg Gly Lys Tyr Asp Glu Lys
        450                 455                 460

Asp Ile Tyr His Leu His Pro Gly Met Thr Met Val Ser Pro Leu Trp
465                 470                 475                 480

Leu Val Pro Pro Tyr Ile Met Gln Gly Val Ala Ser Ala Leu Val Asp
                485                 490                 495

Thr Thr Ile Met Glu Val Val Tyr Val Ala Ala Pro Thr Ser Met Lys
            500                 505                 510

Gly Thr Met Met Ala Phe Tyr Leu Met Thr Ser Ser Leu Ser Gly Phe
        515                 520                 525

Leu Gly Leu Ala Leu Ser Pro Ala Met Arg Pro Lys Asn Ala Gln Ile
530                 535                 540

Val Ile Phe Ser Leu Thr Gly Ala Leu Val Leu Val Thr Val Leu Phe
545                 550                 555                 560

Tyr Leu Leu Asn Ser Pro Thr Ala Glu Ala Val Thr Glu Ala Ser Asp
                565                 570                 575

Gly Gln Gly Thr Asp Val Ser Ala Gly Pro Cys Thr Val Ser Lys Glu
            580                 585                 590

Glu Lys Lys Cys Leu Leu Leu Lys Asp Phe Ser Arg Ser Glu Asn Ala
        595                 600                 605

Ala Tyr Tyr Gly Gly Val Leu His His Lys Glu Val Ser His Leu
610                 615                 620

<210> SEQ ID NO 9
<211> LENGTH: 1545
<212> TYPE: DNA
<213> ORGANISM: Trypanosoma Cruzi

<400> SEQUENCE: 9
atgtcttccg gcgccagtac ggagggaaaa tgcttgccag aagacagcga tatttcgtgg    60
gtattgatat catcagttct tgtcttagga atgatgccgg gtttgggttt ttttgaggct   120
ggtcttcttc gttccaaaaa tacaacttcc gtttttgccc agatattcag tggatgtgcc   180
gttctttccg tactatgggt gtgtgccgga tattccctaa cgatgggtag gtcggcagga   240
ggtaaaggta ttatcggtac ttttcggcgt gcctttatga tgaatgtgga ctacaatact   300
tgctatggtg gaactgtgat tccagaggct tgtttgcct tttttcagat gatgtttgca   360
acaataacac cacttcttat gactggtgcc tatgcagagc gattggcctt cgcccatt    420 ttgttttta caattttatg ggagattatt gtgtactttt tgtcgctca ctgggtttgg   480 gcacctgagg gctggatgcg cggaatgggt gtacaagatt tgctggagg cattgtgatt   540 catgttactc tggggttttc atcattagta tgcgccgttg ttttgggacg tcgtcgagat   600
tttcatattc atagagggga agctccttac tcctctcttc ctcttacttg tattggggct   660
accatgctat ggactggatg gtttgggttc aatgggggga gtgctcttca gtctggaaaa   720
ggagccgttt atgctgtgat taattcgcag gtggcagcgg ccgtttgttc atgctgcttt   780
```

-continued

```
ctgttttttc atatgctgcg aaccaaaaag gcgagtctta ttgccatgat aaatggagcc    840
attgcaggtt tggctggtat tactcctact tccggctata ttactgtacc tagctctatt    900
atatgtgctt tttttattgc agttttttgca accgtatctg tttatttgat caaacacaaa    960
ttacgcattg atgatgcgct tgatgtttcc agcatccatg gggtacccgg attggttggg   1020
gccgttttta ttgggttttc cggatcttca gccgtcggtg gtgcggatgg gttgctttac   1080
ggaggaggta taagactact tggattacaa tgcctgggtt gtattgtggc tgctacatgg   1140
gcaggatttt ggacatttgt tatattactt atcattgggc gattttatcg actacgagta   1200
acagacgaac aggaacacca cgggctagat cacggacagc atagcgaagt tgcatggatt   1260
ttacaggcgt caaatgttgg aggagacgct taccaataaa agaaccgaaa acgcgtaaaa   1320
caggttcgaa acagcagcct gtttattgga gaaactggca catacattgt agaaaaagaa   1380
aggggtgact ctatcttggt agttgagaga gtgaataatg acgaagttga cattgatgac   1440
gaccctcgcg aagagggttt taatacaatg actttggcag tgaatgctga tgcaaggaat   1500
gagattacta ccgatattga cgaacggcta atcaattgca gctga                   1545
```

<210> SEQ ID NO 10
<211> LENGTH: 514
<212> TYPE: PRT
<213> ORGANISM: Trypanosoma Cruzi

<400> SEQUENCE: 10

```
Met Ser Ser Gly Ala Ser Thr Glu Gly Lys Cys Leu Pro Glu Asp Ser
1               5                   10                  15

Asp Ile Ser Trp Val Leu Ile Ser Ser Val Leu Val Leu Gly Met Met
            20                  25                  30

Pro Gly Leu Gly Phe Phe Glu Ala Gly Leu Leu Arg Ser Lys Asn Thr
        35                  40                  45

Thr Ser Val Phe Ala Gln Ile Phe Ser Gly Cys Ala Val Leu Ser Val
    50                  55                  60

Leu Trp Val Cys Ala Gly Tyr Ser Leu Thr Met Gly Arg Ser Ala Gly
65                  70                  75                  80

Gly Lys Gly Ile Ile Gly Thr Phe Arg Arg Ala Phe Met Met Asn Val
                85                  90                  95

Asp Tyr Asn Thr Cys Tyr Gly Gly Thr Val Ile Pro Glu Ala Leu Phe
            100                 105                 110

Ala Phe Phe Gln Met Met Phe Ala Thr Ile Thr Pro Leu Leu Met Thr
        115                 120                 125

Gly Ala Tyr Ala Glu Arg Leu Ala Phe Arg Pro Phe Leu Phe Phe Thr
    130                 135                 140

Ile Leu Trp Glu Ile Ile Val Tyr Phe Phe Val Ala His Trp Val Trp
145                 150                 155                 160

Ala Pro Glu Gly Trp Met Arg Gly Met Gly Val Gln Asp Phe Ala Gly
                165                 170                 175

Gly Ile Val Ile His Val Thr Ala Gly Val Ser Ser Leu Val Cys Ala
            180                 185                 190

Val Val Leu Gly Arg Arg Arg Asp Phe His Ile His Arg Gly Glu Ala
        195                 200                 205

Pro Tyr Ser Ser Leu Pro Leu Thr Cys Ile Gly Ala Thr Met Leu Trp
    210                 215                 220

Thr Gly Trp Phe Gly Phe Asn Gly Gly Ser Ala Leu Gln Ser Gly Lys
225                 230                 235                 240
```

-continued

Gly Ala Val Tyr Ala Val Ile Asn Ser Gln Val Ala Ala Val Cys
            245                 250                 255

Ser Cys Cys Phe Leu Phe Phe His Met Leu Arg Thr Lys Lys Ala Ser
            260                 265                 270

Leu Ile Ala Met Ile Asn Gly Ala Ile Ala Gly Leu Ala Gly Ile Thr
            275                 280                 285

Pro Thr Ser Gly Tyr Ile Thr Val Pro Ser Ser Ile Ile Cys Ala Phe
            290                 295                 300

Phe Ile Ala Val Phe Ala Thr Val Ser Val Tyr Leu Ile Lys His Lys
305                 310                 315                 320

Leu Arg Ile Asp Asp Ala Leu Asp Val Ser Ser Ile His Gly Val Pro
            325                 330                 335

Gly Leu Val Gly Ala Val Phe Ile Gly Phe Ser Gly Ser Ser Ala Val
            340                 345                 350

Gly Gly Ala Asp Gly Leu Leu Tyr Gly Gly Gly Ile Arg Leu Leu Gly
            355                 360                 365

Leu Gln Cys Leu Gly Cys Ile Val Ala Ala Thr Trp Ala Gly Phe Trp
            370                 375                 380

Thr Phe Val Ile Leu Leu Ile Ile Gly Arg Phe Tyr Arg Leu Arg Val
385                 390                 395                 400

Thr Asp Glu Gln Glu His His Gly Leu Asp His Gly Gln His Ser Glu
            405                 410                 415

Val Ala Trp Ile Leu Gln Ala Ser Asn Val Gly Gly Asp Ala Leu Pro
            420                 425                 430

Ile Lys Asn Arg Lys Arg Val Lys Gln Val Arg Asn Ser Ser Leu Phe
            435                 440                 445

Ile Gly Glu Thr Gly Thr Tyr Ile Val Glu Lys Glu Arg Gly Asp Ser
            450                 455                 460

Ile Leu Val Val Glu Arg Val Asn Asn Asp Glu Val Asp Ile Asp Asp
465                 470                 475                 480

Asp Pro Arg Glu Glu Gly Phe Asn Thr Met Thr Leu Ala Val Asn Ala
            485                 490                 495

Asp Ala Arg Asn Glu Ile Thr Thr Asp Ile Asp Glu Arg Leu Ile Asn
            500                 505                 510

Cys Ser

<210> SEQ ID NO 11
<211> LENGTH: 1152
<212> TYPE: DNA
<213> ORGANISM: Trypanosoma Cruzi

<400> SEQUENCE: 11
atgaaaccag acacaatggc gaattatcgc acagaaccca cgtgtgaaat gacgagtgtg      60
acggtggact tttctcataa tgattcgcat cgtgacgaga gtgcgatca ctctttggag      120 aggaataagc acagcgatga ggaaccacat gagaatgacg atgtgaatgc ggagcacaag     180
ttgcttgcag atccgtcagg gatcaaactg gggaaataca ttattccgcc tcgcgtggtg    240
gcaccaatct gcgcgcttct tattgttgcg ggtggggtgc ttttttgcctt tacgacccca    300 atgaaaaaca tgaccccgaa gccgtggaat cgcatctcgg cgttgattgg ctggattttac   360 ttcttggcgt gggggggtttc cttcttgcca cagttgtact tcaacatgcg ccggcggagt   420
gttgtgggac agagctttga atttgtttac ctgaacattt tcggattctt gttgttactcc   480 gtttatacgc tgtgtttcta cgccaataac aacgtgaata atatgtacaa ggatcgccac    540

-continued

```
aatgggtcga gtaacaatgt ggctctgaat gatgttgttt ttgcggtgta tgcattggca    600
tgctgccttt tgaatggctt gcagattatc ttctttgatc gtggcggcca aagatgagc     660
atccttgcga ctggactcat cgtccttata tttttttgtca ttgtgctgtg gacctgcctc   720
attgctgggg gcgtgaagcg tgacgtcttc ttcaattatc tcgaccttct gtacggcctg    780
agtttggtca aactgggcat cagtattgtg aagtacgtgc cgcaggtata cctaaactac    840
aaacggaaat gcacgattgg gtggaacatc tggaacattt tgctcgactt cacaggcggt    900
atactaagca tcttacagga ggtgattgac agctgggtga cgagcgactg ggatggcatg    960
acaggcaacc ccgtaaaatt tgctctcggt tccgtaagca tattgtacga ccttgtcttc   1020
tttgtacagc acttttttgct ttacaatgag aacaataagc ggcttgcctt gccggatcat  1080
gtccacacgc gcgaggttgg agcgtcagag aaaagagaag agcaaaaaaa cgaaaacgaa   1140
aaaatgattt aa                                                        1152
```

<210> SEQ ID NO 12
<211> LENGTH: 383
<212> TYPE: PRT
<213> ORGANISM: Trypanosoma Cruzi

<400> SEQUENCE: 12

```
Met Lys Pro Asp Thr Met Ala Asn Tyr Arg Thr Glu Pro Thr Cys Glu
  1               5                  10                  15
Met Thr Ser Val Thr Val Asp Phe Ser His Asn Asp Ser His Arg Asp
             20                  25                  30
Glu Lys Cys Asp His Ser Leu Glu Arg Asn Lys His Ser Asp Glu Glu
         35                  40                  45
Pro His Glu Asn Asp Asp Val Asn Ala Glu His Lys Leu Leu Ala Asp
     50                  55                  60
Pro Ser Gly Ile Lys Leu Gly Lys Tyr Ile Ile Pro Pro Arg Val Val
 65                  70                  75                  80
Ala Pro Ile Cys Ala Leu Leu Ile Val Ala Gly Gly Val Leu Phe Ala
                 85                  90                  95
Phe Thr Thr Pro Met Lys Asn Asn Asp Pro Lys Pro Trp Asn Arg Ile
            100                 105                 110
Ser Ala Leu Ile Gly Trp Ile Tyr Phe Leu Ala Trp Gly Val Ser Phe
        115                 120                 125
Leu Pro Gln Leu Tyr Phe Asn Met Arg Arg Arg Ser Val Val Gly Gln
    130                 135                 140
Ser Phe Glu Phe Val Tyr Leu Asn Ile Phe Gly Phe Leu Cys Tyr Ser
145                 150                 155                 160
Val Tyr Thr Leu Cys Phe Tyr Ala Asn Asn Asn Val Asn Asn Met Tyr
                165                 170                 175
Lys Asp Arg His Asn Gly Ser Ser Asn Asn Val Ala Leu Asn Asp Val
            180                 185                 190
Val Phe Ala Val Tyr Ala Leu Ala Cys Cys Leu Leu Asn Gly Leu Gln
        195                 200                 205
Ile Ile Phe Phe Asp Arg Gly Gly Gln Lys Met Ser Ile Leu Ala Thr
    210                 215                 220
Gly Leu Ile Val Leu Ile Phe Phe Val Ile Val Leu Trp Thr Cys Leu
225                 230                 235                 240
Ile Ala Gly Gly Val Lys Arg Asp Val Phe Phe Asn Tyr Leu Asp Leu
                245                 250                 255
```

```
Leu Tyr Gly Leu Ser Leu Val Lys Leu Gly Ile Ser Ile Val Lys Tyr
            260                 265                 270

Val Pro Gln Val Tyr Leu Asn Tyr Lys Arg Lys Cys Thr Ile Gly Trp
        275                 280                 285

Asn Ile Trp Asn Ile Leu Leu Asp Phe Thr Gly Gly Ile Leu Ser Ile
    290                 295                 300

Leu Gln Glu Val Ile Asp Ser Trp Val Thr Ser Asp Trp Asp Gly Met
305                 310                 315                 320

Thr Gly Asn Pro Val Lys Phe Ala Leu Gly Ser Val Ser Ile Leu Tyr
                325                 330                 335

Asp Leu Val Phe Phe Val Gln His Phe Leu Leu Tyr Asn Glu Asn Asn
            340                 345                 350

Lys Arg Leu Ala Leu Pro Asp His Val His Thr Arg Glu Val Gly Ala
        355                 360                 365

Ser Glu Lys Arg Glu Glu Gln Lys Asn Glu Asn Glu Lys Met Ile
    370                 375                 380

<210> SEQ ID NO 13
<211> LENGTH: 1509
<212> TYPE: DNA
<213> ORGANISM: Trypanosoma Cruzi

<400> SEQUENCE: 13
atgacccaca cattcacgga cccgctggtg gatctcgcat tcgtctcctt tcagtacccc      60
catggtggcg gtggtcggc gggcgggata cgcgatgtca gtgttcgcgt gaacggcggg     120
gatcgagttc tcgtcgtggg gcacaacggt agtggaaagt caacgctttt gtccgtcatt     180
gcggggcggc gaaaggcgtc gagtggccgc gccactgtgc tgggttccga cgcctttgat     240
gacacgcgtc tgcagcagca tgtgacgctt attggtcgac cgtggccaac agaggctttc     300
tttgccacca ctgtcgacca ggtaacctct aaggcgccgc tgccggaaag gaagcgaagc     360
gtggcggatg ctcttcatct tgatttaggg cgtgccgtta gcaatatgag ttcgggggag     420
agacggcggg tgcagattct tcacggtttg ttgcagaagt cgtttgttta tttgctggac     480
gaatgtagca cggacatcga cattgcggag cgaatgaccg tgttggatct tgtgcggtca     540
gagtgtgttg ttggtgacag ctgttgcttg tatgcgactc atatttttga tggtgtgagt     600
gactgggcaa cgcacctctt gctgatgcag ggaggcatgg tcgttgattt caaaagggta     660
tctgatctca atgcaccttt ggaggtgttt gtgtgccact tcctcacgag gcgtcatcga     720
gaccttttg attacactag caagcggatg cccgtgaaag aggcatacaa tgacgattgg     780
aagggagggg gcacagtgac cgccctgcct tcggaaaaag aggctgttat tgtctgtgac     840
cgactacaat acagaaacat attccgtaat ctttccttca cggtttacag ggggatcgt      900
gtgttgctct gtggttgcaa tggggccggg aagtcaactt tgctgaaaat gatgggcggg     960
aagcagttct caacaacag caatggatca ctccgtatta ttgggaaatc ctgttacgat    1020
gatatgacgc taaacggcct tgttgcgttt ggtggtgaat ggtgggatac cgcaccgccg    1080
ggtgaaatgc acgtgcacga gatgctgcaa cttcaaacac cacgggcgga gtggttgtgc    1140
aaagttcttg gagtggactt gtcgtgggac gtccgccata tttctacggg tgagcagaaa    1200
catgtgcagc ttctacttca cttactcgag gacaagcccg ttattctgct ggatgaggcc    1260
acatctgatc ttgatctcga ccagcgacag gagttgttat catttctgta caatgagagt    1320
gccaaccgag gtgtgactgt tgtgtacgca actcacatat ttggcgggct ggagaattgg    1380
ccaacagctg tcatgatgct tgaccggacc acgcaaggcc tccatgccat gtggcgtgga    1440
```
agcgatgtga atgggcaga aattacaagg gagcttatcg ctttaaaggg aagggaaaat    1500
gtcaaatag                                                          1509

<210> SEQ ID NO 14
<211> LENGTH: 502
<212> TYPE: PRT
<213> ORGANISM: Trypanosoma Cruzi

<400> SEQUENCE: 14

Met Thr His Thr Phe Thr Asp Pro Leu Val Asp Leu Ala Phe Val Ser
1               5                   10                  15

Phe Gln Tyr Pro His Gly Gly Gly Ser Ala Gly Gly Ile Arg Asp
            20                  25                  30

Val Ser Val Arg Val Asn Gly Gly Asp Arg Val Leu Val Gly His
        35                  40                  45

Asn Gly Ser Gly Lys Ser Thr Leu Leu Ser Val Ile Ala Gly Arg Arg
    50                  55                  60

Lys Ala Ser Ser Gly Arg Ala Thr Val Leu Gly Ser Asp Ala Phe Asp
65                  70                  75                  80

Asp Thr Arg Leu Gln Gln His Val Thr Leu Ile Gly Arg Pro Trp Pro
            85                  90                  95

Thr Glu Ala Phe Phe Ala Thr Thr Val Asp Gln Val Thr Ser Lys Ala
            100                 105                 110

Pro Leu Pro Glu Arg Lys Arg Ser Val Ala Asp Ala Leu His Leu Asp
        115                 120                 125

Leu Gly Arg Ala Val Ser Asn Met Ser Ser Gly Glu Arg Arg Arg Val
    130                 135                 140

Gln Ile Leu His Gly Leu Leu Gln Lys Ser Phe Val Tyr Leu Leu Asp
145                 150                 155                 160

Glu Cys Ser Thr Asp Ile Asp Ile Ala Glu Arg Met Thr Val Leu Asp
            165                 170                 175

Leu Val Arg Ser Glu Cys Val Val Gly Asp Ser Cys Cys Leu Tyr Ala
        180                 185                 190

Thr His Ile Phe Asp Gly Val Ser Asp Trp Ala Thr His Leu Leu Leu
    195                 200                 205

Met Gln Gly Gly Met Val Val Asp Phe Lys Arg Val Ser Asp Leu Asn
210                 215                 220

Ala Pro Leu Glu Val Phe Val Cys His Phe Leu Thr Arg Arg His Arg
225                 230                 235                 240

Asp Leu Phe Asp Tyr Thr Ser Lys Arg Met Pro Val Lys Glu Ala Tyr
            245                 250                 255

Asn Asp Asp Trp Lys Gly Gly Gly Thr Val Thr Ala Leu Pro Ser Glu
        260                 265                 270

Lys Glu Ala Val Ile Val Cys Asp Arg Leu Gln Tyr Arg Asn Ile Phe
    275                 280                 285

Arg Asn Leu Ser Phe Thr Val Tyr Arg Gly Asp Arg Val Leu Leu Cys
290                 295                 300

Gly Cys Asn Gly Ala Gly Lys Ser Thr Leu Leu Lys Met Met Gly Gly
305                 310                 315                 320

Lys Gln Phe Phe Asn Asn Ser Asn Gly Ser Leu Arg Ile Ile Gly Lys
            325                 330                 335

Ser Cys Tyr Asp Asp Met Thr Leu Asn Gly Leu Val Ala Phe Gly Gly
        340                 345                 350

-continued

```
Glu Trp Trp Asp Thr Ala Pro Pro Gly Glu Met His Val His Glu Met
        355                 360                 365

Leu Gln Leu Gln Thr Pro Arg Ala Glu Trp Leu Cys Lys Val Leu Gly
    370                 375                 380

Val Asp Leu Ser Trp Asp Val Arg His Ile Ser Thr Gly Glu Gln Lys
385                 390                 395                 400

His Val Gln Leu Leu Leu His Leu Leu Glu Asp Lys Pro Val Ile Leu
                405                 410                 415

Leu Asp Glu Ala Thr Ser Asp Leu Asp Leu Asp Gln Arg Gln Glu Leu
                420                 425                 430

Leu Ser Phe Leu Tyr Asn Glu Ser Ala Asn Arg Gly Val Thr Val Val
        435                 440                 445

Tyr Ala Thr His Ile Phe Gly Gly Leu Glu Asn Trp Pro Thr Ala Val
        450                 455                 460

Met Met Leu Asp Arg Thr Thr Gln Gly Leu His Ala Met Trp Arg Gly
465                 470                 475                 480

Ser Asp Val Lys Trp Ala Glu Ile Thr Arg Glu Leu Ile Ala Leu Lys
                485                 490                 495

Gly Arg Glu Asn Val Lys
                500
```

TRYPANOSOMA CRUZI PROTEOME COMPOSITIONS AND METHODS

This application claims the benefit of U.S. Provisional Application Ser. No. 60/699,736, filed Jul. 15, 2005, which is incorporated herein by reference in its entirety.

STATEMENT OF GOVERNMENT RIGHTS

This invention was made with government support under grants from the National Institutes of Health, Grant No. P01 AI044979, Grant No. P41-RR018502, and Grant No. P41-RR005351. The U.S. Government has certain rights in this invention.

BACKGROUND OF THE INVENTION

Blood feeding (hemophagic) arthropod pests are of great concern not only because of their annoying and often painful bites, but more importantly because many can also be vectors (carriers) of pathogenic (disease causing) organisms, that seriously injure or kill humans and domestic animals, e.g., encephalitis, tularema, Lyme disease, malaria, yellow fever, Chagas disease, bubonic plague, murine typhus, tapeworms, Rocky Mountain fever, etc.

*Trypanosoma cruzi* causes Chagas disease in humans. Acute infection can be lethal, but the disease usually evolves into a chronic stage, accompanied in 25-30% of cases by severe debilitation and ultimately death. It is estimated that 16-18 million people are infected, primarily in Central and South America, with 21,000 deaths reported each year.

*Trypanosoma cruzi* exists in four morphologically and biologically distinct forms during its cycle of development in mammals and insects: metacyclic trypomastigotes, amastigotes, trypomastigotes and epimastigotes (FIG. 1). The amastigote and trypomastigote stages are sometimes referred to as the "mammalian stages," and the metacyclic trypomastigote and epimastigote stages are sometimes referred to as the "insect stages." Metacyclic trypomastigotes develop in the hind gut of triatomine insect vectors and initiate infection in a wide variety of animal species, including humans. *T. cruzi* trypomastigotes are normally transmitted from the reduviid bug to the mammalian host via the vector feces after a bug bite, but also by ingestion of contaminated food, or following blood transfusion or organ donation. Trypomastigotes can invade several types of host cells. In host cells trypomastigotes convert to replicative aflagellate amastigote forms which reside in the host cell cytoplasm. Following multiple rounds of binary fission, the aflagellate amastigotes convert into non-dividing flagellated trypomastigotes that burst from the host cell and circulate in the bloodstream. The extracellular trypomastigotes can initiate another round of host cell infection, invading other host cells and thus spread the infection throughout the body. Alternatively, trypomastigotes acquired by a reduviid vector during a blood meal convert to epimastigote forms, which replicate in the insect gut before eventually differentiating into infective metacyclic trypomastigote forms.

The bulk of human transmission of *T. cruzi* is a consequence of infestation of sub-standard housing by *T. cruzi*-infected reduviid bugs wherein these insects feed on the inhabitants that generally include not only humans but also dogs and other pets and livestock animals. Field and modeling studies suggest that dogs in particular are the major reservoir for *T. cruzi* in most houses and most insects become infected, and thus capable of transmitting infection to humans, by feeding on *T. cruzi* infected dogs (Cohen et al., Science. 2001 Jul 27; 293(5530):694-8).

Historical attempts to develop vaccines for parasitic diseases have been largely futile, and there is a critical lack of methods for diagnosis and treatment for *T. cruzi* in particular. Improved drugs and vaccines for the treatment and prevention of *T. cruzi* infection are needed, as are improved diagnostic methods.

SUMMARY OF THE INVENTION

Proteomic analysis of *T. cruzi* has identified many new molecular targets suitable for use in diagnosis of Chagas disease, in drug development, in antibody production, and in the production of vaccines, including live vaccines.

In one aspect, the invention provides a monoclonal antibody or fragment thereof that binds to a highly abundant *T. cruzi* polypeptide. Preferably the polypeptide is selected from polypeptides encoded by the *T. cruzi* genes listed in Table 9. The polypeptide is preferably expressed by at least one of a *T. cruzi* amastigote or trypomastigote. Also provided by the invention is a hybridoma that produces the monoclonal antibody of the invention.

In another aspect, the invention provides antiserum that contains a plurality of antibodies, each of which binds a highly abundant *T. cruzi* polypeptide. Preferably, the antiserum contains at least 5 different antibodies, more preferably at least 10 different antibodies, each of which binds a *T. cruzi* polypeptide selected from polypeptides encoded by the *T. cruzi* genes listed in Table 9.

In yet another aspect, the invention provides a method for diagnosing *T. cruzi* infection in a subject. Preferably, the subject is a dog or a mammal. A body fluid or tissue of the subject is contacted with at least one monoclonal antibody described herein, and binding of the monoclonal antibody to a component in the body fluid or tissue of the subject is detected, wherein binding is indicative of *T. cruzi* infection. Optionally, the body fluid or tissue of the subject is contacted with a plurality of monoclonal antibodies so as to capture a plurality of *T. cruzi* antigens. Alternatively, the body fluid or tissue can be contacted with the antiserum that contains polyclonal antibodies that bind a *T. cruzi* protein, and binding of the antiserum to a component in the body fluid or tissue of the subject is detected. The *T. cruzi* antigens can be detected using immunoassay or spectroscopy, any other convenient method.

In yet another aspect, the invention provides a method for diagnosing *T. cruzi* infection in a subject, preferably a human or a dog, that involves contacting at least one highly abundant *T. cruzi* protein with a bodily fluid or tissue of a mammal; and detecting an immune response to the protein in the mammal. The immune response is preferably evidenced by the presence of an antibody, a B cell or a T cell in the bodily fluid or tissue, and is indicative of a *T. cruzi* infection.

In yet another aspect, the invention provides a vaccine that contains at least one component selected from the group consisting of (a) a immunogenic *T. cruzi* polypeptide and (b) a polynucleotide comprising a nucleotide coding region encoding a immunogenic *T. cruzi* polypeptide. The *T. cruzi* polypeptide is preferably a highly abundant polypeptide, more preferably a polypeptide encoded by a *T. cruzi* gene listed in Table 9. The invention further includes a method for immunizing a mammal against *T. cruzi* comprising administering the vaccine to the mammal, preferably a human or a dog. Immunization can be therapeutic or prophylactic.

In another aspect, the invention provides a genetically engineered *T. cruzi* in which protein expression from a gene involved in energy metabolism has been reduced or eliminated. In one embodiment of the genetically engineered *T.* cruzi, the gene is involved in fatty acid metabolism or transport or histidine metabolism or transport. For example, the protein expressed by the gene (prior to knockout) is a fatty acid transporter, a histidine transporter, or an acyl transferase. In another embodiment, protein expression from a from a transporter gene, preferably a transporter gene unique to *T. cruzi*, has been reduced or eliminated in the genetically engineered *T. cruzi*. The transporter gene can be selected from the transporter genes listed in Example II. In a preferred embodiment, the protein expressed by the transporter gene includes a transporter protein that transports a metabolite into *T. cruzi*. The protein expressed by the transporter gene is optionally located in the cell membrane of the *T. cruzi*. Preferred transporter protein candidates for gene knockouts include a fatty acid transporter protein, a glucose-6-phosphate transporter protein, and a histidine transporter protein.

The invention further includes a method for immunizing a mammal against *T. cruzi* that includes administering to the mammal, preferably a human or a dog, a live vaccine that contains genetically engineered *T. cruzi* as described herein. The live vaccine can be administered by injection or ingestion, without limitation.

In another aspect, the invention provides a method for treating a *T. cruzi* infection in a mammal. The method involves administering to the mammal, preferably a human or a dog, a compound that targets a membrane-bound transporter protein expressed by a *T. cruzi* amastigote, preferably a fatty acid transporter protein or glucose-6-phosphate transporter protein. Optionally, the compound binds to the transporter protein to inhibit or prevent transport of a metabolite from the host cytoplasm into *T. cruzi*.

Unless otherwise specified, "a," "an," "the," and "at least one" are used interchangeably and mean one or more than one.

BRIEF DESCRIPTION OF THE DRAWINGS

The patent or application file contains at least one drawing executed in color. Copies of this patent or patent application with color drawings will be provided by the Office upon request and payment of the necessary fee.

FIG. 1 shows the life cycle and a summary of the major findings of proteome analysis in *T. cruzi*. *T. cruzi* trypomastigotes circulate in the blood of infected hosts, including humans, but must enter host cells (often muscle cells) and convert to amastigote forms in order to replicate. Triatomine bug vectors become infected by ingesting trypomastigotes during the course of a bloodmeal on infected mammalian hosts. Conversion of the trypomastigotes into epimastigotes, replication of these epimastigotes, and their eventual transformation into metacyclic trypomastigotes, occurs in the insect gut. Metacyclic trypomastigotes initiate new infection in mammals when infected insects are ingested or by deposition of parasites in the feces, usually during a bloodmeal.

FIG. 2 shows stage specific detection of trans-sialidase (ts) proteins. Cumulative protein scores based upon summing the Mascot scores (Matrix Science, Ltd., London, United Kingdom) for all high confidence peptides are used to display the stage-regulated expression of ts proteins detected in the proteomes. Peptides matching to 223 members of the ts family clustered into 50 protein groups; only the top-scoring protein for each protein group is shown. Most ts proteins are detected exclusively in one stage (A=amastigote, T=trypomastigote, M=metacyclic trypomastigote, E=epimastigote).

FIG. 3 shows a flow chart of protein isolation, separation, and analysis of four *T cruzi* developmental stages. a, Peptides were isolated from either whole-cell lysates or subcellular preparations from the four *T. cruzi* developmental stages. b, Chromatograms resulting from separation of peptides from a whole-cell lysate of $1\times10^9$ trypomastigotes (RPLC1, SCX) and cytoplasmic preparation of $1\times10^9$ amastigotes (RPLC2). c, All peptide fractions were analyzed independently by LC-MS/MS. The left panel is a total ion chromatogram from LC-MS/MS analysis of a single trypomastigote peptide fraction. A single mass spectrum (middle panel) measured at 55 minutes (TIC) contained a peptide with a mass at 759.37 m/z, which was further analyzed by tandem mass spectrometry (right panel). d, Following filtering, recalibration and database searching the peptide was identified as peptide AAAEAAATATEAAEAAK (SEQ ID NO:1) from a newly annotated MASP protein family member. Iterative database searching against a normal and random database allowed identification of the MASP protein family member and 2,748 other proteins at less than 1% error rate. e, Non-matching spectra were used to identify an additional 79 unannotated genes form the *T. cruzi* ORF database.

FIG. 4 shows stage specific detection of retrotransposon hot spot (RHS) proteins. Cumulative protein scores based upon summing the Mascot scores for all high confidence peptides are used to display the stage-regulated expression of RHS proteins detected in the proteomes. Only the top-scoring protein for each protein group is shown. In contrast to ts proteins, most of which are detected exclusively in one stage (see FIG. 2), most RHS proteins are detected in multiple stages (A=amastigote, T=trypomastigote, M=metacyclic trypomastigote, E=epimastigote).

FIG. 5 shows MS/MS sampling by life cycle stage (Table 3).

Figures 6, 6A, 6B, 6C, 6D, 6E, 6F, 6G:
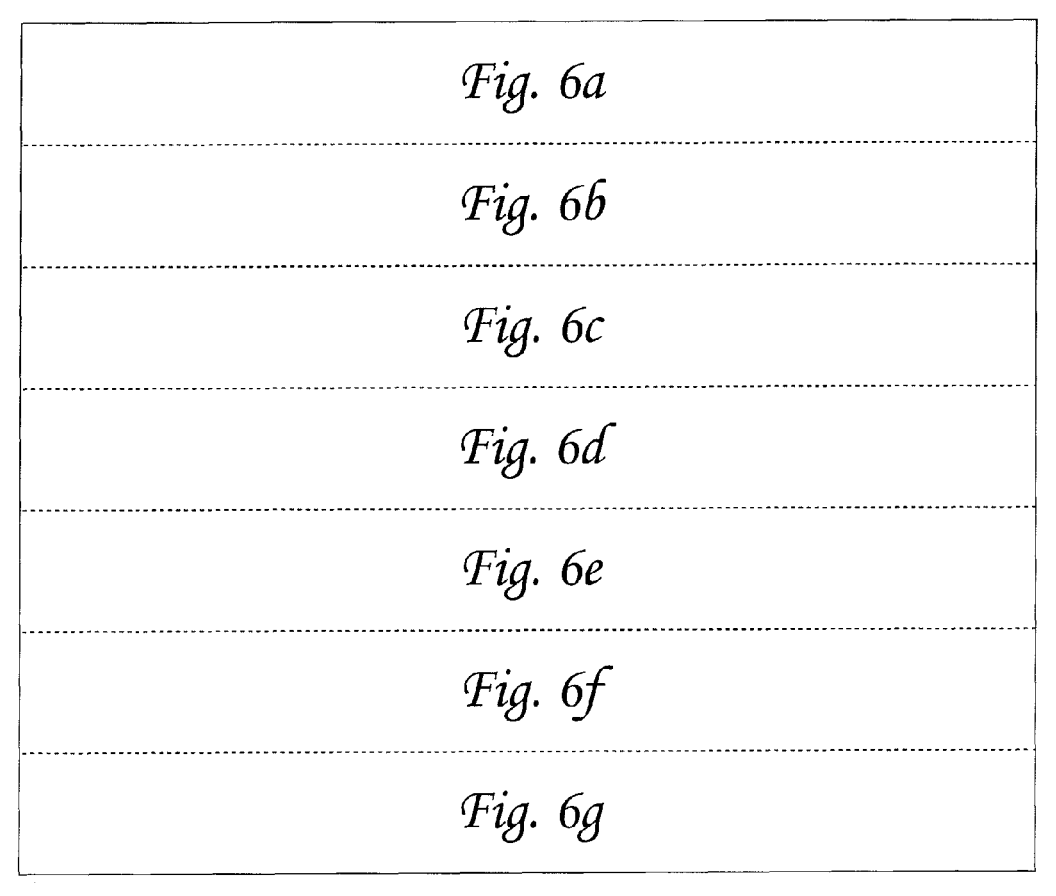

FIG. 6 shows *T. cruzi* expressed proteins identified from TSK-TSC annotated genome (Table 4). The TSK-TSC is an international consortium (Tri-Tryp genome consortium) comprising The Institute for Genomic Research (TIGR, USA), the Seattle Biomedical Research Institute (SBRI, USA) and the Karolinska Institute (KI, Sweden). El-Sayed et al. (2005) *Science,* 309, 409-415. The *T. cruzi* database TcruziDB (Center for Tropical & Global Emerging Diseases (CTGED), University of Georgia, Athens, Ga.) is an integrated post-genomics database established in 2003 as a flat-file database with tools for mining the unannotated sequence reads and preliminary contig assemblies emerging from the Tri-Tryp genome consortium. The TcruziDB houses the recently published assembled genomic contigs and annotation provided by the genome consortium in a relational database supported by the Genomics Unified Schema (GUS) architecture. Agüero et al., Nucleic Acids Research 2006 34(Database Issue):D428-D431; doi:10.1093/nar/gkj108.

Figures 7, 7A, 7B, 7C, 7D, 7E, 7F, 7G:
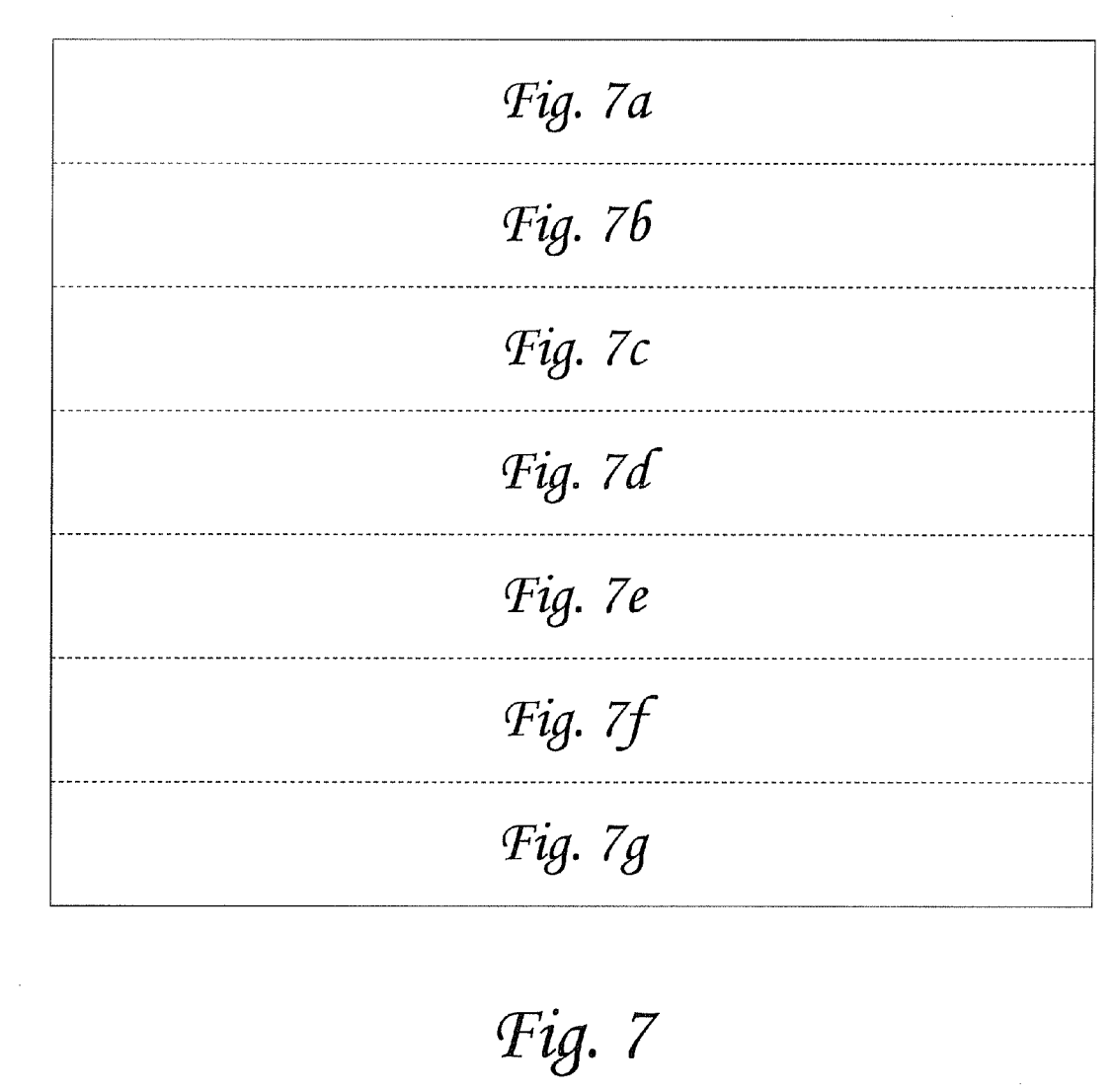
Figure 7E:
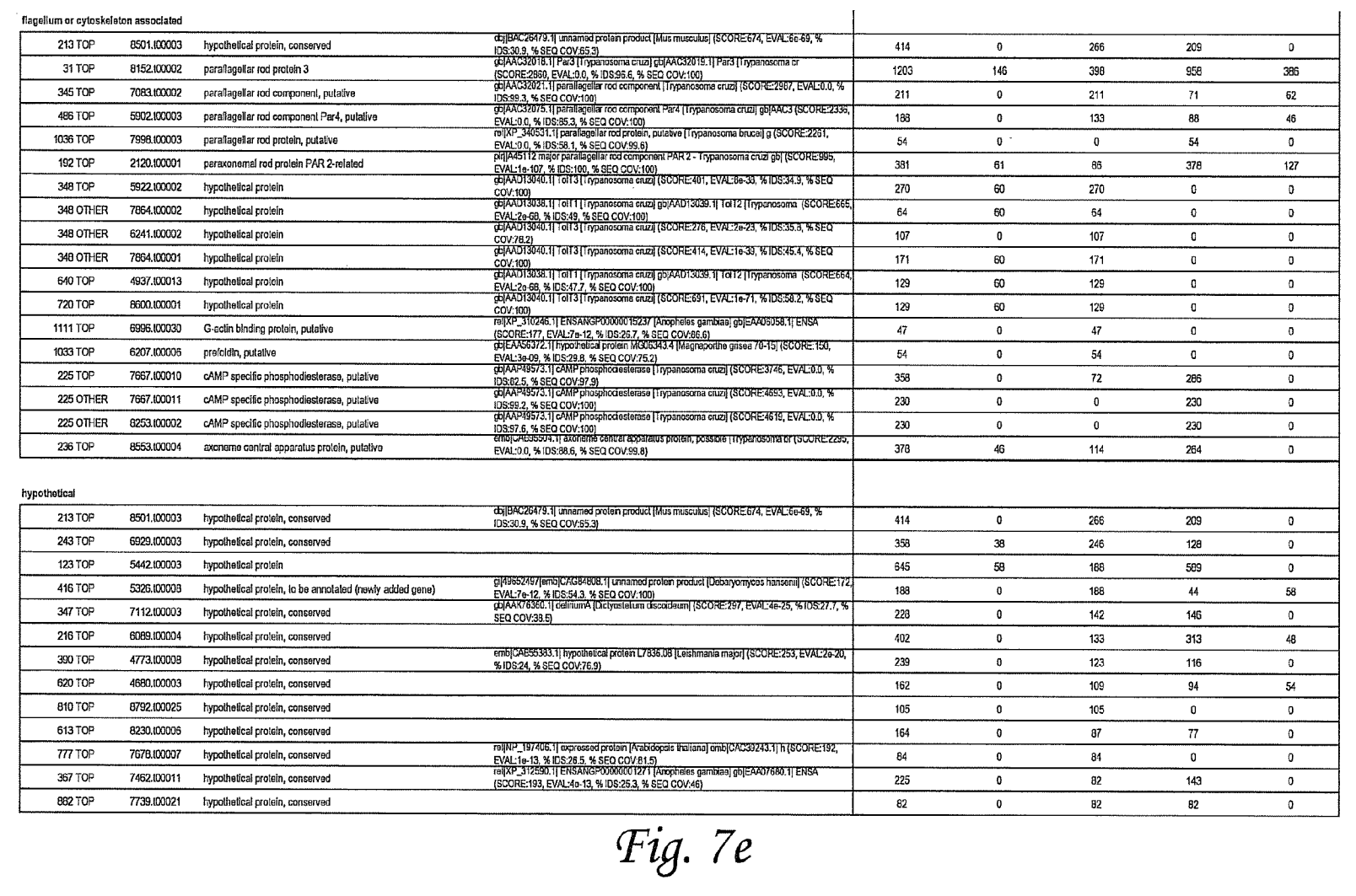

FIG. 7 shows selected stage-regulated *T. cruzi* proteins (Table 5).

FIG. 8 shows the correlation of microarray and proteomic data for selected proteins (Table 6).

Figures 9, 9A, 9B, 9C, 9D, 9E, 9F, 9G:
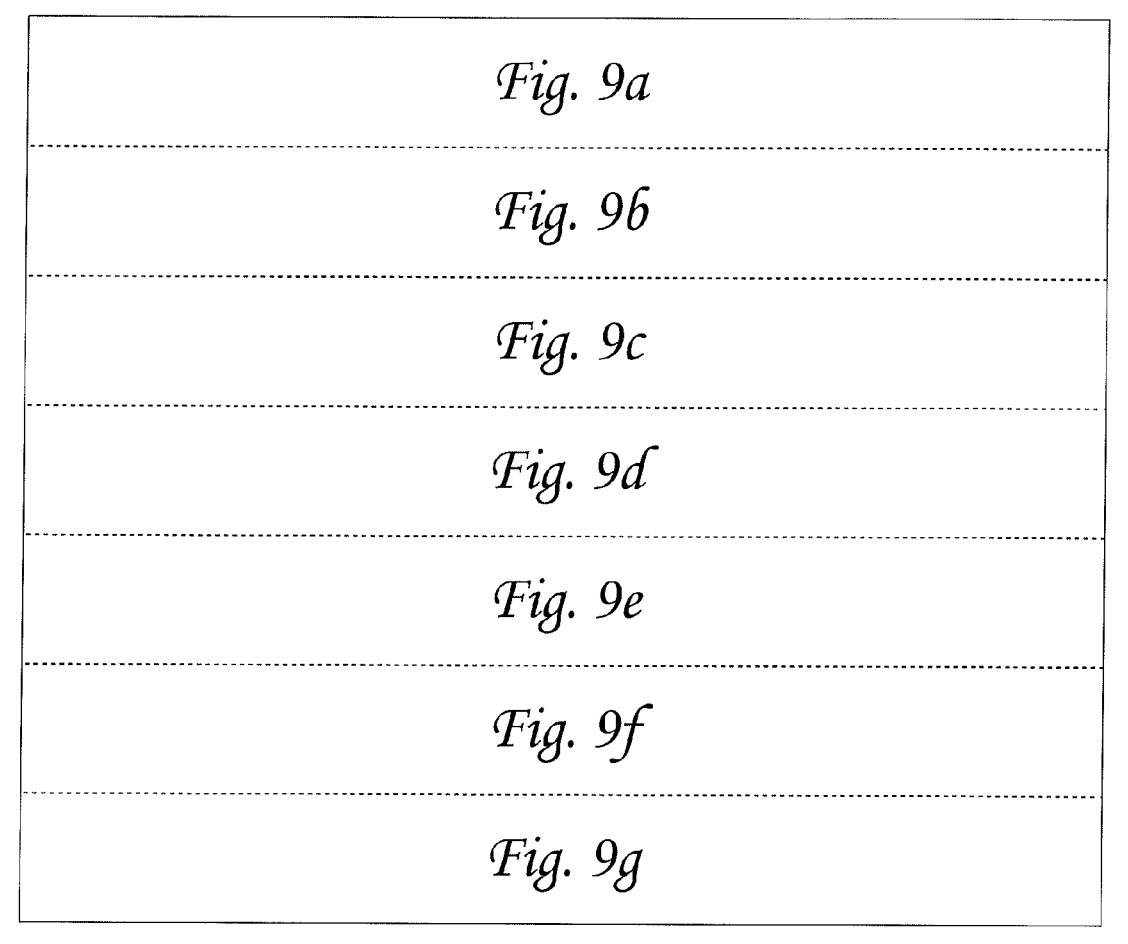

FIG. 9 shows *T. cruzi* expressed proteins with selected modifications identified from TSK-TSC annotated genome (Table 7).

FIG. 10 shows *T. cruzi* expressed proteins identified from the ORF database (ORFans) (Table 8).

FIG. 11 shows genes involved in *T. cruzi* histidine metabolism.

DETAILED DESCRIPTION OF ILLUSTRATIVE EMBODIMENTS

Proteomic analysis of *T. cruzi*, the causative agent of Chagas disease, was used to analyze, identify and quantify the proteins expressed in each of the four life cycle stages of *T.*

*cruzi*: metacyclic trypomastigotes, amastigotes, trypomastigotes and epimastigotes. FIG. 7 (Table 5) shows selected stage-regulated *T. cruzi* proteins.

Analysis of the proteomes of *T. cruzi* reveals the operation of several previously undocumented stage-specific pathways that represent targets for drug intervention as well as new resources for vaccine development. Among the most interesting of these are the proposed pathways for energy generation in amastigotes and epimastigotes Additionally, the identification of proteins expressed in abundance in trypomastigotes and amastigotes of *T. cruzi* provides a substantial new resource of candidates for both vaccine and drug development.

As noted earlier, in infected mammalian hosts, *T. cruzi* is present in the amastigote and the trypomastigote stages. Previously, certain trans-sialidases were identified as excellent vaccine candidates due to their abundance and their preferential expression in the *T. cruzi* amastigote (U.S. Pat. No. 6,875,584, issued Apr. 5, 2005 to Tarleton et al.). The discovery of additional stage-related *T. cruzi* proteins opens up new avenues for diagnosis, treatment and prevention of *T. cruzi* infection. A protein that is detected primarily or exclusively in trypomastigotes and/or amastigotes, but not in metacyclic or epimastigote forms of *T. cruzi* is particularly preferred for use in the diagnostic or therapeutic applications as described herein. For example, polypeptide or polynucleotide vaccines that incorporate the amino acid sequence (or DNA encoding such sequence) of one or more amastigote stage proteins (or subunits thereof) are expected to stimulate a protective an immune response in the host. Such an immune response can be prophylactic (thereby preventing infection) or therapeutic (inhibiting or destroying *T. cruzi* already present in the host organism). See, for example, U.S. Pat. No. 6,875,584, issued Apr. 5, 2005 to Tarleton et al., for additional descriptions of therapeutic and prophylactic vaccines. The development of live vaccines is also facilitated, as discussed below.

Further, stage-regulated proteins, especially enzymes, are excellent candidates for drug development. Screening assays can be used to identify inhibitors of stage-related enzymes present in the mammalian host or the insect vectors, which are then useful as therapeutic agents to treat *T. cruzi* infection.

Finally, human serum can be assayed for the presence of one or more stage-related *T. cruzi* protein, particularly those that are more abundant, to provide a more accurate diagnosis of *T. cruzi* infection. Typically, this assay is an immunoassay, and the human serum is contacted with one or more antibodies against a stage-regulated *T. cruzi* protein, as described in more detail elsewhere herein.

Surprisingly, analysis of the distribution of expressed proteins gave rise to the identification of different energy sources for individual parasite stages. The four parasite stages were found to use distinct energy sources, including histidine for stages present in the insect vectors and fatty acids by intracellular amastigotes. The transition of trypomastigotes to amastigotes in mammalian hosts appears to be accompanied by a dramatic shift from carbohydrate to lipid dependent energy metabolism. Thus, enzymes involved in *T. cruzi* fatty acid metabolism, particular β-oxidation of fatty acids, represent excellent knockout candidates for the production of a live, avirulent strain of *T. cruzi*. A genetically engineered *T. cruzi* that is not able to metabolize fatty acids could, for example, be administered to a dog or other non-human host on which the insect vector feeds and which normally facilitates contact between the parasite and a human host. Alternatively, a live vaccine could be administered directly to a human subject, either prophylactically (in advance of infection) or therapeutically (after infection has occurred).

Enzymes involved in *T. cruzi* fatty acid metabolism are also excellent candidates for use in the development of therapeutic agents, as inhibitors of these enzymes may deprive *T. cruzi* of it energy source in the mammalian host, thereby ameliorating or eliminating *T. cruzi* infection.

*T. cruzi* is present in insect vectors in the metacyclic trypomastigote and epimastigote stages. Thus, enzymes involved in *T. cruzi* histidine metabolism represent excellent targets for the development of drugs to be introduced into the insect vector, for example in the form of a bait.

Antibodies, Diagnostics and Passive Immunization

In one aspect, the invention is directed to an antibody that recognizes any of the gene products set forth herein. Antibodies may be used for diagnostic or therapeutic purposes (i.e., passive immunization). Preferably, the antibody recognizes at least one protein that is highly expressed in *T. cruzi* amastigotes and/or trypomastigotes. Exemplary highly abundant proteins are listed in Table 9, Example III. Examples include Tc00.1047053507029.30 (heat shock 70 kDa protein [7180.t00003]), Tc00.1047053506297.190 (pyruvate phosphate dikinase, putative [6890.t00019]), Tc00.1047053506563.40 (beta tubulin, putative [6998.t00004]), Tc00.1047053506585.40 (glucose-regulated protein 78, putative [7009.t00004]), Tc00.1047053511215.119 (69 kDa paraflagellar rod protein, putative [8623.t00012]). The antibody may recognize a plurality of highly abundant proteins. It should be noted that gene names and numbers refer to their designations in TcruziDB.org or GeneDb.org public databases.

Also preferred as recognition targets, particularly for diagnostic antibodies, are proteins that are preferentially expressed in a particular life cycle stage, i.e., stage-regulated proteins. In a particularly preferred embodiment, the antibody recognizes a *T. cruzi* protein that is preferentially or exclusively expressed in *T. cruzi* amastigotes or trypomastigotes. Other examples of proteins that can be used as antigens to develop polyclonal antibodies or monoclonal antibodies are exemplified in FIGS. 5-10 and Examples II and III.

The antibody provided by the invention can be polyclonal. Polyclonal antibodies can be made, for example, by injection of one or more proteins of interest into a host, preferably a mammalian or avian host, then isolating the polyclonal antibodies from the blood of the host. Serum from the immunized animal is collected and treated according to known procedures. See, e.g., Jurgens et al. (1985) J. Chrom. 348:363-370. If serum containing polyclonal antibodies is used, the polyclonal antibodies can be purified by immunoaffinity chromatography, using known procedures. In the case of an avian host, the antibodies can be readily isolated from the egg of the host as well.

In one embodiment, the invention provides polyclonal antiserum from a mammalian or avian host that contains one or more antibodies, e.g., IgG or IgY, to a protein expressed by *T. cruzi*. The antiserum is particularly useful for diagnostic purposes; the antiserum can be contacted with the blood or tissue of a subject suspected of being infected by *T. cruzi*, and the resulting mixture can be analyzed for the presence of *T. cruzi* antigens that interact with polyclonal antibodies in the antiserum of the mammalian or avian host. Preferably, the animal used to raise the polyclonal antibodies is a chicken, a mouse, a rat or a rabbit; more preferably it is a rabbit. The antiserum from one or more rabbits can be pooled to provide a diagnostic composition, which can then be used to detect the presence of *T. cruzi* proteins from human serum.

The antibody provided by the invention can be monoclonal. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., Hybridoma Techniques (1980); Hammerling et al., Monoclonal Antibodies and T-cell Hybridomas (1981); Kennett et al., Monoclonal Antibodies (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the desired protein, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response.

Optionally, the antibodies are generated in other species and "humanized" for administration in humans, particularly if the antibodies are to be used for therapeutic purposes (passive immunization). Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies against a *T. cruzi* antigen may be useful for diagnostic and/or therapeutic purposes. When used as a diagnostic, the antibody is contacted with a bodily fluid or tissue of a subject suspected of being infected by *T. cruzi* in an immunoassay using methods well known to the art, and the presence or absence of a *T. cruzi* antigen is detected. The antibody may indicate the infection state of the subject (e.g., past exposure, current acute infection, or current chronic infection). Bodily fluids include, but are not limited to, blood, plasma, serum, urine, saliva and the like. Tissues include, but are not limited to, adipose tissue and muscle tissue. When used as a therapeutic agent, antibodies confer passive immunization. A therapeutic antibody can be administered to a subject prior to infection (prophylactically) or as a treatment after infection. An antibody administered to a mammalian subject, such as a human or a dog, can boost the subject's immunity in fighting the infections.

*T. cruzi* antigens can also be detected using non-immunological methods. For example, they can be detected using spectroscopy, e.g., MS/MS spectroscopy. A bodily fluid or tissue of the mammal is contacted with either a polyclonal antiserum, or a plurality of monoclonal antibodies to capture a plurality of *T. cruzi* antigens from the fluid or tissue. The captured antigens can be subjected to a secondary detection step, e.g., exposure to a secondary antibody in an immunoassay such as a sandwich assay or ELISA, or analysis via spectroscopy, e.g., mass spectrometry. This allows for the screening of the fluid or tissue for the presence of certain proteins or peptides of *T. cruzi* origin, and use of these "biomarkers" as a diagnostic indicator.

Diagnostics Based on Detection of Host Immune Response

The *T. cruzi* proteins described herein, or portions thereof, can be contacted with a bodily fluid or tissue of a mammal to detect immune responses to these proteins in the mammal, such as a dog or a human. Either or both antibody or T cell responses can be detected in this manner. Assays for detecting T cell responses are well known in the art. Human T cells that recognize a *T. cruzi* antigen can thereby indicate infection status.

Polypeptide and Polynucleotide Vaccines

Any of the proteins described herein that are immunogenic can be used to generate a polypeptide vaccine or polynucleotide vaccine according to methods well-known in the art. Preferably, the polypeptides used to generate a vaccine are those that are highly abundant (e.g., proteins listed in Table 9, Example III) and/or stage-regulated. In particular, proteins shown herein to be preferentially expressed in and secreted by the amastigote and/or trypomastigote stage in the life cycle are especially suitable for use in vaccines, as these proteins would be expected to generate the best protective immune responses. Whole proteins or immunogenic subunits, or DNA encoding them, may be used. Additional suitable proteins include those described in U.S. Pat. No. 6,875,584, issued Apr. 5, 2005 to Tarleton et al. Preferably, the vaccine is a multicomponent vaccine.

Thus, in another aspect, the invention is directed to a vaccine that is effective to treat or prevent infection of a mammal by *T. cruzi*. The vaccine can be a polypeptide vaccine or a polynucleotide vaccine, and can include one or more immunogenic components. A polynucleotide vaccine contains one or more polynucleotides containing a nucleotide coding region that encodes an immunogenic polypeptide derived from *T. cruzi*. Analogously, a polypeptide vaccine contains one or more immunogenic polypeptides derived from *T. cruzi*.

A vaccine effective for the prevention of infection in an organism is one that elicits the production of a protective immune response in an organism exposed to the vaccine. The vaccine of the invention preferably stimulates an antibody response or a cell-mediated immune response, or both, in the mammal to which it is administered. The goal of vaccination is to elicit a population of lymphocytes, which upon subsequent exposure to the disease causing agent, such as a parasite, proliferate and produce antibodies and/or effector cells specific to the parasite, resulting in protection against lethal infections. Antibody responses and cell-mediated responses, as well as methods of making a vaccine, are described in U.S. Pat. No. 6,875,584, issued Apr. 5, 2005 to Tarleton et al.

The invention should be understood as including methods of making and using the polypeptide and polynucleotide vaccines.

Polynucleotide Vaccine

The polynucleotide vaccine of the invention includes at least one nucleotide coding region encoding an immunogenic polypeptide component from *T. cruzi*. When it contains two or more nucleotide coding regions, the polynucleotide vaccine is referred to herein as a "multicomponent" polynucleotide vaccine. It is desirable to limit the number of different immunogenic polypeptides encoded by the nucleotide coding regions in the polynucleotide vaccine; however, it is nonetheless contemplated that a polynucleotide vaccine that generates the highest level of protection will encode 10 or more immunogenic polypeptides. The polynucleotide vaccine can contain DNA, RNA, a modified nucleic acid, or any combination thereof. Preferably, the vaccine comprises one or more cloning or expression vectors; more preferably, the vaccine comprises a plurality of expression vectors each capable of autonomous expression of a nucleotide coding region in a mammalian cell to produce at least one immunogenic polypeptide or cytokine, as further described below. An expression vector preferably includes a eukaryotic promoter sequence, more preferably the nucleotide sequence of a strong eukaryotic promoter, operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular eukaryotic promoter, and a wide variety are known; preferably, however, the expression vector contains a CMV or RSV promoter. The promoter can be, but need not be, heterologous with respect to the host cell. The promoter used is preferably a constitutive promoter.

A vector useful in the present invention can be circular or linear, single-stranded or double stranded and can be a plasmid, cosmid, or episome but is preferably a plasmid. In a preferred embodiment, each nucleotide coding region (whether it encodes an immunogenic polypeptide or a cytokine) is on a separate vector; however, it is to be understood that one or more coding regions can be present on a single vector, and these coding regions can be under the control of a single or multiple promoters.

There are numerous plasmids known to those of ordinary skill in the art useful for the production of polynucleotide vaccines. Preferred embodiments of the polynucleotide vaccine of the invention employ constructs using the plasmids VR1012 (Vical Inc., San Diego, Calif.), pCMVI.UBF3/2 (S. Johnston, University of Texas) or pcDNA3.1 (InVitrogen Corporation, Carlsbad, Calif.) as the vector. Plasmids VR1012 and pCMVI.UBF3/2 are particularly preferred. In addition, the vector construct can contain immunostimulatory sequences (ISS), such as unmethylated dCpG motifs, that stimulate the animal's immune system. Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to control or eliminate the *T. cruzi* infection. The polynucleotide vaccine can also encode a fusion product containing the antigenic polypeptide and a molecule, such as CTLA-4, that directs the fusion product to antigen-presenting cells inside the host. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell. An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri, Yersinia ruckerii*, and *Listeria monocytogenes*. Preferably, the polynucleotide is a vector, such as a plasmid, that is capable of autologous expression of the nucleotide sequence encoding the immunogenic polypeptide.

Plasmids and other delivery systems are made using techniques well-known in the art of molecular biology, as exemplified in the following examples. The invention should be understood as including methods of making and using the polynucleotide vaccine.

One particularly preferred embodiment of the polynucleotide vaccine of the invention includes a nucleotide coding region encoding a cytokine, to provide additional stimulation to the immune system of the mammal. Preferably, the polynucleotide vaccine further includes at least one nucleotide coding region encoding a cytokine. Preferred cytokines include interleukin-12 (IL-12), granulocyte-macrophage colony-stimulating factor (GM-CSF), interleukin-6 (IL-6), interleukin-18 (IL-18), γ-interferon, α,β-interferons, and chemokines. Especially preferred cytokines include IL-12 and GM-CSF.

Polypeptide Vaccine

The polypeptide vaccine of the invention includes at least one immunogenic polypeptide from *T. cruzi*. As with the polynucleotide vaccine, it is desirable to limit the number of different immunogenic polypeptides supplied in the vaccine; however, it is nonetheless contemplated that a polypeptide vaccine that generates the highest level of protection will contain 10 or more immunogenic polypeptides.

A particularly preferred embodiment of the polypeptide vaccine of the invention includes an immunogenic polypeptide that contains a membrane translocating sequence, to facilitate introduction of the polypeptide into the mammalian cell and subsequent stimulation of the cell-mediated immune response. Because a $CD8^+$ T cell response cannot normally be directly triggered by the administration of a conventional protein subunit vaccine, the immunogenic polypeptides contained in the polypeptide vaccine preferably include one or more membrane transporting sequences (MTS) fused to their N-terminus or C-terminus or both. A membrane translocating sequence allows for transport of the immunogenic polypeptide across a lipid bilayer, allowing it to be delivered to the inside of a mammalian cell.

A polypeptide vaccine of the invention is optionally adjuvanted using any convenient and effective adjuvant, as known to one of skill in the art.

Immunogenic Polypeptide

An "immunogenic *T. cruzi* polypeptide" is a polypeptide from *T. cruzi* that elicits in a mammalian host an antibody-mediated immune response (i.e., a "B cell" response or humoral immunity), a cell-mediated immune response (i.e., a "T cell" response), or a combination thereof. A cell-mediated response can involve the mobilization helper T cells, cytotoxic T-lymphocytes (CTLs), or both. Preferably, an immunogenic polypeptide elicits one or more of an antibody-mediated response, a $CD4^+$ Th1-mediated response (Th1: type 1 helper T cell), and a $CD8^+$ T cell response. It should be understood that the term "polypeptide" as used herein refers to a polymer of amino acids and does not refer to a specific length of a polymer of amino acids. Thus, for example, the terms peptide, oligopeptide, and protein are included within the definition of polypeptide.

An immunogenic polypeptide for use in a *T. cruzi* vaccine according to the invention is preferably a highly abundant protein, and/or a stage-regulated protein. It is preferably a polypeptide that is expressed by *T. cruzi* in the extracellular (trypomastigote) stage, in the intracellular (amastigote) stage, or during both stages of the life cycle. Preferably, the immunogenic polypeptide is expressed by a *T. cruzi* amastigote; more preferably, it is expressed by the amastigote in the early stage of infection, within about 24 hours from initial infection. Also preferably, the immunogenic polypeptide is a membrane surface-associated polypeptide or a secreted polypeptide. Surface associated-immunogenic polypeptides include, for example, *T. cruzi* proteins that are anchored to the plasma membrane by glycosylphosphotidylinositols, or GPIs, and those that have transmembrane domains or are otherwise embedded in the plasma membrane. One class of polypeptides that exemplifies immunogenic polypeptides is the trans-sialidase family of proteins, such as TSA-1 (*T. cruzi* Peru; D. Fouts et al., Mol. Biochem. Parasitol. 46:189-200 (1991); GenBank Acc. Number M58466), ASP-1 and ASP-2 (*T. cruzi* Brazil; M. Santos et al., Mol. Biochem. Parasitol. 86:1-11 (1997); GenBank Acc. Number U74494)) and ASP-2 (*T. cruzi* Brazil; H. Low et al., Mol. Biochem. Parasitol. 88:137-149 (1997); GenBank Acc. Number U77951), which are found in both secreted and surface-displayed forms; other examples are proteins that are secreted upon entry of the host cells by *T. cruzi*, such as the hemolysin, and the Lyt1 protein (porin).

Another example of an immunogenic polypeptide is a *T. cruzi* transporter protein, such as a histidine transporter protein. Dogs could be immunized with a vaccine that comprises a histidine transporter protein or immunogenic subunit thereof (or polynucleotide encoding the transporter protein or subunit thereof), thereby generating an antibody response in the dogs. When the insects take a blood meal they ingest the antibodies, which can then block the uptake of nutrients by the ingested parasites, thereby preventing establishment of the infection in the insect. In a preferred embodiment, dogs can be dually vaccinated—with a live vaccine (e.g., based on a disruption to a fatty acid pathway gene, as described in more detail below) to keep the dogs from getting infected with a pathogenic *T. cruzi*, and also with a polypeptide or polynucleotide vaccine that produces a host immune response to a histidine transporter gene to ultimately prevent *T. cruzi* from establishing an infection in the insects vector.

An immunogenic polypeptide used in the compositions of the invention is not limited to a naturally occurring immunogenic *T. cruzi* polypeptide; it can include an immunogenic fragment or immunogenic analog of a *T. cruzi* polypeptide. Likewise the immunogenic polypeptide can be a multivalent polypeptide that has been engineered to include epitopes obtained from different immunogenic polypeptides of *T. cruzi*. An immunogenic analog of an immunogenic *T. cruzi* polypeptide is a polypeptide having one or more amino acid substitutions, insertions, or deletions relative to an immunogenic *T. cruzi* polypeptide, such that immunogenicity is not entirely eliminated. Substitutes for an amino acid are preferably conservative and are selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Immunogenic fragments of an immunogenic *T. cruzi* polypeptide are immunogenic *T. cruzi* polypeptides that are truncated at either or both of the N-terminus or C-terminus, without eliminating immunogenicity. Preferably, an immunogenic fragment contains an epitope recognized by a host T cell. Fragments of an immunogenic *T. cruzi* protein contain at least about eight amino acids, preferably at least about 12 amino acids, more preferably at least about 20 amino acids.

Live Vaccine

Gene knockouts can be made for the production of genetically engineered vaccine strains of *T. cruzi*. The strains can be combined in a pharmaceutically acceptable carrier and used as "live vaccines." Live vaccines are straightforward to generate and manufacture and are likely to be more effective than killed vaccines, polypeptide vaccines, or polynucleotide vaccines in inducing protection. Preferably, the genetically engineered *T. cruzi* is avirulent. Use of a whole cell vaccine has the additional advantage of potentially serving as an adjuvant, thus further stimulating the immune system of the recipient.

"Knocking out" a gene is to be construed broadly to include reducing or eliminating the production of the encoded gene product. Thus, a gene knockout can, for example, by made by site directed mutation, insertional mutagenesis, frameshift mutation, or deletion of all or part of the gene or regulatory regions controlling expression of the gene.

Because *T. cruzi* is known to be present in mammals in the intracellular amastigote stage, the invention contemplates identifying *T. cruzi* gene products that are involved in processes that are exclusive to and/or critical to the intracellular amastigote stage of *T. cruzi*. An avirulent live vaccine can be generated by knocking out one or more genes encoding these products. These knockout strains can be conveniently made in epimastigote stages of *T. cruzi* (where the stage-regulated genes products are, by definition, not necessary), then these epimastigotes can be converted in culture to infective trypomastigotes. The resulting genetically engineered infective trypomastigotes can be used as live vaccines. It is expected that upon infection of mammalian host cells by these trypomastigotes, *T. cruzi* parasites will convert to amastigotes but will then be unable to develop further, eventually dying in the host cell. These dead and dying parasites will stimulate immune responses that are expected to provide protective immunity to the host.

A live vaccine can be administered to any mammalian host, for example to humans or dogs. Administration of the live vaccine to dogs is expected to be especially advantageous, as it is expected to reduce that incidence of humans becoming infected as a result of their close proximity with dogs in the home where transmission often occurs. Insects feed on the dogs, and in many cultures dogs are in the house with the humans, thereby facilitating contact between the insect vector and a human host. If dogs are vaccinated with a genetically engineered avirulent strain of *T. cruzi* such that they mount an immune response, then the dogs should be immune from infection by *T. cruzi*, and they will not serve as a reservoir of *T. cruzi* infection that can be transmitted to humans via the insect vector.

Genes expressed in the amastigote stage represent good candidates for knockout (vaccine development) or for drug development; some are not present to any significant extent in other stages. Genes that have low copy number are preferred, as they fewer copies need to be "knocked out." Examples of particularly good candidates include genes encoding transporter proteins that are unique to *T. cruzi* (see Example II). Preferably, the protein expressed by the transporter gene comprises a transporter protein that transports a metabolite into *T. cruzi*, and is optionally located in the *T. cruzi* cell membrane. As noted below, particularly preferred transporter protein knockout candidates include a fatty acid transporter protein, a glucose-6-phosphate transporter protein, and a histidine transporter protein. A preferred genetically engineered *T. cruzi* is thus one wherein protein expression from a *T. cruzi* gene, preferably a stage-regulated, and/or transporter gene, has been reduced or eliminated.

As described in Example I, we have identified energy sources used by *T. cruzi* in an insect vector and in a mammalian host. In the insect vector, we identified a unique pattern of utilizing histidine as energy source. This leads to the possibility of interfering with the growth or infectivity of *T. cruzi* inside the insect. Genes in this pathway are exemplified in Example II. They represent attractive targets for the development of drugs that inhibit the production or activity of the gene product.

In mammalian hosts *T. cruzi* is an intracellular human parasite which uses fatty acids as an energy source. Thus, a genetically engineered *T. cruzi* useful as a live vaccine can be made by knocking out one or more genes involved in fatty acid biosynthesis or transport in *T. cruzi* (see Examples I and II).

One example of a knockout candidate is a gene that encodes a fatty acid transporter. Muscle cells and adipocytes get 90% of their energy from fatty acids; they are big transporters of fatty acids. Interestingly, *T. cruzi* prefers to lodge in these cells. The transporter was not yet detected in proteome analysis even though other enzymes in the pathway of β-oxidation of fatty acids were detected, indicating that this pathway is active. We postulate that the reason for failing to detect the transporter protein may be an abundance issue and/or may be because it is an integral membrane protein so that it is lost in the sample analysis process (see Example I). The fatty acid transporter seen from genomic analysis is a membrane protein with strong homology with other fatty acid transporters. They are low copy number in *T. cruzi*, and thus constitute a good knockout candidate. In the proteomic analysis described in Example I, this gene was identified as hypothetical gene based on homology to known fatty acid transporters.

Another example of a gene that can be knocked out to make a live vaccine is an acyl transferase. This enzyme either participates in the transport process, and/or it is involved in adding Co-enzyme A to substrates during fatty acid metabolism. This gene product was detected in the proteome analysis reported in Example I, but only detected in the amastigote stage.

In creating genetically engineered live vaccine strain, it is first determined whether *T. cruzi* cells can survive (as epimastigotes and metacyclic trypomastigotes—or "insect" stages) despite the knockout. If so, it is then determined whether they are avirulent; i.e., whether they die upon entering the host cell and converting to the amastigote forms, due to this metabolic deficiency. A multiple knockout strain of *T. cruzi* is preferred as a live vaccine. This better ensures that there is no possibility for reversion to a virulent form.

A genetically engineered *T. cruzi* is thus provided in which the production of any protein identified herein, preferably a fatty acid metabolism protein, a transporter protein, or a histidine pathway protein, is reduced or eliminated.

It should be noted that as an alternative to administering a live *T. cruzi* vaccine containing a knockout in the metabolic pathway for metabolism of fatty acids, the host cells can instead be starved of fatty acids.

Pharmaceutical Compositions

Pharmaceutical compositions containing *T. cruzi* antibodies, immunogenic polypeptides, polynucleotides encoding immunogenic polypeptides, and/or live, genetically engineered *T. cruzi*, as described herein, together with a pharmaceutical carrier, are also provided.

The compounds, compositions and genetically engineered organisms described herein are readily formulated as pharmaceutical compositions for veterinary or human use. The pharmaceutical composition optionally includes excipients or diluents that are pharmaceutically acceptable as carriers and compatible with the genetic material. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, salts, and/or adjuvants which enhance the effectiveness of the immune-stimulating composition. Methods of making and using such pharmaceutical compositions are also included in the invention.

Immunization Methods

The invention further encompasses methods for prophylactic and therapeutic immunization of mammals against *T. cruzi* infection and disease. Medical uses in humans to prevent or treat infection, and veterinary uses in other animals to prevent or treat infection or to control transmission of infection are examples of contemplated applications.

Administration of the Polynucleotide Vaccine

The polynucleotide vaccine of the invention can be administered to the mammal using any convenient method, such as intramuscular injection, topical or transdermal application to the mammal's skin, or use of a gene gun, wherein particles coated with the polynucleotide vaccine are shot into the mammal's skin. The amount of polynucleotide administered to the mammal is affected by the nature, size and disease state of the mammal as well as the delivery method; for example, typically less DNA is required for gene gun administration than for intramuscular injection. Further, if a polynucleotide encoding a cytokine is co-delivered with nucleotide coding regions encoding the immunogenic polypeptide from *T. cruzi*, the amount of polynucleotide encoding the immunogenic polypeptide from *T. cruzi* in the vaccine is optionally reduced.

Hundreds of publications have now reported the efficacy of DNA vaccines in small and large animal models of infectious diseases, cancer and autoimmune diseases (J. Donnelly et al., Rev. Immunol. 15:617 (1997). Vaccine dosages for humans can be readily extended from the murine models by one skilled in the art of genetic immunization, and a substantial literature on genetic immunization of humans is now available to the skilled practitioner. For example, Wang et al. (Science 282:476-480 (1998)) vaccinated humans with plasmid DNA encoding a malaria protein, and the same group has developed a plan for manufacturing and testing the efficacy of a multigene *Plasmodium falciparum* liver-stage DNA vaccine in humans (Hoffman et al., Immunol. Cell Biol. 75:376 (1997)). In general, the polynucleotide vaccine of the invention is administered in dosages that contain the smallest amount of polynucleotide necessary for effective immunization. It is typically administered to human subjects in dosages containing about 20 µg to about 2500 µg plasmid DNA; in some instances 500 µg or more of plasmid DNA may be indicated. Typically the vaccine is administered in two or more injections at time intervals, for example at four week intervals.

Administration of the Polypeptide Vaccine

Like the polynucleotide vaccine, the polypeptide vaccine can be administered to the mammal using any convenient method, such as intramuscular or intraperitoneal injection, topical administration, oral or intranasal administration, inhalation, perfusion and the like. The amount of polypeptide administered to the mammal is affected by the nature, size and disease state of the mammal, as well as by the delivery method. Intraperitoneal injection of 25 to 50 ug of polypeptide containing a membrane transducing sequence has been shown to result in import of the protein into nearly 100% of murine blood and spleen cells within 20 minutes (Schwarze et al., Science 285:1569-1572 (1999)) and the sensitization of cytotoxic T cells (M.-P. Schutze-Redelmeier et al., J. Immunol. 157:650-655 (1996)). Useful dosages of the polypeptide vaccine for humans can be readily determined by evaluating its activity in vivo activity in mice. It should be understood that both a polynucleotide vaccine and a polypeptide vaccine can be administered to a mammal in a serial protocol. For example, a plasmid-based DNA vaccine may be administered to a mammal to "prime" the immune system, followed by the one or more administrations of a polypeptide vaccine or a viral vaccine (e.g., vaccinia vector carrying the genes that encode the immunogenic polypeptides and, optionally, cytokines) to further stimulate the mammal's immune system. The order of administration of the different types of vaccines, and the nature of the vaccines administered in any given dose (e.g., polypeptide vaccine, plasmid vaccine, viral vector vaccine) can be readily determined by one of skill in the art to invoke the most effective immune response in the mammal.

Administration of the Live Vaccine

The live vaccine can be administered by contacting the subject with a genetically engineered *T. cruzi* so as to elicit a protective immune response in the animal to *T. cruzi*. The live vaccine is preferably administered by injection, particularly when the subject is a mammal. Alternatively, a subject can be exposed to an ingestible composition, such as food, water, or both, that contains an genetically engineered *T. cruzi*.

Types of Vaccine-Induced Immunity to *T. cruzi*

Vaccine-induced immunity to *T. cruzi* according to the present invention can take a variety of forms. In one embodiment, the vaccine induces sterilizing immunity against *T. cruzi* in the mammalian host. "Sterilizing immunity" means that a vaccinated, pathogen-free mammal will, when exposed to the pathogen, not develop a persistent infection but instead will totally clear the pathogen (prophylactic vaccination); and also that a pathogen-infected mammal will clear the pathogen and be free of the infection and disease following administration of the vaccine (therapeutic vaccination). However, because a high percentage—well over 50%—of people infected with *T. cruzi* fail to develop chronic disease symptoms even though they appear to remain infected for their entire lives, it is expected that a balance can be reached in an infected host between an effective immune response and parasite persistence without the development of clinical disease. Thus, in another embodiment, the vaccine elicits a set of responses that are sufficient to delay or, preferably, prevent disease development in *T. cruzi* infected individuals despite the persistence of parasites. Like a vaccine that induces "sterilizing immunity," this vaccine can be administered prophylactically, in advance of infection, or therapeutically, after infection but before the development of a chronic debilitating disease state. This embodiment of the vaccine is suitable for delivery to individuals who are infected and at risk of developing disease.

In one embodiment, the live vaccine administered to dogs in accordance with the invention is effective to generate sterilizing immunity or near-sterilizing immunity. In this method the goal of administering the vaccine is to decrease parasite load, thereby preventing infection of feeding insects. Preferably, the number of circulating parasites in the dog after vaccination is very low, more preferably zero.

In another embodiment, the administration of the vaccine to a dog, human or other animal has, as its goal, the treatment or prevention of *T. cruzi* infection. The vaccine can be administered therapeutically to a mammal harboring a persistent protozoan infection. In one embodiment, administration of the vaccine is effective to eliminate the parasite from the mammal; in another embodiment, administration of the vaccine is effective to prevent or delay chronic debilitating disease in the mammal. Alternatively, a vaccine of the invention can be administered prophylactically to a mammal in advance of infection by the protozoan. In one embodiment, the vaccine is effective to prevent subsequent infection of the mammal by the protozoan. In another embodiment, administration of the vaccine is effective to prevent the development of chronic debilitating disease the mammal after subsequent infection by the protozoan. In yet another embodiment, administration of the vaccine effective to prevent the death of the mammal after subsequent infection by the protozoan.

Prophylactic and Therapeutic Immunization

The present invention contemplates both prophylactic and therapeutic immunization against *T. cruzi* infection and the chronic disease state, known as Chagas' disease, that often eventually follows initial *T. cruzi* infection. Therapeutic administration of the polynucleotide or polypeptide vaccine to infected subjects is effective to delay or prevent the progression of the *T. cruzi* infection to a chronic disease state, and also to arrest or cure the chronic disease state that follows *T. cruzi* infection. Prophylactic administration of the polynucleotide or polypeptide vaccine to uninfected subjects is effective to reduce either or both if the morbidity and mortality associated with infection by *T. cruzi*. Further, if an uninfected, vaccinated subject is subsequently infected with *T. cruzi*, the vaccine is effective to prevent progression of the initial infection to a chronic disease state. See 235.00200201 (US Pat.) for a more detailed discussion of types of immune responses and therapeutic and prophylactic administration of a vaccine.

Drug Development and Screening Assays

*T. cruzi* proteins identified herein, particularly those that are stage-regulated, represent attractive candidates for drug development. One class of preferred targets includes proteins involved in stage-specific pathways for energy metabolism. Other preferred targets include membrane-bound transporter proteins, particularly transporter proteins that are unique to *T. cruzi*. In a preferred embodiment, a therapeutic agent targets a protein that is expressed by a *T. cruzi* amastigote. Because amastigotes are intracellular parasites, the therapeutic agent is introduced into the host cell through the host cell membrane, where in can come into contact with the intracellular parasite. In one embodiment, the therapeutic agent is internalized by the host cell using receptor-mediated endocytosis. A preferred therapeutic agent is a compound that includes a ligand that binds to a host cell receptor, thereby facilitating entry into the host cell. In a particularly preferred embodiment, the compound includes a ligand that is selective for receptors present on host muscle cells and adipocytes, as well as the therapeutic agent. Another preferred therapeutic agent is a compound that includes a membrane translocating sequence as described above in connection with the polypeptide vaccine, to facilitate introduction of the polypeptide into the mammalian cell. Alternatively, the therapeutic agent, for example a peptide, may cross the host cell membrane by diffusing through it.

Membrane-bound *T. cruzi* transporter proteins and co-transporter proteins (i.e., those which assist with uptake of metabolites through a transporter protein) may be, for example, integral membrane proteins or GPI-linked proteins. They represent preferred targets for the therapeutic agent, since the therapeutic agent need not be internalized by *T. cruzi* in order to be effective. A therapeutic agent that blocks uptake of a metabolite by an intracellular *T. cruzi* amastigote will have a deleterious effect on the metabolism of the *T. cruzi*. A preferred compound binds to the transporter protein to inhibit or prevent transport of a metabolite from the host cytoplasm into *T. cruzi*. Preferred targets include fatty acid transporter proteins and glucose-6-phosphate transporter proteins.

The invention provides a screening method to identify therapeutic agents. In one embodiment, the target protein is cloned and expressed, and the candidate agent is screened for binding to the target protein using methods well-known to the art. In another embodiment wherein the target protein is an enzyme, the therapeutic agent is screened for inhibition of enzymatic activity. Therapeutic agents (drugs) include antibodies, peptides, peptidomimetics, small organic molecules, RNAs, DNAs (e.g., antisense oligonucleotides) and the like.

EXAMPLES

The present invention is illustrated by the following examples. It is to be understood that the particular examples, materials, amounts, and procedures are to be interpreted broadly in accordance with the scope and spirit of the invention as set forth herein.

Example I

The *Trypanosoma cruzi* Proteome

Proteomic analysis of *T. cruzi*, the causative agent of Chagas disease, has identified distinct energy sources for the individual parasite stage. A whole-organism, proteomic analysis of the four life-cycle stages of *T. cruzi* was used. Peptides mapping to 2784 proteins in 1168 protein groups from the annotated *T. cruzi* genome were identified across the four life-cycle stages. Protein products were identified from >1000 genes annotated as "hypothetical" in the sequenced genome, including members of a newly defined gene family annotated as mucin-associated surface proteins (MASPs). The four parasite stages appear to use distinct energy sources, including histidine for stages present in the insect vectors and fatty acids by intracellular amastigotes.

Like other trypanosomatids, *T. cruzi* appears to regulate protein expression primarily post-transcriptionally through variations in mRNA stability or the translational efficiency of mRNAs (Clayton, *Embo J* 21, 1881 (Apr. 15, 2002)). This limits the use of DNA microarrays (Akopyants et al., *Mol Biochem Parasitol* 113, 337 (2001); Minning et al., *Mol Biochem Parasitol* 131, 55 (September 2003); Diehl et al., *Mol Biochem Parasitol* 123, 115 (Aug. 28, 2002), Duncan, *Trends Parasitol* 20, 211 (May 2004)), and makes proteomic analysis especially attractive for examining global changes in protein expression during development in *T. cruzi*.

See Atwood et al. (2005) *Science,* 309, 473-476 and El-Sayed et al. (2005) *Science,* 309, 409-415. Supporting material for both articles is available online at www.sciencemag.org.

Materials and Methods

Parasites. Brazil strain *T. cruzi* trypomastigotes were grown in monolayers of Vero cells (ATCC no. CCL-8 1) in RPMI supplemented with 5% horse serum as previously described (Piras et al., *Mol Biochem Parasitol* 6, 67 (August 1982)). Emergent trypomastigotes were harvested daily and examined by light microscopy to determine the percentages of amastigotes and trypomastigotes. Only preparations containing >95% trypomastigotes were used in the subsequent studies. Amastigotes (>95% pure) were prepared axenically from low pH-induced trypomastigotes as described previously (Tomlinson et al., *Parasitology* 110 (Pt 5), 547 (June 1995)). Amastigotes generated by this method are well-documented to be indistinguishable from intracellular amastigotes and have been widely used to study amastigote biology. However, it is possible that changes noted in the proteome of these artificially derived amastigotes might differ from that of amastigotes obtained from infected host cells. Epimastigotes were grown in Liver Infusion Tryptose media (LIT) as previously described (Rondinelli et al., *Exp Parasitol* 66, 197 (August 1988)). Cultures were harvested during mid-log phase by centrifugation at 3,000×g for 10 m at room temperature. Metacyclic trypomastigotes were obtained from epimastigotes by axenic induction as previously described (Chao et al., *Zhonghua Min Guo Wei Sheng Wu Ji Mian Yi Xue Za Zhi* 17, 146 (August 1984)). The percentages of metacyclics were determined by microscopic examination of parasites stained with Dif-Quick (Baxter Diagnostics, McGaw Park, Ill.). Metacyclic trypomastigotes were purified from the resulting cultures by DEAE-Sephacel chromatography as described previously (Isola et al., *J Parasitol* 72, 467 (June 1986)).

Whole and sub-cellular protein isolation. Proteins were isolated from 1-3×10$^9$ organisms/preparation using Tri-Reagent (Sigma). Whole-cell lysates from three epimastigote, two metacyclic trypomastigote, two amastigote, and two trypomastigote biological replicate preparations were generated and analyzed separately. In some cases, crude cytoplasmic and membrane preparations were obtained from amastigotes and trypomastigote by lysis in ice-cold lysis buffer (150 mM NaCl, 1.5 mM $MgCl_2$, 0.5% (v/v) NP-40, and 10 mM Tris-HCl, pH 8.0). Nuclei were removed by centrifugation at 2,000×g at 4° C. for 2 min., and membrane fractions were harvested from the post-nuclear supernatants by centrifugation at 12,000×g at 4° C. for 5 min. Cytoplasmic fractions were obtained from the resulting post-membrane supernatant, and proteins were then isolated from each lysate with Tri-Reagent. Isolated proteins from each of the lysates were independently reduced, carboxyamidomethylated, digested with endoproteinase Lys-C, and digested with trypsin as previously described (Weatherly et al., *Mol Cell Proteomics* 4, 762 (June 2005)).

Peptide separation and MS/MS analysis. Peptide mixtures generated from the whole-cell lysates of *T. cruzi* epimastigotes, metacyclic trypomastigotes, amastigotes, and trypomastigotes were independently separated and analyzed as previously described (Weatherly et al., *Mol Cell Proteomics* 4, 762 (June 2005)). The strong cation exchange separation step was omitted in the preparation of the four sub-cellular lysates.

Protein sequence databases. Four sequence databases were constructed for these analyses. A representative database (normal) consisting of 23,095 *Trypanosoma cruzi* gene annotations provided by *Trypanosoma cruzi* Sequencing Consortium (TSK-TSC; version 3) was employed for the final protein identifications. A randomized database (random), which was created by inverting the sequences in the normal database, was used to establish accurate scoring thresholds for protein identification in the normal database. For removal of contaminant peptides, two databases were used: a composite database was created by combining the TSK-TSC database with 10,468 protein sequences from *Bos Taurus, Equus caballus, Homo sapien*, and proteases from the National Center for Biotechnology Information (NCBI) and a second database containing the TSK-TSC proteins plus 298,912 primate protein sequences from NCBI. The former database was used to remove contaminant spectra matching peptides that may have been introduced during sample preparation and the latter to identify potential contaminants arising from the cultivation of *T. cruzi* in Vero green monkey kidney cells. Lastly, for the ORF analysis, a database of 817,000 open reading frames (ORFs) of at least 50 amino acids was constructed from a number of sequence sources. These include 48 large, partially assembled contigs from *T. cruzi* obtained from NCBI, consensus sequences constructed from raw sequence reads obtained from the TSK-TSC prior to the assembly of the *T. cruzi* genome, and the contigs used for the gene predictions made by the TSK-TSC. Unique peptides identified by spectra that failed to match proteins predicted by the annotated genome were clustered to these 817,000 ORFs, and the new proteins were annotated and the spectra matching each were manually verified. ORFan proteins identified by this method were annotated using BLAST homologies (GenBank NR and the *T. brucei, L. major*, and *T. cruzi* annotated genomes), protein domains (InterPro; Mulder et al., *Nucleic Acids Res* 31, 315 (Jan 1, 2003)), signal peptide motifs (SignalP; Nielsen et al., *Int J Neural Syst* 8, 581 (October-December 1997)), and GPI anchor addition motifs (DGPI, Kronegg, 1999. http://129.194.185.165/dgpi/).

Data processing and analysis. Peak-lists were first filtered to remove spectra originating from singly charged ions with parent ion masses <600 Da, and the remaining spectra were then submitted for database searching with Mascot (Matrix Science, Boston, Mass.). Mascot searches were limited to fully tryptic peptides to restrict the number of candidate peptides from the database which could match to each spectrum. Parent and fragment mass errors from identified peptides with Mascot scores exceeding 60 were used to perform linear recalibration of all spectra as previously described (Strittmatter et al., *Anal Chem* 75, 460 (Feb. 1, 2003)). Following recalibration, peak-lists were distributed into 4 bins as a function of maximum parent mass error (50, 100, 150, 200 p.p.m.). Spectra within each bin were searched with Mascot using the following parameters: enzymatic cleavage with trypsin, 1 potential missed cleavage, peptide tolerances of 50, 100, 150 and 200 ppm, fragment ion tolerance of 0.2 Da, and variable modifications due to carbamylation (+43 Da) and carboxyamidomethylation (+57 Da). Spectra matching contaminant peptides were removed from the peak-lists and the database search was repeated against the normal and random databases.

Protein identification and validation. PROVALT (Weatherly et al., *Mol Cell Proteomics* 4, 762 (June 2005)), uses the confidence in individual peptide matches along with the number of peptides that match to proteins to identify high-confidence proteins in a high-throughput manner. To this end, PROVALT extracts peptide matches and corresponding ion scores from the normal and random Mascot results files and filters them to create a non-redundant list of peptides. The peptides in each list are then binned according to score, where each bin contains all peptides at or above the Mascot ion score that it represents. The peptides in the normal and random bins are then clustered to the proteins in their corresponding sequence databases. In cases where a peptide or a set of peptides map to more than one protein, and thus cannot be uniquely assigned to an individual protein, PROVALT groups proteins into "protein groups". In order to select protein groups with a false-discovery rate of <1%, PROVALT iteratively determines the score bin in the random database for which the number of identified protein groups meeting the specified minimum peptide coverage is <1% of that of the corresponding bin in the normal database. The peptide coverage value is decreased for each iteration. For this work, the peptide coverage levels and minimum score thresholds were as follows: 6 (or more) peptides with score>14, 5 peptides with score>17, 4 peptides with score>22, 3 peptides with score >28, 2 peptides with score>35, and 1 peptide with score>43.

Results and Discussion

Figure 3:
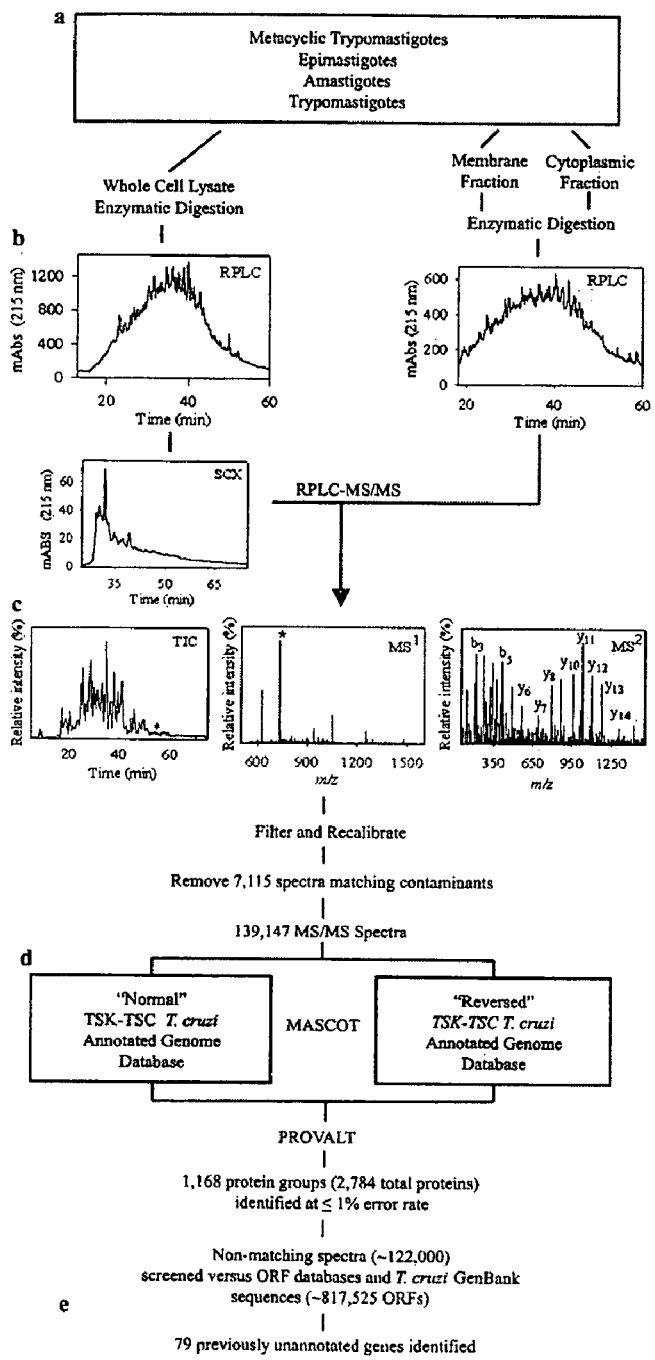

Metacyclic trypomastigotes, amastigotes, trypomastigotes and epimastigotes of *T. cruzi* were isolated, and proteins were extracted from whole-cell or sub-cellular lysates (FIG. 3). Peptides generated by digestion of the whole-cell or sub-cellular lysates were independently separated and analyzed at least in duplicate by offline multidimensional liquid chromatography, online reverse phase liquid chromatography and tandem mass spectrometry (LC-MS/MS; 7 Weatherly et al., *Mol Cell Proteomics* 4, 762 (June 2005). A total of 602 tryptic peptide samples were analyzed, generating 139,147 tandem mass spectra. Because of differences in protein recovery from the four life-cycle stages, trypomastigote and amastigote stages are under-sampled relative to metacyclic trypomastigotes and epimastigotes (Table 3, FIG. 5).

A total of 5,720 unique peptides were matched with high confidence to 1168 protein groups containing 2784 total proteins using the Mascot search engine and PROVALT parsing and clustering tools (Weatherly et al., *Mol Cell Proteomics* 4, 762 (June 2005)), as described in the supporting online material (Table 4, FIG. 6). The approach of grouping protein isoforms (Nesvizhskii et al., *Anal Chem* 75, 4646 (Sep. 1, 2003); Resing et al., *Anal Chem* 76, 3556 (Jul. 1, 2004)) is particularly important in *T. cruzi* because the genome contains multiple, non-identical copies of many genes, including a number of large gene families with hundreds of distinct members (El-Sayed et al. (2005) *Science,* 309, 409-415). In addition, the *T. cruzi* C L Brener strain used for the sequencing project is a hybrid of two genotypes and thus has multiple distinct alleles for most genes.

Table 1 summarizes the proteins assigned to each life-cycle stage. Nearly 30% (838 of 2784) of the identified proteins, including most of the proteins previously documented or expected to be produced in the greatest abundance, were detected in all life-cycle stages. The table shows "protein groups" as assigned by PROVALT. For example, in the first line, there are 29 protein groups which together include 49 total proteins that are detected only in the amastigote stage. The supplemental tables can be used to identify the particular proteins that are detected only in a particular stage, for example, by ranking the proteins by MASCOT score.

TABLE 1

Protein group and protein identifications for each developmental stage

| PROVALT Protein groups (proteins) | Amastigote | Trypo-mastigote | Metacyclic trypomastigote | Epimastigote |
|---|---|---|---|---|
| 29 (49) | X | | | |
| 21 (41) | X | X | | |
| 44 (161) | X | X | X | |
| 335 (838) | X | X | X | X |
| 27 (84) | X | X | | X |
| 65 (110) | X | | X | |
| 146 (538) | X | | X | X |
| 24 (50) | X | | | X |
| 43 (125) | | X | | |
| 47 (122) | | X | X | |
| 53 (93) | | X | X | X |
| 12 (22) | | X | | X |
| 187 (315) | | X | X | |
| 92 (162) | | | X | X |
| 43 (74) | | | | X |
| 1168 (2784) | 691 (1871) | 582 (1486) | 969 (2339) | 732 (1861) |

Shotgun proteome LC-MS/MS analysis as conducted herein does not detect changes in protein expression levels with the same precision as is possible using stable isotope labelling techniques. Nevertheless, it provides empirical evidence of protein expression and allows for high-throughput comparison of protein detection among the four life-cycle stages of *T. cruzi*, something that cannot be accomplished with current quantitative technologies. As others have done (Florens et al., *Nature* 419, 520 (Oct. 3, 2002)), we employed measures of peptide coverage, including total protein score, to indicate the relative abundance of proteins in the *T. cruzi* proteomes and to track relative changes in protein expression in the individual life-cycle stages. This approach provides provisional evidence for the relative abundance and the presence or absence of a particular protein in any given stage. For the relatively small subset of proteins in *T. cruzi* with known expression patterns (Paba et al., *Proteomics* 4, 1052 (April 2004); Paba et al., *J Proteome Res* 3, 517 (May-June 2004); Parodi-Talice et al., *Int J Parasitol* 34, 881 (July 2004)), our results agree in virtually all cases. The well-characterized trans-sialidase (ts) and mucin families highlight two limitations of shotgun proteomics: the lack of resolution due to shared peptides and the under-representation of highly glycosylated proteins. Peptides matching to 223 members of the ts family clustered into 50 protein groups were detected in one or more stages. In contrast, no peptides mapping to mucin family proteins were identified, presumably due to the high level of mucin glycosylation (DiNoia et al., *J Biol Chem* 270, 24146 (1995)). Also, because of differences in protein recovery from the different life-cycle stages, trypomastigote and amastigote stages are under-sampled relative to metacyclic trypomastigotes and epimastigotes. Therefore conclusions on the stage restricted expression of proteins in over-sampled stages, and likewise their absence in under-sampled stages, should be considered provisional. The 2784 proteins and 1168 protein groups represent the upper and lower limits, respectively, for the number of proteins confirmed to be expressed based upon this analysis. Slightly less than 25% (290) of the protein groups were identified by a single peptide match using a minimum Mascot score of 43 (corresponding to a peptide false-discovery rate of 0.09% based on comparison to the random database).

Among the top scoring proteins in all four *T. cruzi* proteomes are many housekeeping proteins that are also among the highest ranking proteins in yeast (Ghaemmaghami et al., *Nature* 425, 737 (Oct. 16, 2003)). However, many other highly abundant proteins in the *T. cruzi* proteome are either absent in the yeast genome or are expressed at very different relative levels in these two eukaryotes (e.g. paraflagellar rod protein 3, 8152.t00002; flagellar calcium-binding protein, 5387.t00002; I/6 autoantigen, putative, 7685.t00010; and 14-3-3 protein-like, 8730.t00013) or are expressed at very different relative levels in these two eukaryotes (e.g. d-isomer specific 2-hydroxyacid dehydrogenase-protein, 8304.t00012; malic enzyme, 7814.t00028; and alpha tubulin, 11788.t00001). Note that the identifying numbers used herein are gene ID numbers from the *T. cruzi* database; available on the worldwide web at tcruzidb.org.

Figure 4:
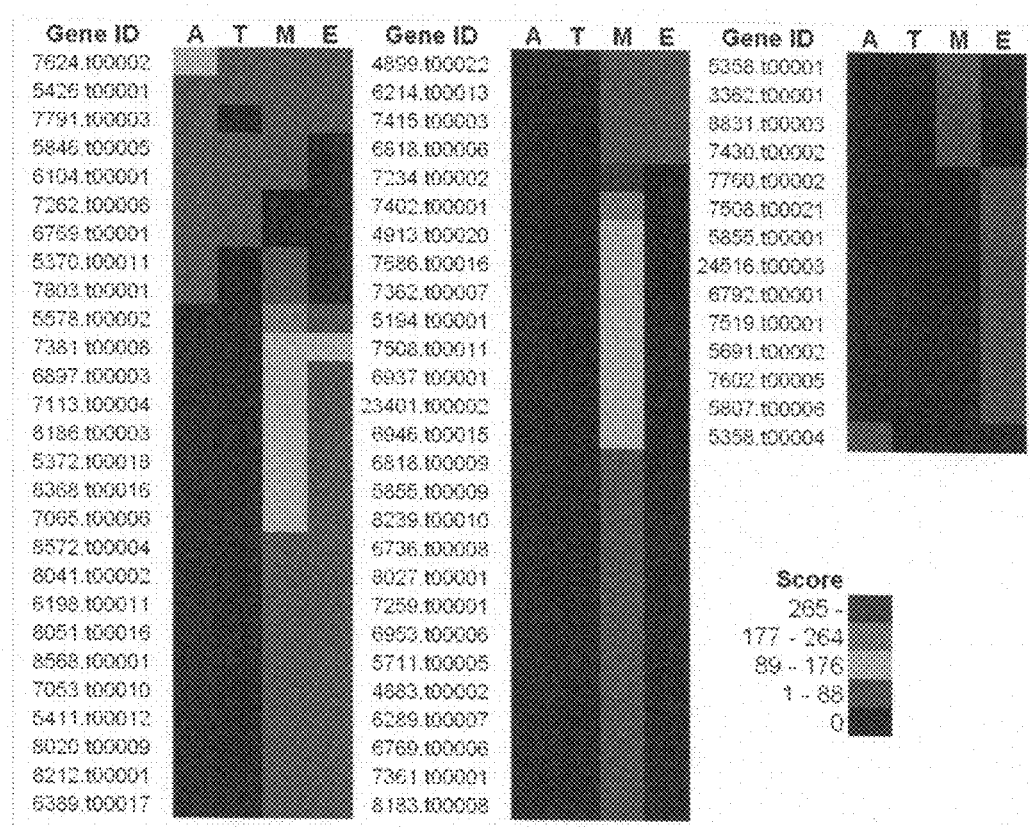

Additional gene family members detected in the *T. cruzi* proteomes include those from the cysteine protease (detected in all life-cycle stages except trypomastigotes) and gp63 (detected in all stages except the amastigotes) families. Genes encoding the retrotransposon hot spot (RHS) proteins are plentiful in the *T. cruzi* and *T. brucei* genomes and were first identified in the latter as potential sites for insertions of retrotransposons. Although the function of the proteins encoded by RHS genes is not known, they were found to be constitutively expressed in *T. brucei* and to localize primarily to the nucleus (Bringaud et al., *Eukaryot Cell* 1, 137 (February 2002)). Here we show that the RHS proteins are expressed in *T. cruzi* from multiple loci and in all developmental stages (FIG. 4). The RHS proteins are detected most prominently in the metacyclic forms, but this could be due to the greater overall sampling of this stage in our analysis. A sample of other apparently stage-regulated proteins expressed in the trypomastigote proteome is shown in Table 5 (FIG. 7).

Table 2 summarizes some of the major protein groups and families identified in the *T. cruzi* proteome. These data reflect a combination of the relative abundance of the proteins comprising each group, the size of gene families and the ease with which certain proteins can be detected by LC-MS/MS analysis. Of the 2784 total proteins identified in this analysis, 1008 are from genes annotated as "hypothetical", validating these as bonafide genes in *T. cruzi*. Over half of these hypothetical genes have orthologs in the *Leishmania major* and/or *Trypanosoma brucei* genomes.

TABLE 2

Major protein families and functional classes

| Protein functional classes | Number of identified proteins |
|---|---|
| Ribosomal | 212 |
| Proteasome/Ubiquitin | 67 |
| Heat shock/Chaperonins | 61 |
| Translation/Transcription | 49 |
| Histones | 36 |
| *Gene families* | |
| Trans-sialidase | 223 |
| RHS | 399 |
| GP63 | 29 |
| Cysteine protease | 30 |
| MASP | 9 |
| Mucins | 0 |
| *Hypothetical genes* | |
| Hypothetical | 155 |
| Hypothetical conserved | 505 |
| Hypothetical to be annotated | 348 |

Figure 2:
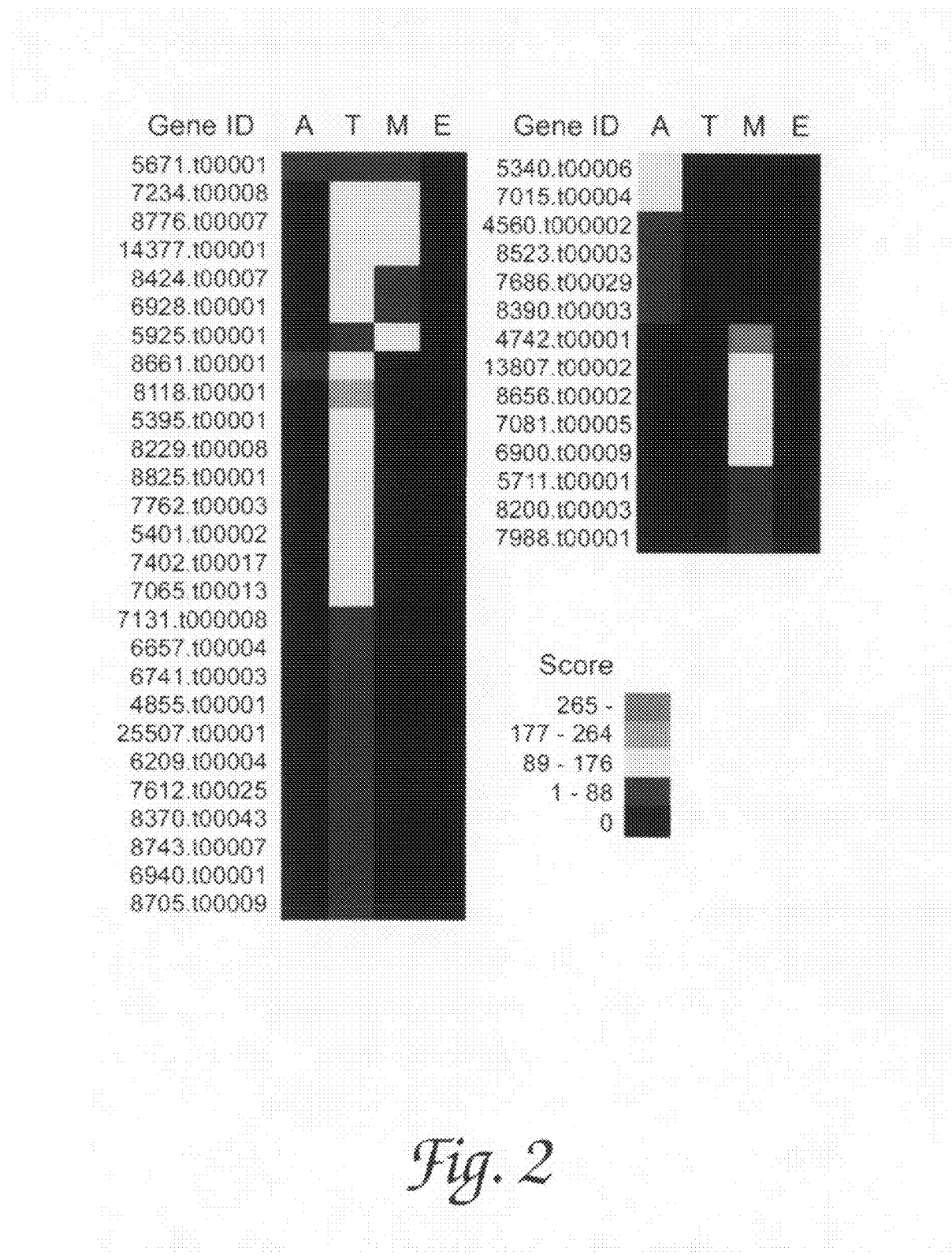

*T. cruzi* trypomastigotes circulate in the blood where they are exposed to host immune effector molecules, including specific antibodies. Unlike the related African trypanosomes, *T. cruzi* trypomastigotes do not undergo antigenic variation but instead express on their surface multiple members of several large families of molecules; the best characterized of these are the mucins and trans-sialidases (ts) (Frasch, *Parasitol Today* 16, 282 (July 2000)). Thirty of the 50 top-scoring proteins detected exclusively in trypomastigotes are ts family members. Likewise, the amastigote and metacyclic stages appear to express subsets of ts molecules unique to each stage while no ts expression was detected in the epimastigote proteome (FIG. 2 and Table 4, FIG. 6). Trans-sialidase enzymatic activity is reportedly present in only a small subset of the >1000 ts proteins encoded in the *T. cruzi* genome and has been linked to the presence of Tyr342 in the catalytic N-terminal region and SAPA repeats in the c-terminus (Frasch, *Parasitol Today* 16, 282 (July 2000)). Among the 223 ts proteins detected in the proteome are the products of all 15 genes predicted to encode enzyme active ts. The production of a large number of non-enzymatic ts family members coincident with these ts enzymes may deflect immune responses away from the enzymatically active targets or may provide a pool of altered peptides that could antagonize T cell responses (Martin et al., *Immunol Rev* 201, 304 (October 2004)).

In addition to the ts and mucin families, the *T. cruzi* genome contains several other high copy, multi-gene families (Table 2). We detected expression of several mucin-associated surface proteins (MASP), a gene family first discovered as part of the sequencing and annotation effort (El-Sayed et al., (2005) *Science*, 309, 409-415) predominantly in the trypomastigote proteome. Like proteins from the other multi-gene families in *T. cruzi*, many MASP family members have predicted signal sequences and GPI anchor addition sites and thus are likely to be surface-expressed. Nine MASP gene family proteins were identified in our analysis, each by only a single peptide match. This result suggests that either MASPs are not as abundantly expressed as the trans-sialidase proteins, or that, like the mucins, MASPs have extensive post-translational modifications which complicate their detection by shotgun proteomics. However, detection of the MASPs in the relatively under-sampled trypomastigote stage suggests that they are not minor constituents of the *T. cruzi* proteome.

The transition from trypomastigote to amastigote can be stimulated extracellularly by simulating the low pH environment of the phagosomal/lysosomal compartment that *T. cruzi* initially encounters upon cell entry (Tomlinson et al., *Parasitology* 110 (Pt 5), 547 (June 1995)), making early time points in the transformation process to the amastigote stage amenable to transcriptome and proteome analysis. The results from this proteome analysis of amastigotes are in agreement (with one exception) with the restricted data set generated by comparison of trypomastigotes and early stage amastigotes using DNA microarray analysis (Minning et al., *Mol Biochem Parasitol* 131, 55 (September 2003)). (Table 6, FIG. 8), further supporting the quality of this analysis. In addition to the expression of a distinct subset of trans-sialidase-family genes, many of which are related to the amastigote surface protein 2 molecule previously reported to be preferentially expressed in amastigotes (Low et al., *Mol. Biochem. Parasitol.* 160, 1817 (1997) (FIG. 2), the transition of trypomastigotes to amastigotes also appears to be accompanied by a dramatic shift from carbohydrate to lipid dependent energy metabolism (Table 5, FIG. 7). This is demonstrated by the virtual absence of glucose transporters and the detection of enzymes that oxidize fatty acids to give acetylcoenzyme A. Enzymes of the citric acid cycle, which oxidize acetyl coenzyme A to carbon dioxide and water are also abundant in amastigotes. Amastigotes are likely to be dependent on gluconeogenesis for the synthesis of glycoproteins and glycoinositolphospholipids (GIPLs) and aspartate aminotransferases (4698.t00001, 4779.t00007; recall that gene identification numbers used herein are from the *T. cruzi* database, and are available on the worldwide web at tcruzidb.org) specific to amastigotes may be important in this process. These proteins lack the mitochondrial targeting signal present on the aspartate aminotransferase expressed in all stages (6015.t00007) and thus likely reside in the cytoplasm. Mitochondrially produced oxaloacetate, after transamination, may be transported to the cytosol by a malate/aspartate shuttle and then converted by the cytosolic aspartate aminotransferase and a phosphoenol pyruvate carboxykinase into phosphoenol pyruvate, the substrate for gluconeogenesis.

In addition to several heat shock proteins and kinases, among the other proteins detected preferentially or exclusively in amastigotes are a group involved in endoplasmic reticulum (ER) to Golgi trafficking, including rab1 (4703.t00005), sec23 (8726.t00010), and sec31 (6890.t00029). The detection of this set of proteins involved in vesicular trafficking in amastigotes but not in the more highly sampled metacyclic and epimastigote stages suggests a more active trafficking process or the preferential use of selected rab and sec proteins in amastigotes (Table 5, FIG. 7). We also extend the data on the selective expression in amastigotes and epimastigotes of several ABC transporters (7164.t00003, 8319.t00008) that are hypothesized to have a role in cargo selection and/or vesicular transport in trypanosomes (Torres et al., *Mol Microbiol* 54, 632 (December 2004)). A putative lectin (6865.t00003) with homology to ERGIC, a protein involved in cargo selection in COPII vesicles, is also detected in trypomastigotes and amastigotes but not in metacyclic or epimastigote forms.

In contrast to both *T. brucei* and *L. major*, the *T. cruzi* genome encodes enzymes capable of catalyzing the conversion of histidine to glutamate. The first two enzymes in this pathway, histidine ammonia-lyase (6869.t00022) and urocanate hydratase (4881.t00011), are abundant in the insect stages but nearly undetectable in the mammalian stages (only a single spectrum matching histidine ammonia-lyase in amastigotes), consistent with the function of this pathway primarily in epimastigotes and metacyclic trypomastigotes. This expression pattern is interesting, given that histidine is the dominant free amino acid in both the excreta and hemolymph of Rhodnius prolixus (Harington, *Parasitology* 51, 309 (December 1961); Harington, *Nature* 178, 268 (Sep. 4, 1956)) a well-studied vector for *T. cruzi*. The abundance of histidine in this and other blood-feeding insects likely reflects the high histidine content of hemoglobin (Vickery, *J. Biol. Chem.* 144, 719 (1942)). Thus, *T. cruzi* epimastigotes seem uniquely adapted among the kinetoplastids to take advantage of this plentiful energy source in the gut of its insect vector. This is analogous to the use of proline as an energy source by T. brucei (Evans et al., *J Protozool* 19, 686 (November 1972)).

The transformation of epimastigotes to metacyclic trypomastigotes is accompanied by the production of a number of key enzymes and substrates important in antioxidant defense in *T. cruzi*. The $H_2O_2$ and peroxynitrite detoxifying enzymes ascorbate peroxidase (6846.t00006, 4731.t00003) (Wilkinson et al., *Proc Natl Acad Sci USA* 99, 13453 (Oct. 15, 2002)) and the mitochondria-localized tryparedoxin peroxidase (8115.t00003) are both elevated following epimastigote to metacyclic conversion, as are tryparedoxin (5824.t00003), the substrate for tryparedoxin peroxidase, and the enzymes trypanothione synthase (8070.t00009, 7998.t00005) and iron superoxide dismutase (5781.t00004), responsible for synthesis of trypanothione and for the conversion of superoxide anion to hydrogen peroxides, respectively. These changes are consistent with a pre-adaptation of metacyclic forms to withstand the potential respiratory burst of phagocytic cells in the mammalian host. Enzymes of the pentose-phosphate shunt aid this process through the production of the NADPH required for the reduction of trypanothione. Also noticeable in the transition of epimastigotes into metacyclic trypomastigotes is a substantial decrease in the representation of ribosomal proteins in the metacyclic proteome; 37 of the 50 highest scoring proteins in the epimastigote proteome that are not detected in the metacyclic trypomastigote proteome are ribosomal proteins. A reduction in the capacity for protein production would be consistent with the stationary, non-replicating status of metacyclic trypomastigotes. DNA microarray analysis has also documented a substantial down-regulation of ribosomal protein expression in metacyclic forms in *L. major* (Almeida et al., *Mol Biochem Parasitol* 136, 87 (July 2004)).

A search for peptides with modifications (e.g. acetylations, methylations or phosphorylations) resulted in 8 additional protein identifications and the detection of modifications on 81 previously identified proteins (Table 7, FIG. 9). To identify additional genes potentially missed in the annotations provided by the *T. cruzi* sequencing consortium, a database of approximately 817,000 open reading frames (ORFs) of >50 amino acids was constructed and screened using spectra that failed to match proteins predicted by the annotated genome. This analysis yielded 79 new genes, new alleles or modifications to existing gene annotations (Table 8, FIG. 10). Sixty-six of these ORFans are new alleles of annotated genes or corrections to existing annotations, suggesting that the prediction models and annotations by the TSK-TSC have been extremely efficient in accurately predicting genes. In all cases, these new annotations map to the "coding" strand of DNA among genes which are part of polycistronic units. This result is consistent with the model of kinetoplastid genes being clustered in large transcriptional units on the coding strand of DNA (Martinez-Calvillo et al., *Mol Cell* 11, 1291 (May 2003)). Strand-switch regions separate these clusters and allow for changing of the coding strand at sites of transcription initiation. Thus, although transcriptional activity on the "non-coding" DNA strand has been documented (Worthey et al., *Nucleic Acids Res* 31, 4201 (Jul. 15, 2003)), the proteome does not provide evidence for translation of those alternative strand transcripts.

High-throughput proteome analyses are inherently incomplete, as the available methodologies do not have sufficient dynamic range to identify and quantify all proteins expressed in an organism. In this analysis, nearly 50% of all of the spectra matching to proteins mapped to the 67 most abundant protein groups. A higher number of lower abundance proteins can likely be revealed by depleting these highly abundant proteins prior to whole proteome analysis. Analysis of the proteomes of *T. cruzi* reveals the operation of several previously undocumented stage-specific pathways that could be appropriate targets for drug intervention. Among the most interesting of these are the proposed pathways for energy generation in amastigotes and epimastigotes. Additionally, the identification of the proteins expressed in abundance in trypomastigotes and amastigotes of *T. cruzi* provides a substantial new resource of candidates for vaccine development. This proteome analysis of *T. cruzi* also validates the high quality of the gene predictions generated by the *T. cruzi* genome sequencing consortium by confirming the expression of >1000 hypothetical genes and at the same time revealing <15 genes missed in the initial annotation.

Data on all peptides mapping to annotated genes is available from *T. cruzi* databases such as, for example, TcruziDB (CTGED, Athens, Ga.). Raw data in either the original peak-list (.PKL) format or in mzData XML format (MIAPE standard) can be downloaded from *T. cruzi* databases such as, for example, The *Trypanosoma cruzi* Proteome (CTGED, Atehns, Ga.). Complete lists of all peptides identified, pre-run queries identifying proteins expressed in specific life-cycle stages as well as tools to query and view these data are also available from *T cruzi* databases such as, for example, TcruziDB and The *Trypanosoma cruzi* Proteome.

Example II

Candidate Genes for Knockout (Live Vaccine) and/or Drug Development

Several classes of genes are illustrated as candidates for gene knockout (for subsequent use as a live vaccine) and/or as possible drug targets. The identifying numbers used herein are gene ID numbers from the *T. cruzi* database; available on the worldwide web at tcruzidb.org and at genedb.org.

1. Genes Involved in Fatty Acid Metabolism

Surprisingly, we found in our proteomic analysis of *T. cruzi* (Example I; Atwood et al. (2005) *Science,* 309, 473-476) that genes involved in the β-oxidation of fatty acids are up-regulated in amastigotes, suggesting that this parasite stage utilizes fatty acid oxidation as an important energy source. Interestingly, both muscle cells and adipocytes, which are the major host cells from *T. cruzi* in chronically infected hosts, derive most of their energy from fatty acid beta oxidation. Fatty acids are therefore expected to be readily accessible to *T. cruzi* living in the cytoplasm of these cells. Thus, enzymes involved in fatty acid metabolism, particularly in β-oxidation of fatty acids, are excellent candidates for gene knockout to produce avirulent vaccine strain of *T. cruzi*.

Most eukaryotic cells have two fatty acid β-oxidation pathways—one in the mitochondria and the other in the peroxisomes and/or glycosomes. Genes from either of these pathways represent candidates for knockout or drug targeting.

One example of a gene that can be targeted to interfere with fatty acid β-oxidation in *T. cruzi* is represented by Tc00.1047053506799.10; Systematic Id 7100.t00001: fatty acid transporter protein-like (FATP), putative. The gene product of this gene is not detected in the proteome, but it is predicted to be the first step in fatty acid uptake by *T. cruzi*. A distant relative of this gene exists in the related *Leishmania*, which has been shown to transport fatty acids in the intracellular amastigote stage (Berman, et al. J. Parasitol. 73:555 1987), but a similar gene is not found in the related *T brucei* which lacks an intracellular stage. This gene is predicted to have a non-cleavable signal sequence, thus the gene product is likely surface-expressed. It shows strong homology to other FATP proteins and is the only *T. cruzi* gene containing the highly conserved IYTSGTTGXPK (SEQ ID NO:2) motif characteristic of this class of transporters. The gene appears to be a single copy gene and thus represents an excellent knockout candidate.

Another example is represented by Tc00.1047053504177.20 and Tc00.1047053506261.10; 4947.t00002 and 6875.t00001: fatty acyl CoA synthetase 2. Fatty acyl coA synthetases have also been shown to participate in fatty acid internalization in cells Marszalek et al., J Biol Chem. 2004 Jun 4;279(23):23882-91) and in addition are considered the second step in the import pathway toward β-oxidation of long-chain fatty acids. One complication of these genes in *T. cruzi* is that there are multiple sets of similar genes, making generation of knockouts more complicated. However, these different genes may have distinct functions and this is indeed suggested in the proteome analysis. Tc00.1047053503575.50 (fatty acyl CoA synthetase, putative; 4646.t00005 is detected in the metacyclic stage only while Tc00.1047053506261.10 and Tc00.1047053504177.20 are detected primarily in the amastigote stage. Tc00.1047053510943.33 (8550.t00024) and Tc00.1047053506829.110 (7108.t00011) fatty acyl CoA synthetase 2, putative are also detected (but not with high scores) exclusively in amastigotes.

Another example is an acyl CoA dehydrogenase, representing the first step in the β-oxidation pathway, with production of $FADH_2$. There are 20 genes in *T. cruzi* with homology to each other and to acyl CoA dehydrogenases in other organisms as noted in the Kyoto Encyclopedia of Genes and Genomes (KEGG; available on the world wide web at genome.jp/kegg/) pathways developed by Fairlamb (see http://tbdb.bioinformatics.dundee.ac.uk/kegg/and Berriman, et al., Science. 2005 Jul 15;309(5733):416-22). Ten of these genes appear to be annotated as true acyl-CoA DH; others are hypothetical. Tc00.1047053509153.120 (8016.t00012) and Tc00.1047053510303.290 (8359.t00029)—acyl-CoA dehydrogenase, putative, appear to be expressed only in the amastigote and metacyclic stages, based upon proteome analysis.

Another example is enoyl CoA hydratase, which represents the $2^{nd}$ step in β-oxidation pathway. The KEGG pathways suggest as many as 20 homologues; five of these are annotated as enolyl CoA hydratases. Tc00.1047053511529.160 (6142.t0006) and Tc00.1047053506727.100 (7070.t00010) enoyl-CoA hydratase/isomerase family protein, putative, as well as a few others, have some specificity for expression in the amastigote proteome; most of others appear to be mixed in various stages. Some with signal peptides and may be targeted for the mitochondria.

Another example is β-hydroxyacyl-CoA dehydrogenase, representing the $3^{rd}$ step in β-oxidation pathway. There are several possibilities for interfering, directly or indirectly, with this enzyme:

a. One target is a trifunctional enzyme that has enoyl-CoA hydratase, delta3-cis-delta2-trans-enoyl-CoA isomerase and 3-hydroxyacyl-CoA dehydrogenase activities, based upon similarity to a bacterial gene product (Ralstonia solanacearum—a plant pathogen). See Tc00.1047053507547.40 (7378.t00004) and Tc00.1047053508441.70 (7730.t00007). This trifunctional enzyme is the peroxisomal version in many cells, whereas the enzyme functions are typically in two different proteins in the mitochondrial versions.

b. Another target is a long-chain 3-hydroxyacyl-CoA dehydrogenase (tc00.1047053508117.10) which appears to be unique to *T. cruzi* according to KEGG.

c. Another target is an apparent mitochondrial trifunctional alpha subunit. This protein is detected in the *T. cruzi* proteome but is lowest in trypomastigote/amastigote stages. See Tc00.1047053509701.10—Vibrio homologue.

d. Another target is Tc00.1047053503453.70, which is a large (0.4 kb) hypothetical gene with homology to a fatty acid oxidation complex in bacteria.

Another example of a gene that can be targeted to interfere with fatty acid β-oxidation in *T. cruzi* is one that encodes a β-ketoacyl-CoA thiolase (acyl-CoA acetyltransferase) EC 2.3.1.16; Tc00.1047053510507.20 (8414.t00002) and Tc00.1047053509463.30 (8107.t00003). The gene product has strongest similarity to Mtb protein, and there are homologues in *T. brucei* and *Leishmania*. This gene is strongly expressed in the proteome in all stages except trypomastigotes. A second set of genes is represented by Tc00.1047053511389.150 (8680.t00015) and Tc00.1047053407477.1, also detected in the proteome. Also a potential target is the gene represented by Tc00.1047053511003.60 (EC 2.3.1.9)—involved in the final step in last round of fatty acid degradation. This is a single gene in *T. brucei, T. cruzi* and *Leishmania*. It is annotated as hypothetical but highly expressed in all stages in *T. cruzi* except trypomastigote.

Another example is a choline/carnitine O-acyltransferase, Tc00.1047053511353.4 (8669.t00009) and Tc00.1047053511301.80 (8652.t00008), a putative transporter for movement of fatty acids from the cytoplasm to the mitochondria. This protein is present in Leishmania, but not in *T. brucei*. The proteome score shows that it is present only in the amastigote stage. It has the strongest homology to human carnitine palmitoyltransferase I, mitochondrial.

Another example is a carnitine/choline acetyltransferase, putative Tc00.1047053509999.90 (5825.t00009) and Tc00.1047053503685.30 (4701.t00003). It is expressed at the highest level in amastigote and metacyclic stages, but also detected in the epimastigote stage. The encoded protein has a mitochondrial energy transfer protein signature.

Other examples included other carnitine acyltransferase/translocase homologues (e.g. Tc00.1047053511807.284 carnitine O-palmitoyltransferase II, putative 8792.t00035, which were either not detected in amastigote or in any stage.

2. Non-β-Oxidation Pathway Genes

Other genes that are expected to be good knockout candidates include, for example, those that exhibit stage-specific expression (particularly in amastigotes), and those that are unique to *T. cruzi* (e.g., are not found in *Leishmania* or *T. brucei*), particularly transporters that are unique to *T. cruzi*. Proteins unique to *T. cruzi* are postulated to be involved in a unique and/or important aspect of *T. cruzi* biology.

An example of a non-β-oxidation gene that can be targeted includes those that encode an aspartate aminotransferase, e.g., aspartate aminotransferase, putative; 4698.t00001 (Tc00.1047053503679.10) which is preferentially detected in the amastigote proteome. Aspartate aminotransferases have been cloned and expressed from *Crithidia fasciculata*, *Trypanosoma brucei brucei*, *Giardia intestinalis*, and *Plasmodium falciparum* and have been found to play a role in the final step of methionine regeneration from methylthioadenosine.

Another example of a non-β-oxidation gene that can be targeted includes those that encode a guanine deaminase, e.g., 7541.t00015 (Tc00.1047053507951.150; guanine deaminase, putative). Guanine deaminase plays a major role in the purine salvage pathway of this organism, as judged from growth experiments and enzyme inhibition studies.

Another example of a non-β-oxidation gene that can be targeted includes those that encode a polyprenyl synthase, e.g., 8647.t00008 (Tc00.1047053511289.80 |||polyprenyl synthase, putative). Defects in this gene in *Leishmania* result in alterations in protein GPI anchor, and GIPL biosynthesis, but despite the absence of these structures, which have been implicated in parasite virulence and viability, the mutant remains infectious to macrophages and mice.

Another example of a non-β-oxidation gene that can be targeted includes those that encode a mannose-1-phosphate guanyltransfase, e.g., 8551.t00001 (Tc00.1047053510947.10 |||mannose-1-phosphate guanyltransfase). GDP-MP is a cytoplasmic protein, and the deletion of the gene in *Leishmania mexicana* did not affect parasite viability but led to a total loss of virulence, making GDP-MP an ideal target for anti-*Leishmania* and anti-*T. cruzi* drug development.

Another example of a non-β-oxidation gene that can be targeted includes those that encode a 4-diphosphocytidyl-2C-methyl-D-erythritol synthase, e.g., 8643.t00025 (Tc00.1047053511277.250; hypothetical protein, conserved).

Another example of a non-β-oxidation gene that can be targeted includes those that encode a nuclease of unknown function, i.e., 6191.t00005 (Tc00.1047053511727.50; hypothetical protein, conserved), that is detected primarily in amastigotes.

Another example of a non-β-oxidation gene that can be targeted includes those that encode a protein transport protein of unknown function (i.e., 6890.t00029 (Tc00.1047053506297.290; protein transport protein sec31, putative) that is expressed preferentially in amastigotes, Another example of a non-β-oxidation gene that can be targeted includes hypothetical protein 8148.t00010 (Tc00.1047053509601.100; hypothetical protein, conserved) of unknown function that are preferentially expressed in amastigotes.

Transporters that are unique to *T. cruzi* and, in some instances, may be involved in metabolic pathways that are stage specific, include the following. Some were obtained from the Transport Classification Database (available on the world wide web at tcdb.org/) as initially described in the *T. brucei* genome paper, Berriman et al., Science. 2005 Jul 15;309(5733):416-22.

1. Tc00.1047053510741.170 (8480.t00017; SEQ ID NOs: 3 and 4)-potential Glucose-6-phosphate:pi antiporter. This is likely to be the G-6-P transporter involved in transport of G-6-P from host cytoplasm into amastigote. We predict G-T-P to be the other energy source besides fatty acids for amastigote stages.
2. Tc00.1047053506577.60 (7005.t00006; SEQ ID NOs: 5 and 6) reported as a histidine symporter. This transport protein is reported as a short, multipeptide membrane-bound transporter and may represent the way to get histidine into epimastigotes.
3. Tc00.1047053507709.60 (5506.t00006; SEQ ID NOs: 7 and 8)—appears to be a dipeptide symporter. This transport protein is predicted to be in membrane and may be involved in import of peptides/amino acids into epimastigotes and/or amastigotes.
4. Tc00.1047053508317.50 (5569.t00005; SEQ ID NOs: 9 and 10)-ammonium transporter. This transporter, also predicted to be in the membrane, may be involved in getting rid of ammonium left from the first step in histidine utilization.
5. Tc00.1047053503559.70 (4638.t00007; SEQ ID NOs: 11 and 12)—Cystinosin, putative. This protein may be involved in the transport of proteins/peptides in or out of the lysosome as part of degradation for energy metabolism.
6. Tc00.1047053511501.30—ABC transporter, putative (8709.t00003; SEQ ID NOs: 13 and 14)—one of many ABC transporters. This particular one may be a palatinose (sugar) transporter.
7. Amino acid/energy intermediates transporters. These transporters may be involved in moving some of these unique metabolites in or around the cell.
   a. Tc00.1047053507709.60 hypothetical protein, conserved (5506.t00006) peptide transporter PepT1.
   b. Tc00.1047053504213.110 amino acid permease, putative (4965.t00011), involved in aspartate, glutamate, asparagine, and glutamine uptake.
   c. Tc00.1047053511249.10 ADP/ATP mitochondrial carrier protein, putative 8634.t0001, is an aspartate, glutamate antiporter.
   d. Tc00.1047053507813.10 structural maintenance of chromosome 3 protein, putative 7480.t00001, is a glutamine porter.

Examples of proteins that represent good targets for the development of inhibitors and drugs are those that increase susceptibility of *T. cruzi* to immune effectors or drugs. In some instances, they are involved in metabolic pathways that are stage specific, include the following. Some were obtained from the Transport Classification Database (available on the world wide web at tcdb.org/).

8. Inhibitors of Toxins/Drugs: Increase Susceptibility of Parasite to Immune Effectors or Drugs (Infect and Treat Studies)
   a. Tc00.1047053508465.40 hypothetical protein, conserved 7741.t00004 fosfomycin resistance protein YceE motif.
   b. Tc00.1047053510225.59 transporter, putative 5869.t00006—possible tetracycline antiporter
   c. Tc00.1047053506779.90 hypothetical protein, conserved 7094.t00009—NO3/NO2 antiporter motif.
   d. Tc00.1047053506771.18 hypothetical protein, conserved 7090.t00002—possible peroxisomal carrier—mitochondrial membrane.
   e. Tc00.1047053503521.39 mitochondrial carrier protein, putative 4619.t00010 also a peroxisomal carrier.
   f. Tc00.1047053506619.90 ABC transporter, putative 7024.t00009 Pfindr1 motif.
   g. Tc00.1047053506457.149 hypothetical protein, conserved: 6952.t00016 drug/sterol/mutagen exporter motif.
   h. Tc00.1047053510231.29 multidrug resistance-associated protein, putative 5870.t00003 drug resistance pump.
   i. Tc00.1047053506559.100 multidrug resistance-associated protein, putative 6996.t0000100 drug resistance pump.

Other interesting transporters that are suitable for as drug or knockout targets include:
   a. Cereolysin (hemolysin)—set of 5. These are all putative trans sialidase proteins.
   b. Tc00.1047053511753.100 ABC transporter, putative 8774.t000010—a nitrate/nitrite porter. Only *T. cruzi* has this porter motif; *T. brucei* and *Leishmania* do not.

3. Genes Involved in Histidine Metabolism in *T. cruzi*

Figure 11:
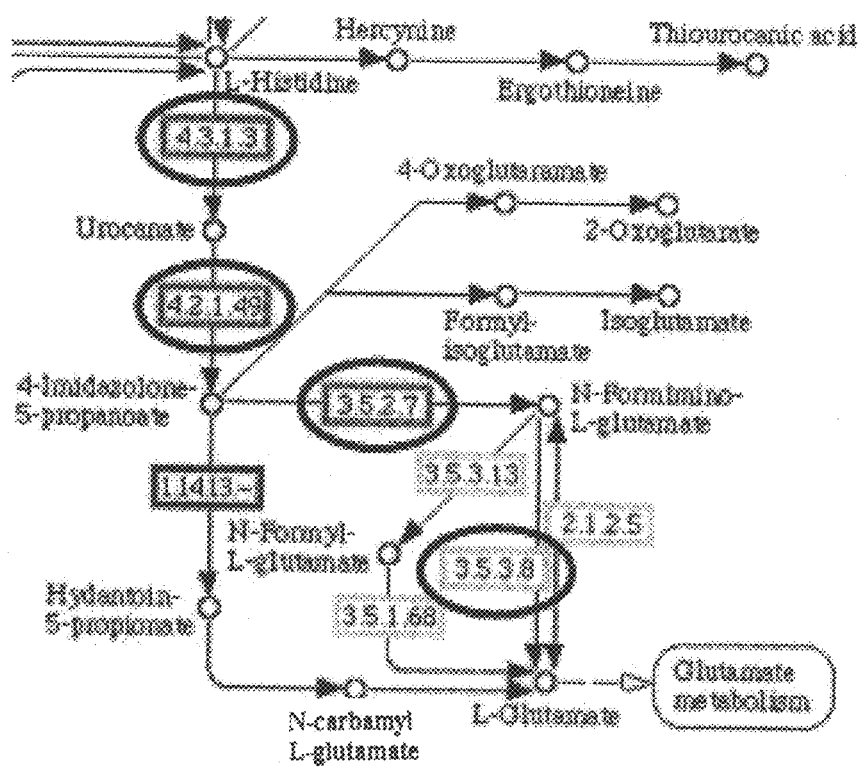

It is interesting to note that all four enzymes in the pathway from conversion of histidine to glutamate are present in *T. cruzi*, but absent in the *T. brucei* and *Leishmania* genomes (FIG. 11). Three of these four enzymes are found in the epimastigote/metacyclic trypomastigotes proteomes. Histidine is documented to be abundant in the insect vector gut, since hemoglobin (present after a blood meal) has a high abundance of histidine. Further, *T. cruzi* exists in two life cycle stages in insects: epimastigote and metacyclic trypomastigote. Thus, it is likely that *T. cruzi* epimastigotes and metacyclics use histidine as an energy source in insects.

Thus, the following genes and proteins they encode, which are involved in histidine metabolism, represent illustrative targets for drug design and vaccines. An example of a useful vaccine is a polypeptide vaccine that includes a histidine transporter or immunogenic subunit or analog thereof. This vaccine could be administered to dogs to produce an immune response (humoral and/or cell-mediated) against the histidine transporter antigen. When an insect feeds on the dog, it takes up immune factors, such as antibodies and T cells, that may effectively block infection in the insect.

EC 4.3.1.3; histidine ammonia-lyase; histidase; histidinase; histidine alpha-deaminase;
Reaction: L-histidine=urocanate+NH3
Gene ID (Link to GeneDB) GOtcha resultsP-scoreSequence

| tc00.1047053506247.220 | GOtcha | 110 | tcruzi_v2:tc00.1047053506247.220 |

By homology, this gene seems to be most closely related to a human enzyme. The gene product is detected in the epimastigote and metacyclic proteome, and is unique to *T. cruzi*.

EC 4.2.1.49; urocanate hydratase; urocanase
Reaction: 3-(5-oxo-4,5-dihydro-3H-imidazol-4-yl) propanoate=urocanate+H2O
Gene ID (Link to GeneDB) GOtcha resultsP-scoreSequence

| tc00.1047053504045.110 | GOtcha | 110 | tcruzi_v2:tc00.1047053504045.110 |

By homology, this gene seems to be most closely related to a human enzyme. The gene product is detected in the epimastigote and metacyclic proteome, and is unique to *T. cruzi*.

EC 3.5.2.7; imidazolonepropionase; 4(5)-imidazolone-5(4)-propionic acid hydrolase;
imidazolone propionic acid hydrolase
Reaction: (S)-3-(5-oxo-4,5-dihydro-3H-imidazol-4-yl)propanoate+H2O=N-formimidoyl-L-glutamate+H+
Gene ID (Link to GeneDB) GOtcha resultsP-scoreSequence

| tc00.1047053509137.30  | GOtcha | 110 | tcruzi_v2:tc00.1047053509137.30  |
| tc00.1047053508741.140 | GOtcha | 110 | tcruzi_v2:tc00.1047053508741.140 |

This gene has not yet been detected in the proteome, and the gene product is unique to *T. cruzi*

EC 3.5.3.8; formimidoylglutamase; formiminoglutamase; N-formiminoglutamate hydrolase; N-formimino-L-glutamate formiminohydrolase

| *T. cruzi* | CDS | Tc00.1047053507031.90 | arginase, putative, 7547.t00002 |
| *T. cruzi* | CDS | Tc00.1047053509497.30 | arginase, putative, 8551.t00004 |
| *T. cruzi* | CDS | Tc00.1047053510947.40 | arginase, putative, 5727.t00003 |
| *T. cruzi* | CDS | Tc00.1047053507963.20 | arginase, putative, 5428.t00009 |

This gene product is detected in the epimastigote and metacyclic proteome. The gene is annotated as an Arginase in *T. cruzi*, and is not present in *T. brucei*.

A homologue in *Leishmania* may be LmjF35.1480 7547.t00002. The closest homologue in GenBank is ZP_00356496. COG0010: Arginase . . . [gi:53795417]

| LOCUS | ZP_00356496 | 319 amino acids | linear | BCT 05-OCT-2004 |

DEFINITION COG0010: Arginase/agmatinase/formiminoglutamate hydrolase, arginase family [Chloroflexus aurantiacus].

It should be noted that for vaccine development, a genetically engineered *T. cruzi* that contains more than one gene knockout as described herein is preferred, since the more genes that have been knocked out (still yielding a viable organism), the less chance there is for reversion to a pathogenic organism.

Example III

Highly Abundant T. cruzi Proteins

The 67 most abundant proteins (based upon cumulative Mascot scores; see Example I) representing 47% of all mass spectra collect for the *T. cruzi* proteome were identified and are shown in Table 9. Groups of redundant proteins (proteins with greater than 50% homology by BLAST analysis) were identified and a single member of a redundant group was selected, reducing the final number of genes to 48. These genes were then cloned by PCR and recombinant proteins produced from these genes in *E. coli* were pooled and used to generate antibodies in rabbits.

TABLE 9

| | | |
|---|---|---|
| 14-3-3 protein 3 (14-3-3-3) (fragment) | ? | Tc00.1047053511589.130 |
| alpha tubulin | microtubules = DNA rep, mobility, support | Tc00.1047053411235.9 |
| arginine kinase | ARG + MgATP <--> ARG P + MgADP + H+ | Tc00.1047053507241.30 |
| ATP synthetase F1, beta subunit | oxidative phosphorylation with e-trans. chain | Tc00.1047053509233.180 |
| beta tubulin 2.3 | microtubules = DNA rep, mobility, support | Tc00.1047053506563.40 |
| calmodulin - *Trypanosoma cruzi* | Ca-binding reg prot, smallest su phosphorylas kinase | Tc00.1047053506391.10 |
| chaperonin hsp60, mitochondrial precursor (protein) | heat shock & assists normal prot folding | Tc00.1047053507641.290 |
| cyclophilin A | pre mRNA splicing | Tc00.1047053506925.300 |
| cystathionine beta-synthase 5 | serine + homocysteine (from MET) cat --> cystathionine | Tc00.1047053508241.140 |
| dehydrogenase-related | remove H from substrate or oxidize substrate | Tc00.1047053510099.120 |
| elongation factor 2 | extend growing peptide chain in translation | Tc00.1047053510963.90 |
| enolase | glycolysis | Tc00.1047053504105.140 |
| Fructose-bisphosphate aldolase class-I | glycolysis | Tc00.1047053504163.50 |
| glyceraldehyde-3-phosphate dehydrogenase, type 1 | TCA cycle & glycolysis | Tc00.1047053506943.50 |
| heat shock 70 kda protein, mitochondrial precursor | help prot refold to native conf in increased T | Tc00.1047053507029.30 |
| heat shock like 85 kda protein-related | help prot refold to native conf in increased T | Tc00.1047053509643.130 |
| heat shock protein | help prot refold to native conf in increased T | Tc00.1047053506585.40 |
| heat shock protein HSP70 | major HSP, prevent entrapment of nascent prot in low E well | Tc00.1047053511211.170 |
| histone h2b | DNA-associated in chromatin | Tc00.1047053511635.10 |
| histone H3, probable | DNA-associated in chromatin | Tc00.1047053509471.68 |
| histone H4, putative | DNA-associated in chromatin | Tc00.1047053508203.56 |
| hypothetical protein | ? | Tc00.1047053510877.30 |
| hypothetical protein | ? | Tc00.1047053505989.110 |
| hypothetical protein | paraflagellar rod protein 3 | Tc00.1047053509617.20 |
| hypothetical protein | ? (likely peroxiredoxin/tryparidoxin peroxidase) | Tc00.1047053508719.70 |
| hypothetical protein, to be annotated (newly added) | ? (likely flagellar, Ca-binding protein) | Tc00.1047053509499.14 |
| hypothetical protein, to be annotated (newly added) | ? | Tc00.1047053507491.151 |
| hypothetical protein, to be annotated (newly added) | stimulates production of autoantibodies | Tc00.1047053511633.79 |
| i/6 autoantigen-related | ? | Tc00.1047053511825.80 |
| Igr3p | ? | Tc00.1047053506635.130 |
| kinetoplast DNA-associated protein 4 precursor - C | DNA-associated (like histone?) | Tc00.1047053509791.120 |
| malate dehydrogenase, NAD-dependent | TCA cycle & urea cycle | Tc00.1047053506195.110 |
| malic enzyme, NAD binding domain, putative | malate cat --> puruvate + CO2 = oxidative decarboxylation | Tc00.1047053508647.280 |
| phosphoenolpyruvate carboxykinase | gluconeogenesis | Tc00.1047053508441.20 |
| phosphoglycerate kinase | glycolysis | Tc00.1047053511419.50 |
| putative glutamate dehydrogenase | urea cycle | Tc00.1047053508111.30 |
| pyruvate, phosphate dikinase | ATP + pyruvate + phosphate cat --> AMP + PEP + diphosphate | Tc00.1047053506297.190 |
| ribosomal protein L10, putative | translation | Tc00.1047053508355.250 |
| SSE1 | HSP (help prot refold to native conf in increased T) | Tc00.1047053507831.60 |
| surface glycoprotein GP90 | membrane prot | Tc00.1047053509513.10 |
| TCJ2 | HSP (help prot refold to native conf in increased T) | Tc00.1047053511627.110 |
| TcSTI1 | stress-induced protein 1 | Tc00.1047053506321.290 |
| translation elongation factor EF-1, subunit alpha | translation | Tc00.1047053511367.360 |
| tryparedoxin peroxidase homologue | cat reduction of reactive O species --> H2O/alcohols via redox-active cysteines | Tc00.1047053509445.10 |

TABLE 9-continued

| tyrosine aminotransferase | transfer amino group from GLU to ?-keto acids to make ?-amino acids (tyrosine) | Tc00.1047053510187.50 |
| --- | --- | --- |
| succinyl-CoA synthetase beta chain | succinyl CoA cat --> succinate - to generate NTP (GTP) | Tc00.1047053507681.20 |
| 2-amino-3-ketobutyrate coenzyme A ligase | degrade L-threonine to glycine (aka: glycine C-acetyltransferase, aminoacetone synthase) | Tc00.1047053511899.40 |
| TolT3, putative | maintain membrane structural integrity | Tc00.1047053510433.20 |

The complete disclosure of all patents, patent applications, and publications cited herein are incorporated by reference.

What is claimed is:

1. A genetically engineered *Trypanosoma cruzi* (*T. cruzi*) wherein expression of an amastigote stage-regulated protein has been reduced or eliminated, wherein the amastigote stage-regulated protein is more abundantly expressed in *T. cruzi* amastigotes than it is expressed in other *T. cruzi* stages, and wherein reducing or eliminating expression of the amastigote stage-regulated protein renders the genetically engineered *T. cruzi* avirulent.

2. The genetically engineered *T. cruzi* of claim 1 wherein the amastigote stage-regulated protein is expressed from a gene involved in energy metabolism.

3. The genetically engineered *T. cruzi* of claim 2 wherein the gene is involved in fatty acid metabolism or transport.

4. The genetically engineered *T. cruzi* of claim 3 wherein the protein expressed by the gene comprises an acyl transferase.

5. The genetically engineered *T cruzi* of claim 3 wherein the protein expressed by the gene comprises a fatty acid transporter protein.

6. The genetically engineered *T. cruzi* of claim 2 wherein the gene is involved in histidine metabolism or transport.

7. A method for inducing an immune response in a mammal against *T. cruzi* comprising administering to the mammal a composition comprising the genetically engineered *T cruzi* of claim 1.

8. The genetically engineered *T. cruzi* of claim 1 wherein the amastigote stage-regulated protein is expressed from a transporter gene.

9. The genetically engineered *T. cruzi* of claim 8 wherein the protein expressed by the transporter gene comprises a transporter protein that transports a metabolite into *T cruzi*.

10. The genetically engineered *T. cruzi* of claim 8 wherein the protein expressed by the transporter gene is located in the cell membrane of the *T cruzi*.

11. The genetically engineered *T. cruzi* of claim 8 wherein the protein expressed by the transporter gene comprises fatty acid transporter protein, glucose-6-phosphate transporter protein, or histidine transporter protein.

12. A method for inducing an immune response in a mammal against *T. cruzi* comprising administering to the mammal a composition comprising the genetically engineered *T cruzi* of claim 8.

13. The method of claim 12 wherein the mammal is a human or a dog.

14. The method of claim 13 wherein the composition is administered by injection or ingestion.

15. The genetically engineered *T cruzi* of claim 1 wherein the amastigote stage-regulated protein is expressed from a gene that encodes Glucose-6-phosphate:pi antiporter, histidine symporter, dipeptide symporter, ammonium transporter, cystinosin, or ABC transporter.

16. The genetically engineered *T. cruzi* of claim 15 wherein the Glucose-6-phosphate:pi antiporter comprises the amino acid sequence depicted in SEQ ID NO:4, the histidine symporter comprises the amino acid sequence depicted in SEQ ID NO:6, the dipeptide symporter comprises the amino acid sequence depicted in SEQ NO:8, the ammonium transporter comprises the amino acid sequence depicted in SEQ ID NO:10, the cystinosin comprises the amino acid sequence depicted in SEQ ID NO:12, and the ABC transporter comprises the amino acid sequence depicted in SEQ ID NO:14.

17. The genetically engineered *T. cruzi* of claim 15 wherein the gene that encodes the Glucose-6-phosphate:pi antiporter is transcribed to a mRNA that encodes the amino acid sequence depicted in SEQ ID NO:4, the gene that encodes the histidine symporter is transcribed to a mRNA that encodes the amino acid sequence depicted in SEQ ID NO:6, the gene that encodes the dipeptide symporter is transcribed to a mRNA that encodes the amino acid sequence depicted in SEQ ID NO:8, the gene that encodes the ammonium transporter is transcribed to a mRNA that encodes the amino acid sequence depicted in SEQ ID NO:10, the gene that encodes the cystinosin is transcribed to a mRNA that encodes the amino acid sequence depicted in SEQ ID NO:12, and the gene that encodes the ABC transporter is transcribed to a mRNA that encodes the amino acid sequence depicted in SEQ ID NO:14.

\* \* \* \* \*